US011008543B2

(12) United States Patent
Pizzi et al.

(10) Patent No.: US 11,008,543 B2
(45) Date of Patent: May 18, 2021

(54) APPARATUS, SYSTEM AND METHOD FOR DISGREGATING A BIOLOGICAL TISSUE

(71) Applicant: ELTEK S.P.A., Casale Monferrato (IT)

(72) Inventors: Marco Pizzi, Casale Monferrato (IT); Massimo Zanin, Casale Monferrato (IT); Enrica Mortara, Casale Monferrato (IT)

(73) Assignee: ELTEK S.p.A., Casale Monferrato (IT)

( * ) Notice: Subject to any disclaimer, the term of this patent is extended or adjusted under 35 U.S.C. 154(b) by 302 days.

(21) Appl. No.: 15/762,470

(22) PCT Filed: Sep. 22, 2016

(86) PCT No.: PCT/IB2016/055654
§ 371 (c)(1),
(2) Date: Mar. 22, 2018

(87) PCT Pub. No.: WO2017/051339
PCT Pub. Date: Mar. 30, 2017

(65) Prior Publication Data
US 2018/0273892 A1    Sep. 27, 2018

(30) Foreign Application Priority Data
Sep. 25, 2015 (IT) .................. 102015000055350

(51) Int. Cl.
*C12M 1/33* (2006.01)
*C12M 1/00* (2006.01)
(Continued)

(52) U.S. Cl.
CPC ............ *C12M 45/02* (2013.01); *C12M 21/08* (2013.01); *C12M 23/28* (2013.01); *C12M 29/00* (2013.01); *C12M 41/44* (2013.01)

(58) Field of Classification Search
CPC ...... C12M 45/02; C12M 21/08; C12M 29/00; C12M 23/28; C12M 41/44
See application file for complete search history.

(56) References Cited

U.S. PATENT DOCUMENTS

2013/0295598 A1 * 11/2013 Marx .................... C12M 25/14
435/29

FOREIGN PATENT DOCUMENTS

DE     202 09 547        9/2002
DE     202095547    * 10/2002  .............. C12M 1/33
WO    WO 1996/001085    1/1996

OTHER PUBLICATIONS

Machine translation of DE20209547 (Year: 2020).*
International Search Report for PCT/IB2016/055654 dated Nov. 24, 2016, 11 pages.

* cited by examiner

*Primary Examiner* — Michael L Hobbs
(74) *Attorney, Agent, or Firm* — Nixon & Vanderhye P.C.

(57) ABSTRACT

Herein described is an apparatus for disgregating a biological tissue, such as an adipose tissue including stem and/or multipotent cells for use in regenerative medicine. The apparatus comprises a disposable device having a first duct for the passage of the biological tissue, the first duct having a first end and a second end. Each end of the first duct is configured for connection to an inlet/outlet opening of a respective handling and/or collecting device, particularly a pump device, such as a syringe. The disposable device further comprises an adjustment arrangement operable to cause a reduction of a passage section of the first duct.

19 Claims, 32 Drawing Sheets

(51) Int. Cl.
*C12M 3/00* (2006.01)
*C12M 1/34* (2006.01)

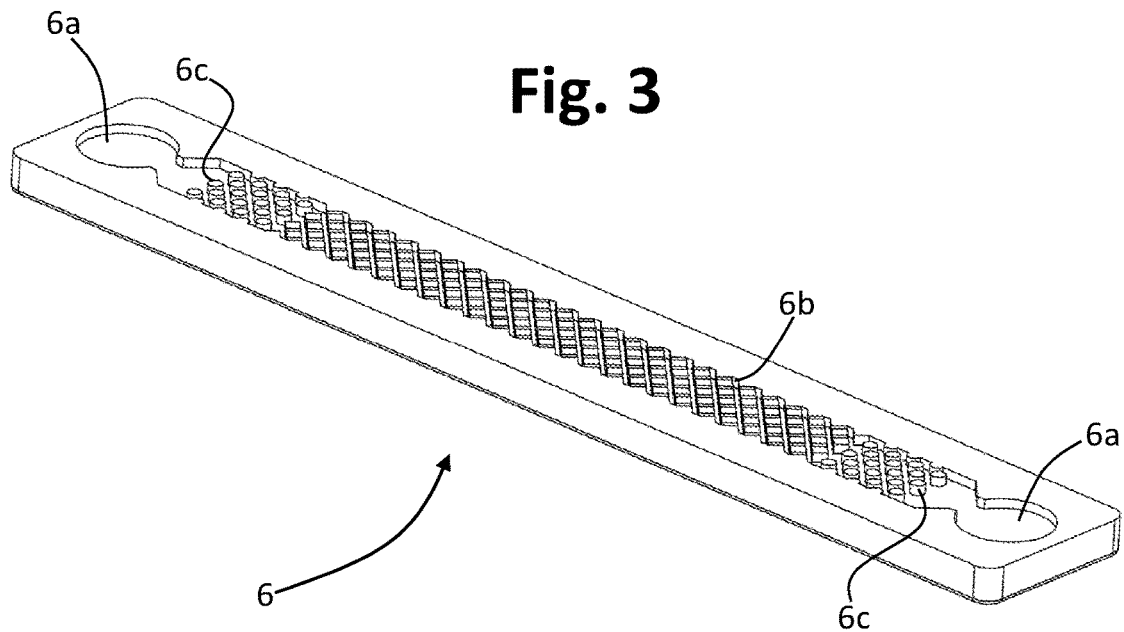
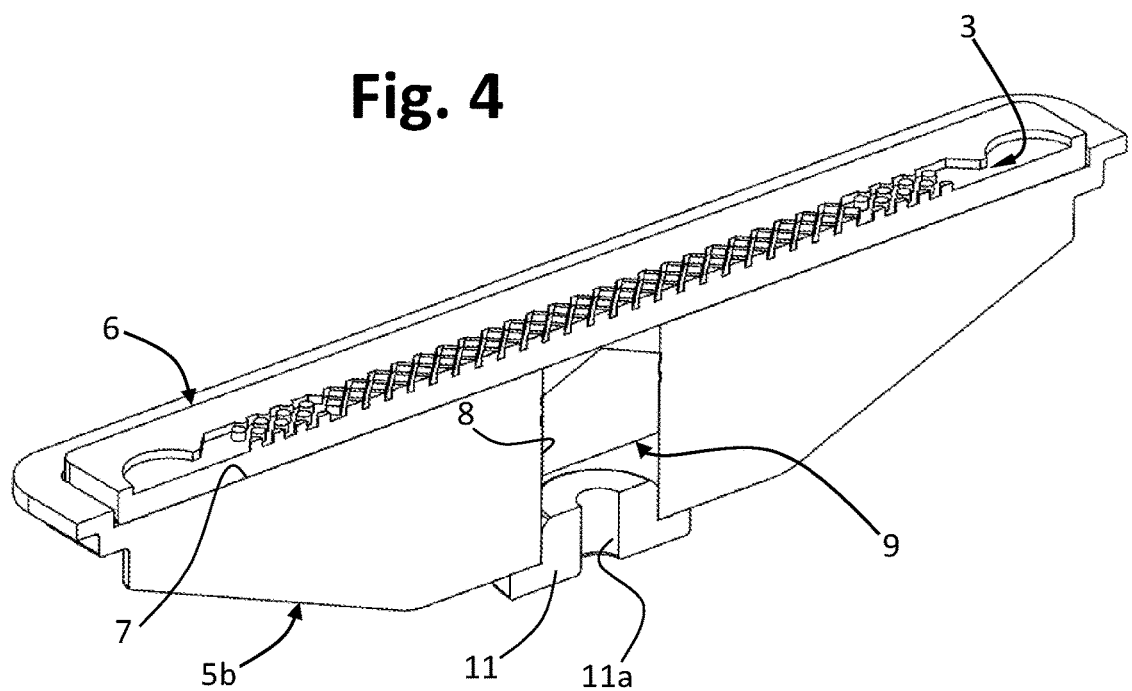

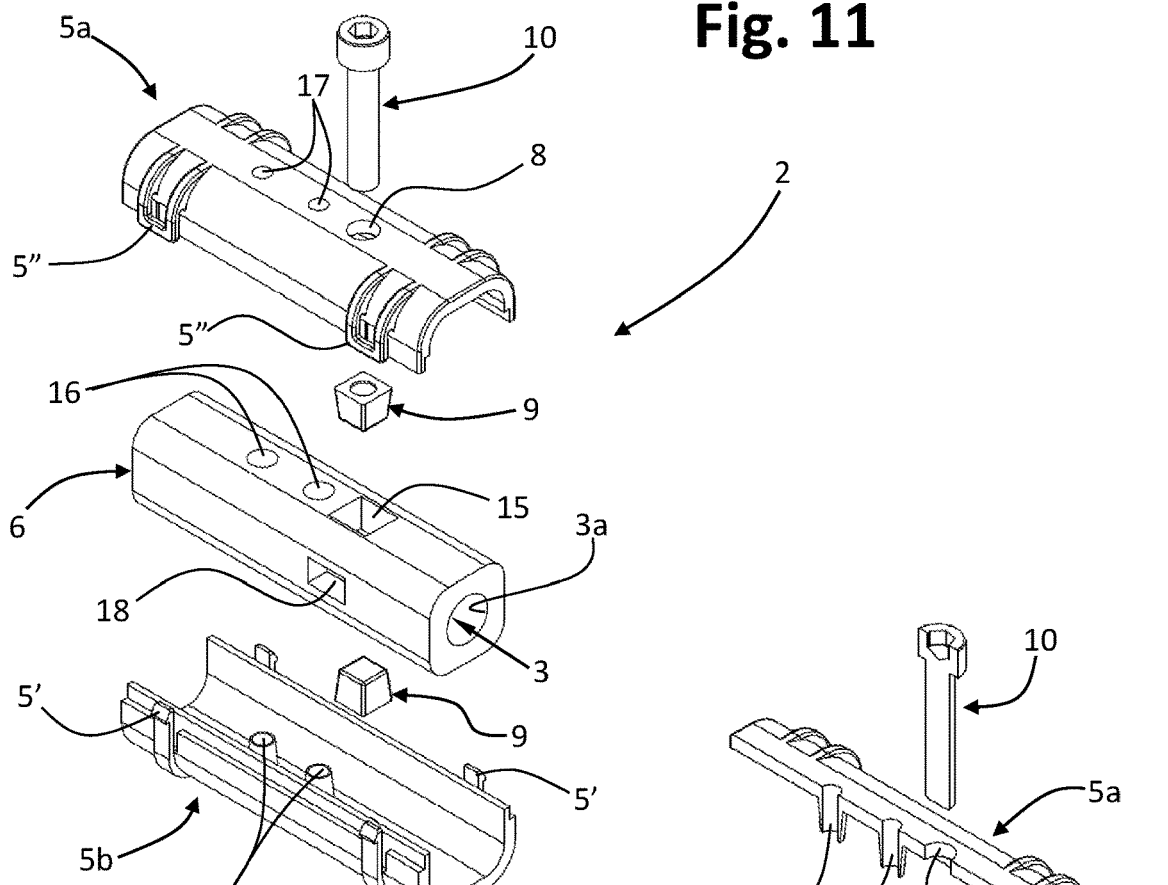
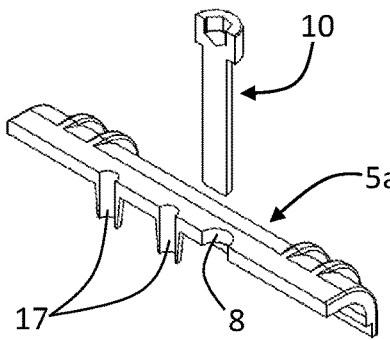
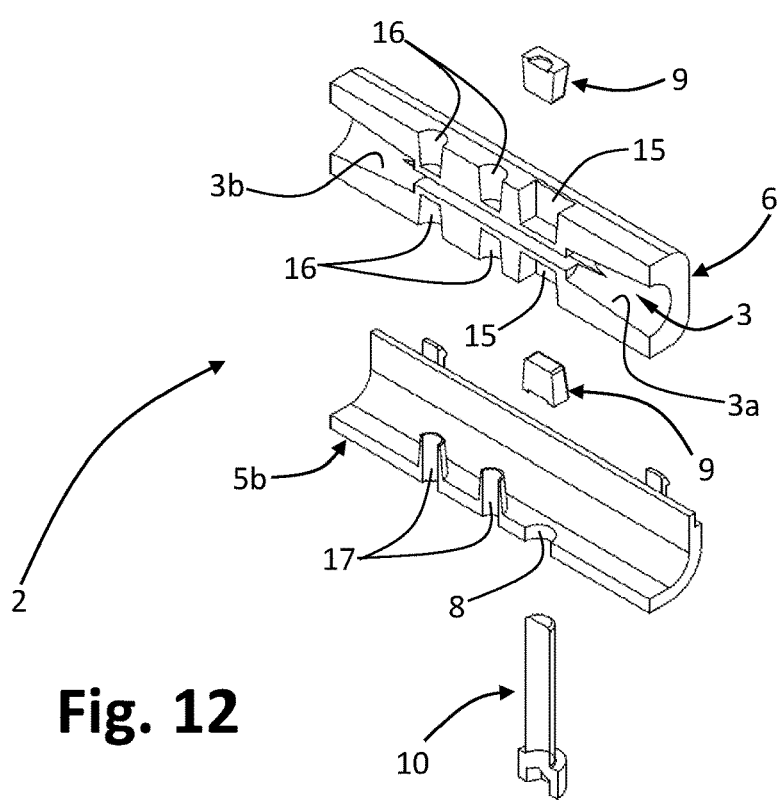
Fig. 11
Fig. 12

APPARATUS, SYSTEM AND METHOD FOR DISREGATING A BIOLOGICAL TISSUE

This application is the U.S. national phase of International Application No. PCT/IB2016/055654 filed Sep. 22, 2016, which designated the U.S. and claims priority to Italian Patent Application No. 102015000055350 filed Sep. 25, 2015, the entire contents of each of which are hereby incorporated by reference.

FIELD OF THE INVENTION

The present invention relates the so-called regenerative medicine industry and it was developed with reference to apparatuses, systems and methods for disgregating biological tissue, such as an adipose tissue, in particular with the aim of concentrating stem and/or multipotent cells, such as mesenchymal stem cells.

STATE OF THE ART

Regenerative medicine essentially aims at providing elements required for an in vivo repair of the human body, i.e., providing replacements and or aids capable of integrating with the human body, as well as stimulating and supporting the inherent capacity thereof to regenerate and heal alone.

Stem cells, i.e. primitive non-specialised cells, having the capacity to transform into other types of body cells, are an instrument used in this field. Stem cells may come from adult subjects, and in this case they are multipotent non-specialised cells, i.e. cells capable of specialising only in some types of cells. Amongst these multipotent stem cells, human mesenchymal stem cells, or hMSCs, are currently considered to be a particularly interesting instrument for the development of regenerative medicine in various contexts, such as the repair of bone and cartilaginous tissues, the myocardial tissue, the vascular tissue, the nervous tissue and tissues with endocrine function. These cells have a "self-regeneration" capacity at a considerably high speed of growth and they have broad-spectrum differentiation properties. Besides the bone marrow, hMSCs may also be obtained from alternative sources such as the dental pulp, placenta foetal membranes and the adipose tissue, which is of specific interest in the present invention.

An ideal source of hMSCs should be available in large quantities; it should be obtainable with a minimally invasive procedure and provide a population of hMSCs capable of maintaining a high level of vitality and a high differentiation potential even as the age of the donor increases. Over the last years, it has become more and more clear that the adipose tissue has these characteristics, given that it has a population of multipotent stem cells referred to as hASCs (human Adipose Stem Cells). Human beings have abundant deposits of subcutaneous fat and hASCs can be easily isolated for enzymatic digestion of lipoaspirates, thus overcoming the tissue softness associated to the collection of bone marrow. In addition, the frequency of hMSCs in the bone marrow is comprised between 1/25,000 and 1/100,000 cells, while hASCs approximately represent 2% of the cells of a lipoaspirate.

Despite the progress of hASCs isolation, several problems still remain unresolved, such as the null or negligible cell survival after freezing and thawing the lipoaspirate, ex-vivo expansion challenges, poor efficiency of the tissue delivery (less than 5% of the transplanted cells are retained in the tissue after transplantation), and the uncertain fate, also concerning differentiation in vivo. In addition, the possibility to transfer stem cells subjected to massive handling—including ex-vivo expansion in culture—to clinical applications, has been considerably hampered by the need to comply with the requirements established by the guidelines with respect to the so-called "major cellular manipulations", in compliance with the so-called "current Good Manufacturing Practice; cGMP". However, these restrictions do not apply in the case of a "non-relevant manipulation" [Regulation (EC) No 1394/2007 of the European Parliament and of the Council].

In the light of the above, it would be desirable, in view of rapid clinical development of regenerative medicine technologies, the development of treatment technologies based on "non-relevant manipulation" so as to obtain suitable products containing hASCs, ready for autologous use without any expansion, as well as susceptible to cryopreservation and possible in vitro expansion.

This result was partly achieved by applying techniques that require the centrifugation of the adipose tissue. These techniques are relatively complex and require the use of expensive equipment. In addition, the result thereof considerably depends on the ability of the designated operator, who is called upon to choose which parts of the preparation are to be selected manually.

Alternative methods, which avoid the centrifugation process, have been recently proposed: to this end, in some known solutions adipose tissues are disgregated using sieves and emulsion by grinding using metal balls. Also these procedures imply the use of relatively complex and expensive equipment. Furthermore, not only do they require high manual skills, but they are not even capable of guaranteeing product uniformity regardless of the designated operator's manual skills. In addition, these methods provide for many steps in which the adipose tissue treatment circuit remains open, thus exposing the tissue to the environment with the ensuing risk of oxidation degradation and bacterial contamination.

SUMMARY OF THE INVENTION

In the light of the above, the present invention aims at providing an apparatus for disgregating a biological or adipose tissue, preferably directed at obtaining products containing hASCs, which is inexpensive to obtain and distinguished by high simplicity of use. Another object of the invention is to provide such apparatus that does not require relevant manipulation of the treated tissue and/or that minimises contact between the treated tissue and the environment.

These and other aims, which will be more apparent hereinafter, are achieved—according to the present invention—by an apparatus for disgregating a biological or adipose tissue, in particular including stem and/or multipotent cells, having the characteristics outlined in the claims. A system and a method for disgregating a biological and/or adipose tissue, as well as a corresponding equipment, also form an object of the present invention.

DESCRIPTION OF THE DRAWINGS

Further aims, characteristics and advantages of the invention will be apparent from the detailed description that follows, outlined with reference to the attached drawings, provided solely by way of non-limiting example, wherein:

FIG. 3 is a schematic perspective view of an element of the apparatus of FIG. 1;

FIG. 4 is a perspective view of the element of FIG. 3 coupled to a corresponding supporting structure;

FIG. 11 is an exploded schematic view of a disposable device of the apparatus of FIG. 7;

FIG. 12 is a sectional exploded view of the device of FIG. 11;

DESCRIPTION OF THE PREFERRED EMBODIMENTS OF THE INVENTION

Figure 1:
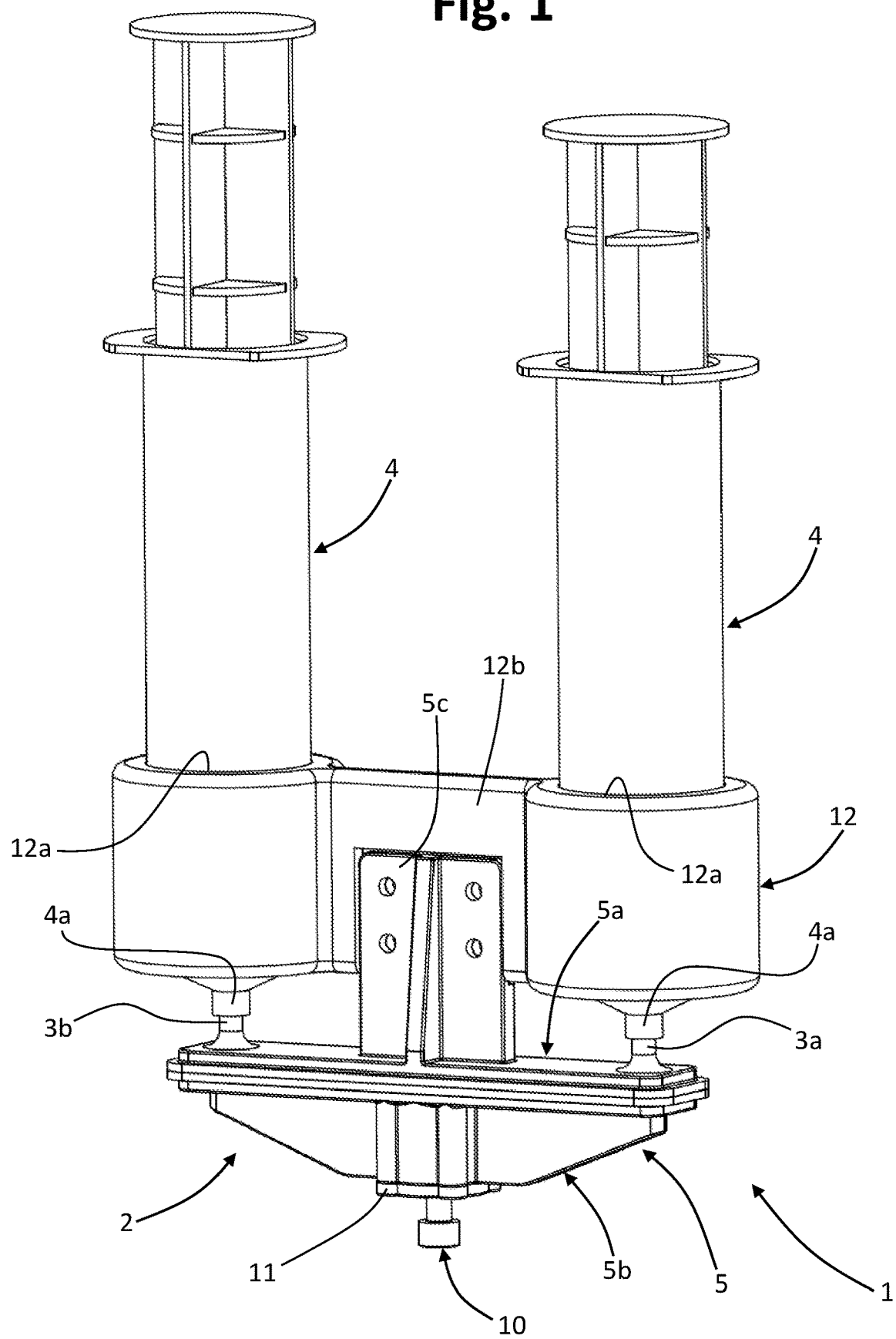
FIG. 1 is a schematic perspective view of a possible embodiment of an apparatus for disgregating an adipose tissue according to the present invention.

Reference to "an embodiment" in this description indicates that a particular configuration, structure, or characteristic described regarding the embodiment is comprised in at least one embodiment. Thus, phrases like "in an embodiment" and the like, possibly present in various parts of this description, do not necessarily refer to the same embodiment. In addition, particular configurations and/or structures and/or described characteristics may be considered singularly and/or appropriately combined, into one or more embodiments, even different from the embodiments described hereinafter by way of non-limiting example. The reference numerals used hereinafter are only for the sake of easy understanding and they do not define the scope of protection of the embodiments. In addition, the same reference numbers are used in the figures to indicate technically equivalent elements.

In its essence, the idea on which the present invention is based is that of determining a disgregation of a biological tissue, particularly an adipose tissue, through the repeated passages thereof in at least one duct, one section of which is varied, in particular progressively reduced. Hereinafter, special reference will be made to the treatment of an adipose tissue, which represents a preferred example of use of the invention, though assuming that the invention is susceptible to use even for the treatment of other types of biological tissue, both human and animal.

Preferably, the duct or the ducts which are subjected to the variation of the passage section, are isolated from the environment. In various embodiments, for the purposes of the proposed treatment, the adipose tissue is mixed with a saline (physiological) solution.

FIGS. 1-6 schematically illustrate a possible embodiment of an apparatus for disgregating an adipose tissue, particularly a tissue including stem and/or multipotent cells, for example a lipoaspirate, according to the present invention.

In the illustrated example, the apparatus, indicated as a whole with 1, comprises a disposable device 2 in which there is defined at least one first duct for the passage of the adipose tissue. Such duct, indicated with 3 in FIG. 2, has a first end 3a and a second end 3b, each of which is configured for connection to an inlet/outlet opening 4a of a respective device 4 for handling and/or collecting the adipose tissue (hereinafter referred to just as "collecting device" or "syringe" for the sake of brevity), preferably comprising at least one container for collecting the adipose tissue and means for handling the adipose tissue, such as a plunger.

As it will be clearer hereinafter, at least one of the collecting devices 4, or each collecting device 4, can be actuated to cause a flow of the adipose tissue through the duct 3, in such a way that subsequent actuations of the same device 4, or preferably of the two devices 4 in an alternating fashion, cause opposite flows of the adipose tissue through the duct 3, from the first device 4 towards the second device 4, and then from the second device 4 towards the first device 4. For this purpose, in various preferred embodiments, the collecting devices 4 comprise simple pump devices, such as for example common syringes or similar sterile containers having a variable volume collecting chamber: in the represented case, for example, the devices 4 consist of syringes, whose hydraulic connections 4a, constituted by tips herein, obtain the corresponding inlet/outlet openings.

According to the invention, the disposable device 2 further comprises an adjustment arrangement, which is operable to cause a variation of a passage cross-section of the duct 3, which can be controlled in a manual or ain an automated manner. In preferred embodiments of the invention, the adjustment arrangement is configured to enable the reduction of the aforementioned passage section: in this way, by operating at least one of the two syringes 4, the adipose tissue can be progressively disgregated by making it flow several times through the duct 3, whose passage section is varied, particularly reduced, one or several times through the aforementioned arrangement.

In various embodiments, the adjustment arrangement of the disposable device 2 comprises a deformable portion, or having a modifiable section, of the duct 3 and is operable to cause the aforementioned variation or reduction of the passage section, by deforming said portion of the duct 3 or modifying a section thereof.

Figure 2:
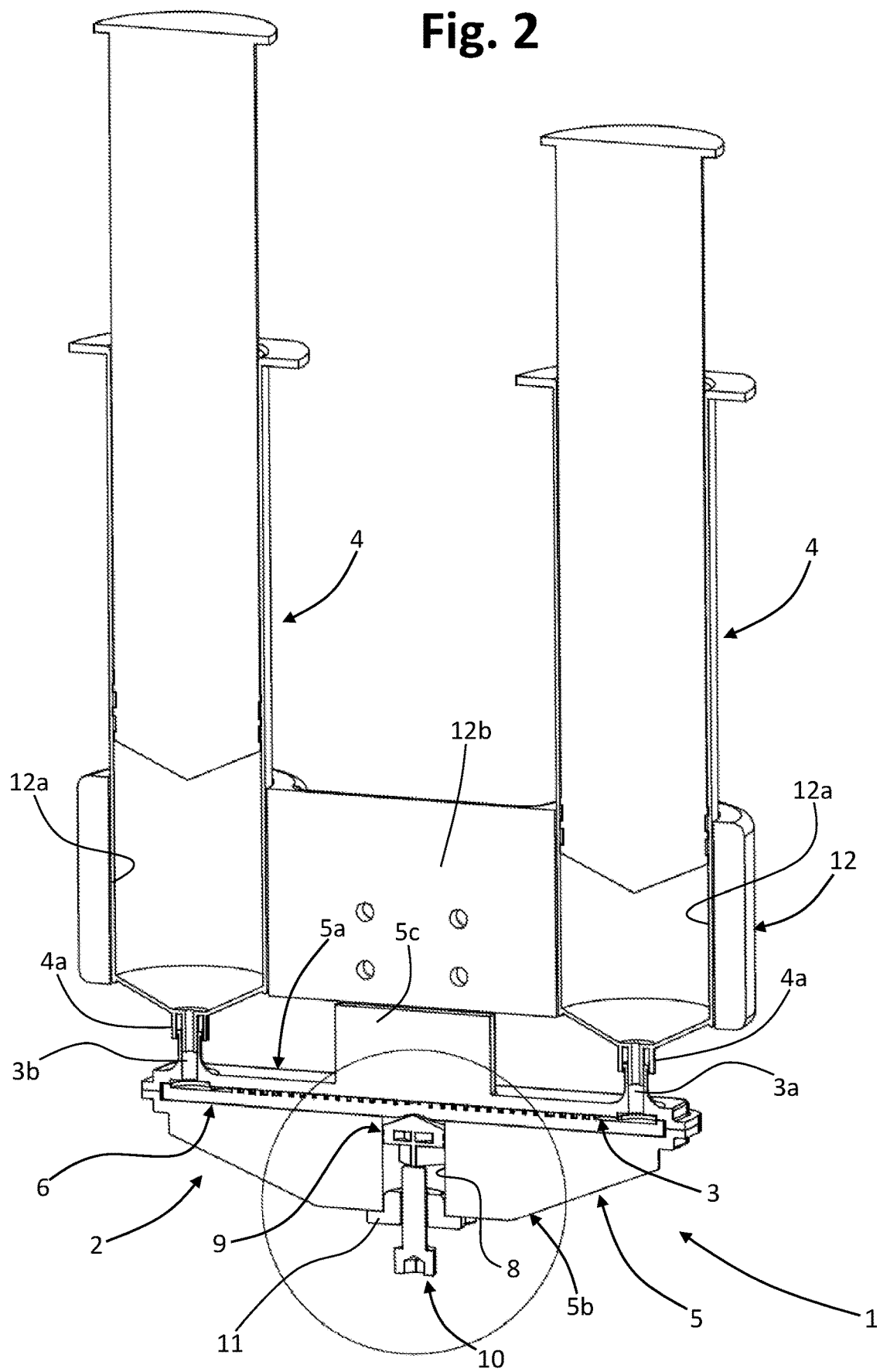
FIG. 2 is a schematic section of the apparatus of FIG. 1.

For example, with reference to the embodiment of FIGS. 1-6, the device 2 comprises a casing or supporting body 5, preferably made using a substantially rigid material, and a duct body, indicated with 6 in FIG. 2, which defines at least part of the duct 3, wherein at least one part of the body 6 which defines the deformable portion of the duct 3 is positioned in contact with the supporting body 5, preferably at least partly inside it. In various embodiments, like the ones considered herein, the supporting body of the device 2 may for example be formed using a polymer or a metal or a resin or an alloy or a thermoplastic and/or mouldable material, or with combinations of two or more of such materials: the forming of the body may be obtained by moulding (injection moulding or press moulding), including co-moulding and over-moulding.

In various embodiments, the duct 3 is partly defined by the supporting body and by the duct body. For example, in the case of FIGS. 1-6, the duct is partly defined by the body 6 and by a part of the body 5, while in other embodiments the duct body may include a tube and connection attachments defined by the body 5, or configured as a part associated to the tube. The same duct body may be made up of various parts, for example pieces of a tube connected to each other]. Moreover, the duct body may completely define the duct, with the corresponding ends shaped to serve as attachments for the syringes.

In various embodiments, such as the one exemplified in FIGS. 1-6, the supporting body 5 comprises at least two parts coupled to each other, indicated with 5a and 5b, for example made of moulded plastic material, between which there is set a duct body 6 formed at least in part by a flexible and/or deformable material. Preferably, at least one part of the supporting body 5—part 5a in this case—defines at least one corresponding portion of the duct 3, particularly an undeformable portion thereof. In the illustrated example, part 5a of the body 5 defines the ends 3a and 3b of the duct 3, which provide attachments in this case, configured for coupling with the tip 4a of a respective syringe 4. In the example, such attachments are at a face—herein conventionally defined as upper face—of the body part 5a.

With reference to FIGS. 3-6, in the illustrated example each of the two parts 5a and 5b of the supporting body 5 defines a seat or cavity 7, the two cavities being faced so as to define a housing for the duct body 6. In this embodiment, the body 6 is deformable and made of an elastomer, or a polymer or any other synthetic elastic or flexible material, for example silicone, and has a general flat and oblong configuration. On one of the larger surfaces thereof—herein referred to as "upper surface" for the sake of simplicity—the body 6 defines at least one respective part of the duct 3 for the passage of the adipose tissue. In the example, the duct part defined in the body 6 includes two seats or recessed end areas 6a, connected to each other by means of a series of recessed canalizations 6b, preferably defined in the body 6 so as to cross each other. However, in other embodiments, the crossed canalisations 6b may be replaced by a plurality of mutually parallel canalisations or by a single canalisation, in form of a groove which extends between the areas 6a.

In various embodiments, canalizations having a section and/or shape different from each other can also be provided for along the duct 3. In various embodiments, there are provided canalizations including reliefs adapted to contribute to the disgregation of the adipose tissue and/or one or more filtering elements, for example obtained through corresponding suitably shaped reliefs.

In FIG. 3 there are examples of reliefs 6c, defined in mutually offset positions in the recessed region comprised between one area 6a and the end of the part of the duct formed by the crossed canalisations 6b. Preferably, the reliefs 6c have the function of operating a filtration or coarse disgregation of the tissue, while the canalisations 6b have the function of operating a finer disgregation of the tissue, during the passage thereof through the duct 3.

Figure 5:
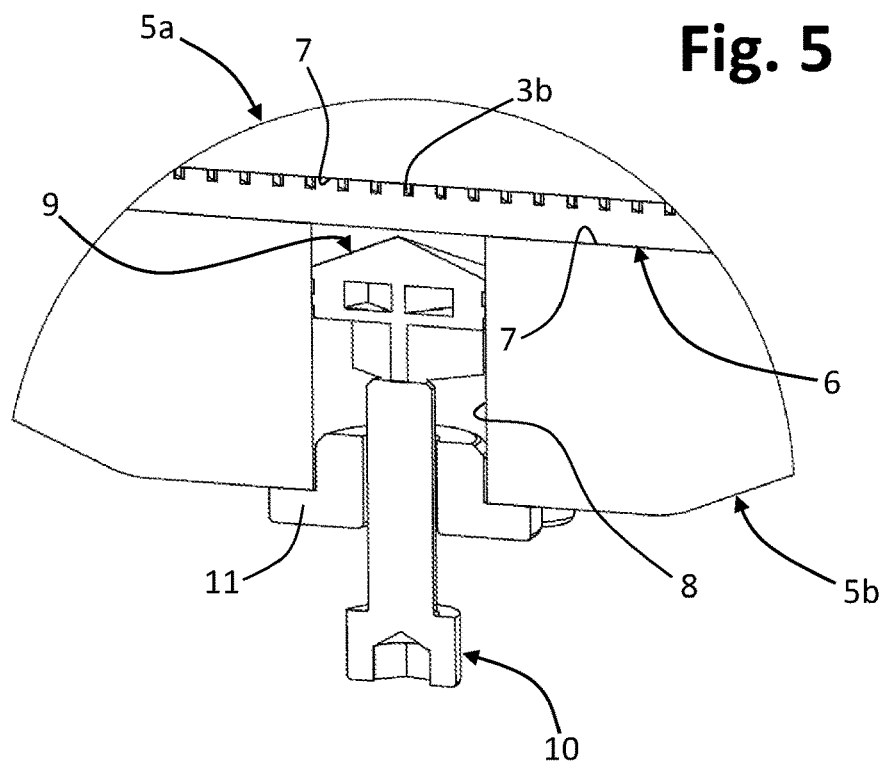
FIGS. 5 and 6 are partial and schematic sections of a disposable device of the apparatus of FIG. 1, in two different operative conditions.
Figure 6:
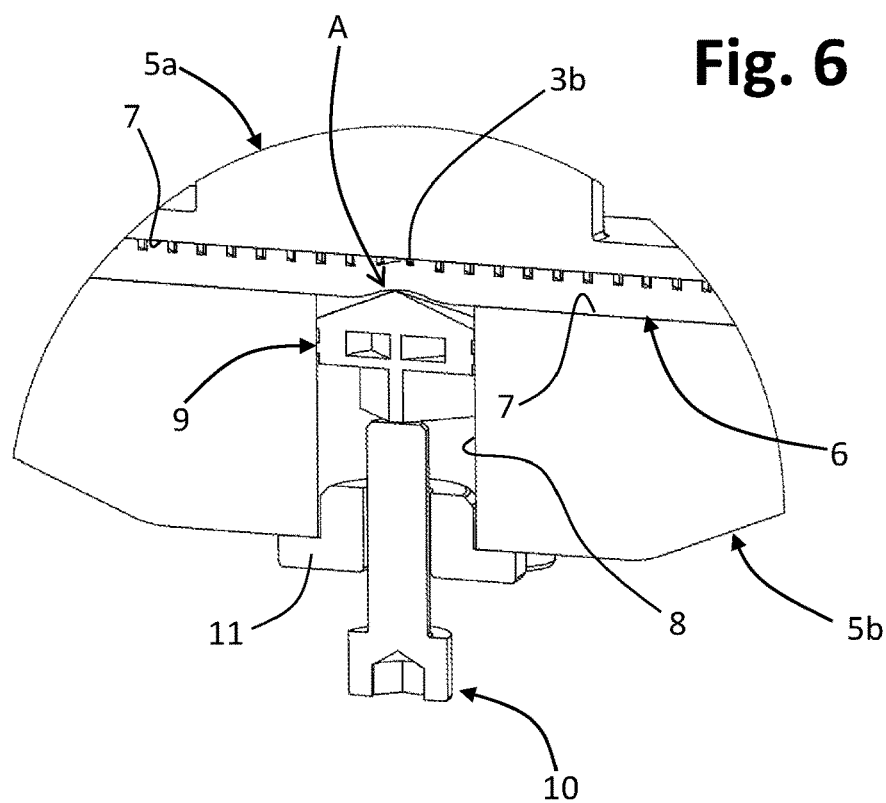

As observable, particularly from FIGS. 5 and 6, the duct body 6 is housed between the two parts 5a and 5b of the supporting body 5, on the bottom of the seat 7 of part 5b, so that its upper surface is at contact with the bottom of the seat 7 of part 5a: in this way, a respective portion of the duct 3 is defined between said bottom and the recessed parts 6a, 6b of the body 6.

As observable for example in FIGS. 4-6, in various embodiments the adjustment arrangement comprises at least one passage 8 of the supporting body 5, which is susceptible of at least partly receiving a movable adjustment member, operable to cause a controlled variation or reduction of a passage section of the duct 3. For such purpose, the passage 8 has an end facing at least one part of the deformable portion of the duct body 6 (which is entirely deformable, in the exemplified case) and it preferably extends in a generally transverse direction with respect to the duct body 6.

In the exemplified embodiment, the passage 8 is defined in the body part 5b and the adjusting member 9, whose top part faces towards the surface of the body 6 opposite to the one having the recessed parts 6a, 6b, is slidably housed therein. In the example, the adjustment arrangement further comprises an actuating or adjusting element 10, represented herein by a screw element, engaged in the threading of a through hole 11a (FIG. 4) of a closing element 11 which is in turn screwed or driven into the passage 8; the actuating or adjusting element 10 may possibly be directly coupled to the body 5 in a displaceable fashion.

As observable, the adjusting member 9 is susceptible of assuming a plurality of operative positions, to which different passage sections of the duct 3 correspond. FIG. 5 shows an inoperative position of the adjustment arrangement, in which the position or screwing degree of the actuating element 10 on the body 5, particularly in the corresponding threaded hole of the closing element 11, is such that the top part of the adjusting member 9 does not cause any deformation of the duct body 6, and thus any deformation of the part of the duct 3 defined by the crossed canalisations 6b.

FIG. 6 instead shows a position of the element 10 such that the member 9 presses the body 6 against the bottom of the seat 7 of the body part 5b: in such condition, the adjustment arrangement, through the member 9 thereof, causes a local deformation of the body 6, i.e. a compression of a portion thereof, in the area indicated with A: this causes a reduction of the passage cross-section of the corresponding canalizations 6b, and hence a reduction of a passage section of the duct 3. Preferably, such compression is suitable to cause a variation of the dimensions of the parts in relief that define the canalizations 6b, which become smaller in the height direction or in the compression direction and preferably widen in a direction substantially orthogonal to compression direction: in this way a reduction is caused—both in terms of height and width—of the canalizations 6b, at least in a part of the area A.

In various embodiments, the apparatus 1 comprises a structure for supporting at least one of the containers for containing the adipose tissue. For example, returning to FIGS. 1 and 2, in case of the embodiment illustrated up to now, a support, indicated as a whole with 12, preferably made using rigid material, for example plastic material, is associated to the part 5a of the body 5. The support 12 defines two through seats 12a—substantially cylindrical-shaped herein—for positioning the two syringes 4 in such a way that the corresponding tips 4a can be coupled to the two ends or attachments 3a and 3b of the duct 3. In the example, the support 12 is configured as a distinct part with respect to the supporting body 5, fixed in an intermediate part 12b thereof to a bracket 5c defined by the body 5a, so that the syringes 4 are oriented substantially orthogonal to the supporting body 5. However, the scope of the invention does not exclude the case of a support 12 integrally made with one of the parts 5a, 5b of the body 5.

The operation of the apparatus of FIGS. 1-6 is very simple.

The adipose tissue is introduced into one of the two syringes 4, preferably together with a saline solution, for example in a 1:1 ratio in volume. The capacity of the syringes 4 obviously depend on the amount of lipoaspirate or tissue to be treated: possible capacities are for example 10, 20, 60 and 140 ml for respectively treating approximately 5, 10, 30, 70 ml of the adipose tissue.

By actuating the syringes 4 manually or in an automated fashion, the adipose tissue is transferred from one syringe to the other syringe for a number of times, for example 4-5 times, with the adjustment arrangement of the disposable device 2 in the inoperative condition thereof, as shown in FIG. 5 (obviously, the repeated passage of the tissue between the syringes could also be obtained by actuating only one of them, in thrust mode initially and then in the suction mode, but this is less convenient).

Subsequently, by acting on the adjustment element 10 a first local deformation of the duct body 6 is caused, thus causing a narrowing of a passage section thereof, as outlined previously and as schematically illustrated in FIG. 6. For example, the element 10 may be operated—manually or in automated manner—so as to determine a predefined reduction of the passage section of the duct 3 in the deformation area A, for example approximately one half thereof. Subsequently, there is carried out a new transfer, possibly repeated, of the adipose tissue from one syringe 4 to another. The adjustment member 10 may be subsequently operated again, so as to narrow the passage section further, for example up to a position of minimum passage of the duct 3 in the area A, and the passage is repeated from one syringe to the other again.

Preferably, at the end of the repeated passages from one syringe to another through the duct 3, the apparatus 1 is oriented vertically in the direction represented in FIGS. 1 and 2. In this way, in the destination syringe, the content sediments separating (from the top to the bottom) into oil released by the tissue, tissue containing the cells of interest and saline solution dirty with bloody. By activating the destination syringe, the saline solution dirty with blood is conveyed into the other syringe, subsequently removed and discarded.

In case it is desired to carry out a further washing of the preparation, one may introduce a fresh saline solution, for example by replacing the removed syringe with one containing a the saline solution and causing at least one passage of the disgregated tissue from the aforementioned destination syringe to the one containing the fresh saline solution, with the duct 3 dilated, i.e. in the inoperative position of the adjustment arrangement (FIG. 4), and with a manual agitation to facilitate the mixing between the tissue and the solution. This is followed by a further sedimentation step and subsequent separation of the dirty saline solution, similar to the description above.

Operating as indicated allows obtaining the following results washing the treated tissue using the saline solution;

disgregation of the adipose tissues as to make it injectable using needles having small diameters;

enriching with younger cells, by breaking the larger adipocytes; the already differentiated adipose tissue cells are larger and thus easier to disgregate in presence of sufficient shear stress which is obtained through the passages in the duct; on the other hand, the younger cells are preserved with a still high differentiated potential;

maintaining the stroma in the obtained fat cell clusters, i.e. micronization of fat without damaging the cells forming the clusters; it is preferable to obtain a disgregation at the level of cell aggregates and not of single cells: the organised structure of the small cell structure actually allows a quicker regeneration of the tissue with respect to the cultivation of single cells.

Thus, this leads to obtaining—in absence of "relevant manipulations"—a preparation including adult stem cells, progenitors of endothelial cells, leukocytes and pericytes.

FIGS. 7-13 refer to a second possible embodiment of an apparatus according to the invention.

Figure 7:
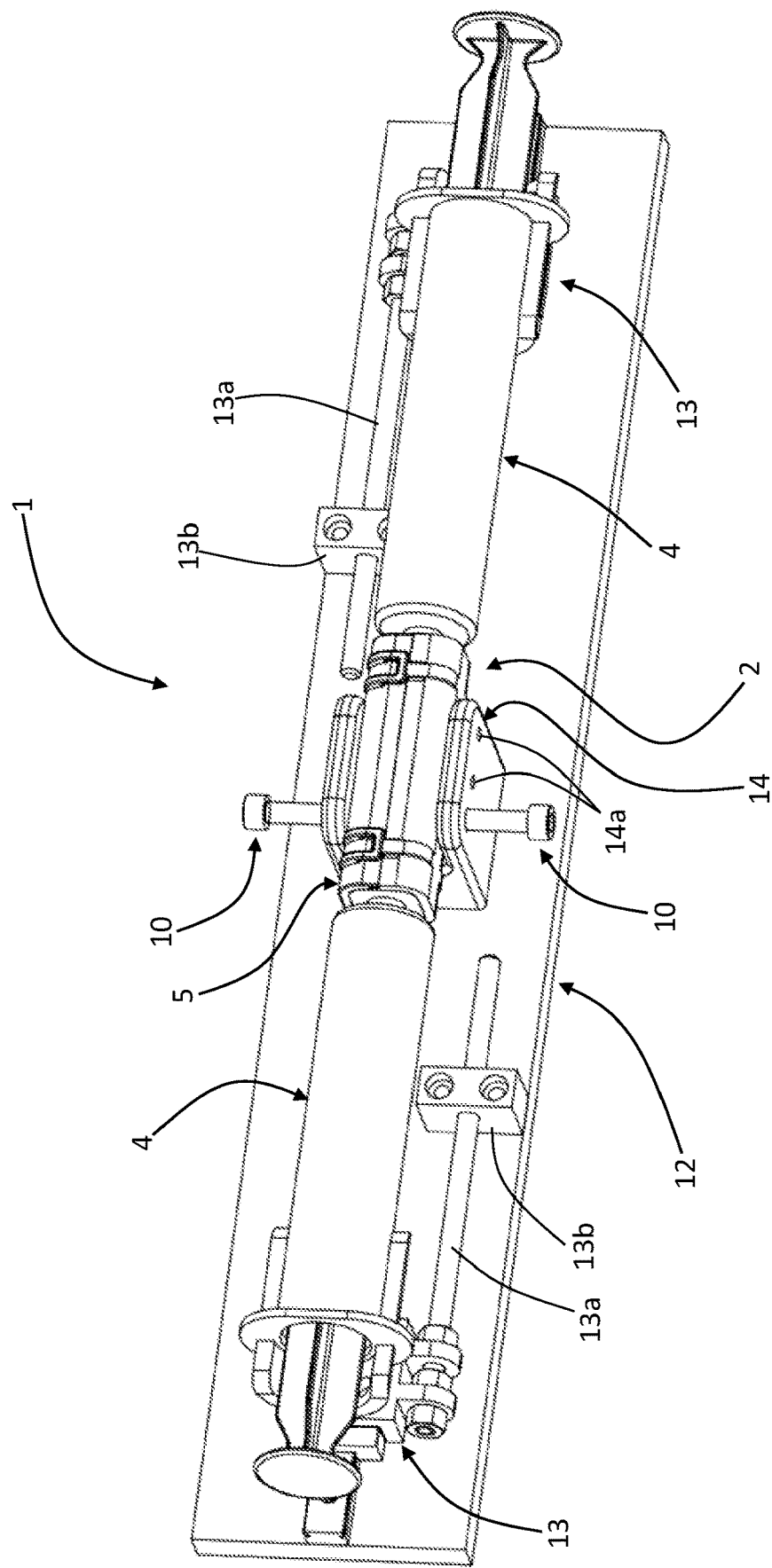
FIG. 7 is a schematic perspective view of a further possible embodiment of an apparatus for disgregating an adipose tissue according to the present invention.
Figure 8:
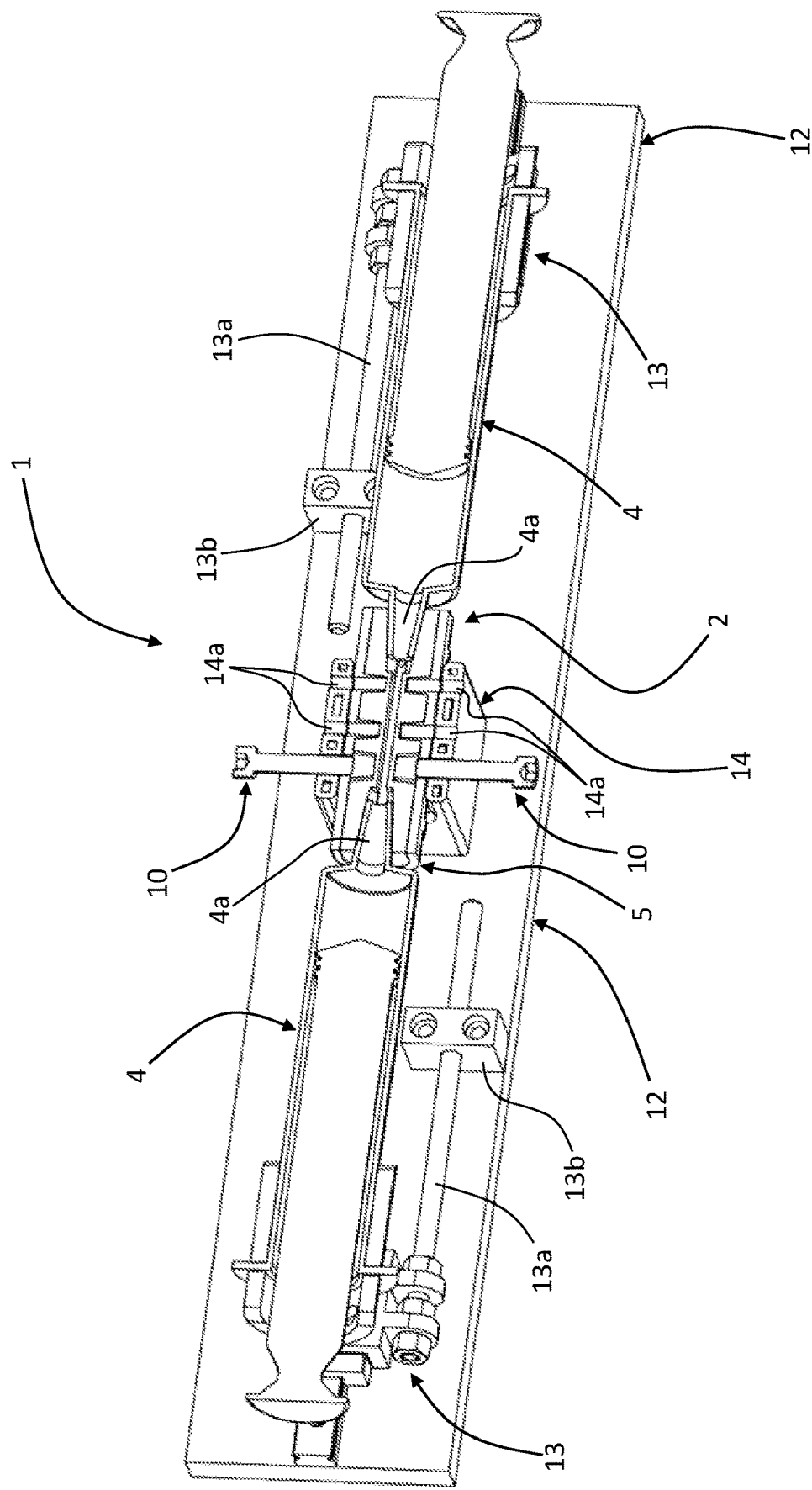
FIG. 8 is a schematic section of the apparatus of FIG. 1.
Figure 9:
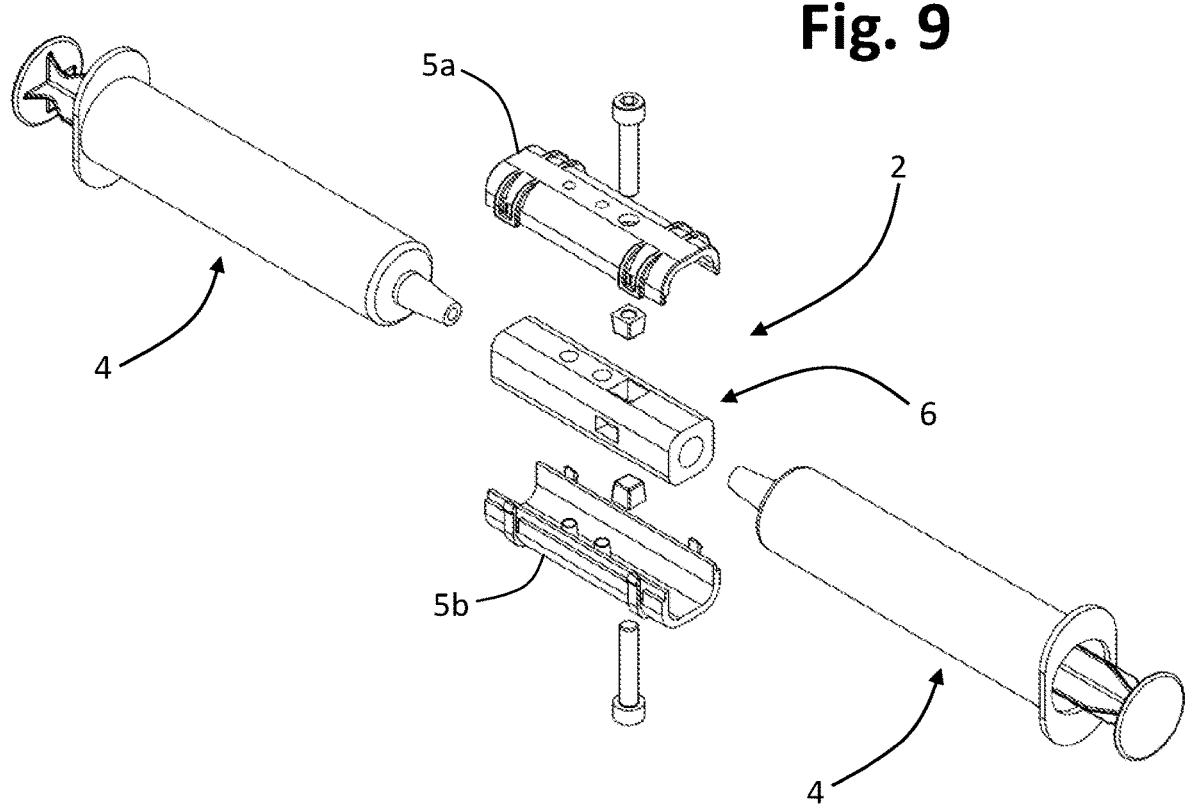
FIG. 9 is an exploded schematic view of some components of the apparatus of FIG. 7.
Figure 10:
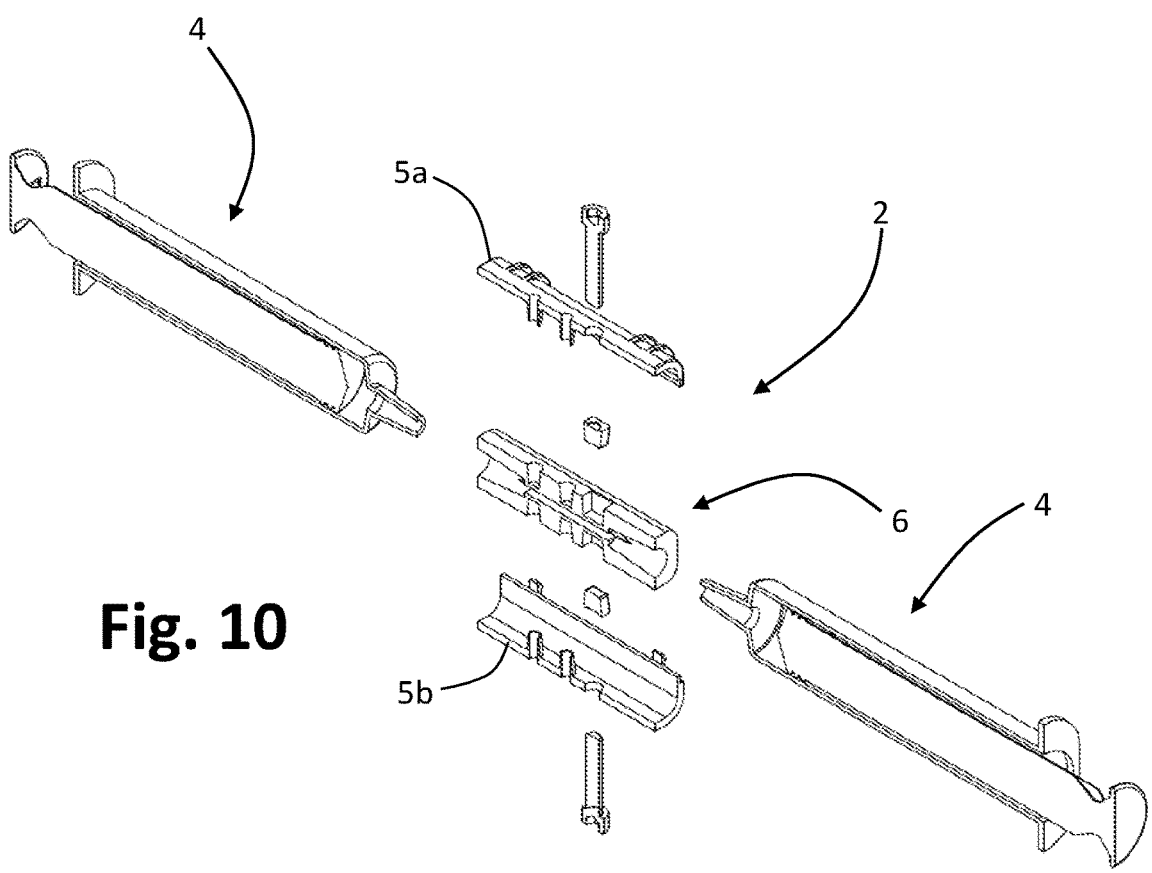
FIG. 10 is a sectional exploded view of the components of FIG. 9.

Initially referring to FIGS. 7 and 8, even in this embodiment the apparatus 1 includes a supporting structure, herein including a base 12 substantially plate-like with associated supports 13, preferably moveable, for positioning and/or adjusting the collecting devices 4, preferably represented by syringes.

In various embodiments, the supports 13 may be of the moveable or adjustable type, to enable the use of collecting devices of different dimensions. In the non-limiting example, the supports 13 adjustable in position have a corresponding seat—herein substantially cradle-like or, more generally, at least in part complementary to the casing of the corresponding collecting device—for receiving a corresponding portion of the syringe 4. In the example, the position of each support 13 is adjustable in the axial longitudinal direction of the base 12 or, more generally, of the inlet/outlet opening 4*a* of the syringe, through a threaded rod 13*a* engaged in a threaded hole of a corresponding block 13*b* associated to the base 12.

Clearly, the base 12 may be provided with adjustable supporting systems different from the exemplified one, to enable the support of syringes 4 of different dimensions, even in terms of different diameter; to this end, at least part of the supports 13 may be of the replaceable type, such as the seat or cradle complementary to the corresponding syringe 4, preferably provided with mutual quick coupling and/or decoupling means.

In an area thereof intermediate to the base 12 there is associated a member 14 for positioning and/or supporting a disposable device 2. In the considered example, the member 14 is configured as a substantially U-shaped seat or bracket, with two parallel or opposite arms between which there can be positioned the disposable device 2, which is represented in different view in FIGS. 9-12.

Also in this embodiment the disposable device 2 has a respective supporting body 5, comprising at least two parts, preferably made of relatively rigid material, such as a polymer or a metal or an alloy or a thermoplastic and/or mouldable material, herein configured as shells 5*a* and 5*b* couplable to receive therebetween a duct body 6, which is longitudinally traversed by the duct 3.

In the example, the shells 5*a* and 5*b* are substantially U-shaped and they are provided with means for mutual coupling, particularly with a snap-coupling, for example comprising coupling teeth 5' and corresponding coupling seat or tabs 5" (FIG. 11). The shells could be even differently shaped with respect to the ones represented as an example, such as a semi-cylindrical or concave shaped and/or complementary to the duct body 6, and/or they could also be more than two.

In this case, the duct body 6 has a three-dimensional elongated shape, particularly substantially parallelepiped-shaped, even it can also be obtained substantially cylindrical or prismatic-shaped, or having any other shape suitable for the purpose. The body 6 is at least partly made of elastically yieldable material, so as to define the yieldable portion of the adjustment arrangement. Preferably, the body 6 is entirely made using such material, which is very preferably a polymer or a synthetic material, such as an elastomer or a silicone.

In the illustrated embodiment, the two opposite longitudinal ends of the body 6 are accessible at the two open sides of the body 5: in this way, in various embodiments, the two ends 3*a*, 3*b* of the duct 3—herein entirely defined by the body 6—may be shaped to directly define attachments for the hydraulic connection of the collecting devices, herein represented by the tips of the syringes 4, also exploiting the elasticity of the material forming the body 6.

In the example, for this purpose, the ends 3*a*, 3*b* of the duct 3 have a substantially frusto-conical shape, or a shape at least partly complementary to the hydraulic couplings 4*a* of the connecting devices 4.

In various embodiments, the adjustment arrangement comprises at least one blind seat or a similar area with a reduced thickness, which is defined in the duct body at a corresponding deformable portion, wherein such area or seat is susceptible to at least partly receive a corresponding movable adjustment member and preferably extends in a direction generally transverse or orthogonal to the duct body and/or to the axis of at least part of the corresponding duct for the adipose tissue. The duct body may also include two or more such seats, preferably opposite to each other, each designed to receive a corresponding adjusting member.

Such case is for example the one subject of the embodiment of the FIGS. 7-14, where the duct body 6 defines at least two blind seats or cavities 15 (in particular see FIGS. 12-14), generally mutually aligned to each other at opposite sides of the duct 3, each of said seats 15 receiving a corresponding adjusting member 9, herein configured as a prismatic-shaped block. As observable, the cavities 15 define respective areas of reduced thickness of the duct body 6, particularly to facilitate the deformation of the latter aimed at attaining a variation of the passage section of the duct 3.

Preferably, to each adjusting member 9 there is associated a corresponding actuating or adjusting element 10, which passes through a hole 8 of the corresponding shell 5*a* or 5*b*. In various embodiments, the element 10 is substantially of the screw type, engaged in a threading of the corresponding hole 8. Alternatively, the holes 8 may be a smooth surface, while the threading which enables adjusting the position of the element 10, and thus the corresponding adjusting member 9, is defined in a hole of a supporting member of the disposable device, through which the element 10 passes through (for example see FIGS. 7-8, where the support member 14 has holes 14*a* for the passage of the adjustment elements 10).

In various embodiments, the supporting body and the duct body have coupling and/or positioning means, to ensure their mutual coupling and/or positioning. Such case is for example clearly visible in FIGS. 11-14, which show how the duct body 6 defines blind seats or cavities 16 susceptible to receive corresponding positioning elements 17, which project from the inner surfaces of the shells 5*a* and 5*b*. Preferably, there are provided for at least two cavities 16 in opposite parts of the body 6, as well as at least one element 17 in a corresponding position on each shell 5*a* and 5*b*. The cavities 16 and the elements 17 preferably have a substantially complementary profile, for example substantially frusto-conical, as in the exemplified case. Clearly, also this type of coupling is facilitated by the yieldability of the body 6. Additionally, or alternatively, the duct body 6 could define reliefs susceptible to be coupled with corresponding cavities or seats in the shells 5*a* and 5*b*.

In various embodiments, the duct body 6 may provide for further cavities, aimed at determining further thickness reductions in the walls of the ducts 3, so as to facilitate the deformation of the body thereof by one or more adjusting members 9. In such cases, in the body 6 there are preferably provided for two such cavities in opposite positions: in FIG. 11 one of such further cavities is indicated with 18.

In various embodiments, the duct body has at least one transparent portion and the supporting body comprises at least one optical detection passage, which extends in a direction transverse or orthogonal to the duct body and/or the axis of at least part of the corresponding duct for the tissue. The optical detection passage has a distal end facing a corresponding transparent portion of the duct body. In various embodiments, there are provided at least two optical detection passages in opposite positions in the duct body, preferably two pairs of opposite passages. In various embodiments, there are provided corresponding passages even in the supporting body, at the detection passages of the duct body, such as through holes (for example in the case of a supporting body made of opaque material or material impermeable to an optical or electromagnetic signal) or blind holes or seats in case of a supporting body at least partly made of transparent material or material permeable to an optical or electromagnetic signal.

In various embodiments, the functions of the aforementioned coupling and/or positioning means on the one hand, and the optical detection passages, on the other, may be combined to each other, i.e. obtained using the same elements. In other embodiments instead, the coupling and/or positioning means of the disposable device are configured as elements functionally separated from the optical detection passages.

In the represented case, for example, the previously mentioned coupling means represented by the cavities 16 and by the elements 17 are also exploited as optical detection passages. For example, referring to FIGS. 11-14, it should be assumed that the body 6 is entirely made of transparent material: as observable, the cavities 16 obtain blind passages, whose distal end or bottom 16*a* (FIGS. 13-14) obtains a transparent wall of the duct 3, similarly to the seats 15 for the adjusting members 9. Still with reference to the illustrated example, the elements 17 projecting from the shells 5*a*, 5*b* are axially hollow, so that—through them—the transparent bottom 16*a* of the cavities 16 is directly viewable.

Preferably, the elements 17 at least partly engage the cavity 16, in particular so as to maintain the shape of such cavity and/or keep the optical passages well open even in the presence of stresses of deformations of the body 6, such as deformation or throttling of the body 6 near the cavities 16. As mentioned, in other embodiments, elements functionally similar to those indicated with 17 could have a blind cavity, instead of a through cavity, with a bottom transparent to light or permeable to the detection electromagnetic radiation.

In other embodiments, the supporting body 5 alone attains optical detection transparent seats or walls, sealed with respect to the fluid in the duct 3. For example, some embodiments provide for one or more elements 17 with a blind cavity (i.e. with a closing bottom thereof) made in a supporting body 5 made of transparent material, and the duct body 6 is provided with one or more corresponding through holes 16 (i.e. without the distal end or bottom 16*a*), in which such element 17 is coupled sealingly; in such a case, the optical detection is carried out through the aforementioned bottom of the blind cavities of the elements 17.

Preferably, at least two optical detection passages 16-17 are in a position substantially coaxial to each other, in opposite parts of the device 2, and a transparent portion of the duct body 6 extends therebetween. In this way, in various embodiments, in or at the hollow elements 17 there may be positioned suitable sensor means, such as a transmitter and a receiver of an optical signal or an electromagnetic radiation, preferably mutually opposite and/or coaxial with the duct 3 interposed, adapted to detect variations of said signal, for example, variations of transmittance or any other optical characteristics of the fluid that flows from time to time through the duct 3, said variations being useful to provide process indications, for example as explained hereinafter. In various embodiments, for this purpose, at an element 17 or passage of the body 5 that replaces it, and thus the corresponding cavity 16, there may be arranged a photo-emitter, and a photo-detector may be arranged at the diametrically opposite element 17 and cavity 16. Just like in the exemplified case, it is also possible to provide for several optical detection passages along the duct, to improve the detection quality.

In other embodiments, at least one transmitter and one receiver of optical or electromagnetic signal are set side by side or differently angled with respect to the duct 3, so as to detect variations in at least one from among reflection, reflectance, refraction, diffraction and signal spectrum, determined by the fluid which flows through the duct.

The use of a sensor system of the indicated type may be combined with the apparatus 1 both when the syringes 4 thereof are actuated manually (in which case there will for example be provided a suitable electronic detection device, to which the sensor system is connected to), and when the apparatus is positioned on a suitable equipment for the automatic actuation of the syringes, including the aforementioned sensor system (such case will be exemplified hereinafter); alternatively, in case of manual use, the hollow elements 17 or the body passages 5 that replace them may be used for a direct display by the operator, or they may house suitable display means, such as warning lights or optical guides made of transparent material.

Figure 13:
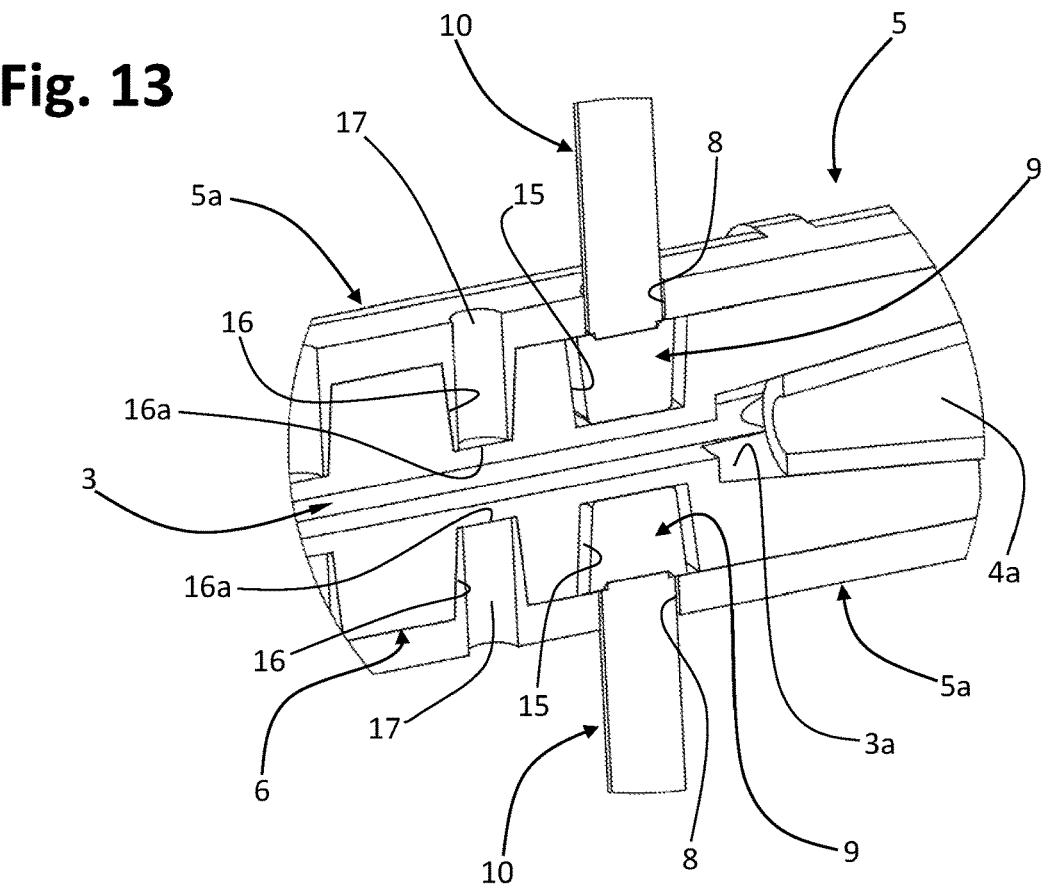
FIGS. 13 and 14 are partial and schematic sections of a portion of the device of FIG. 11, in two different operative conditions.
Figure 14:
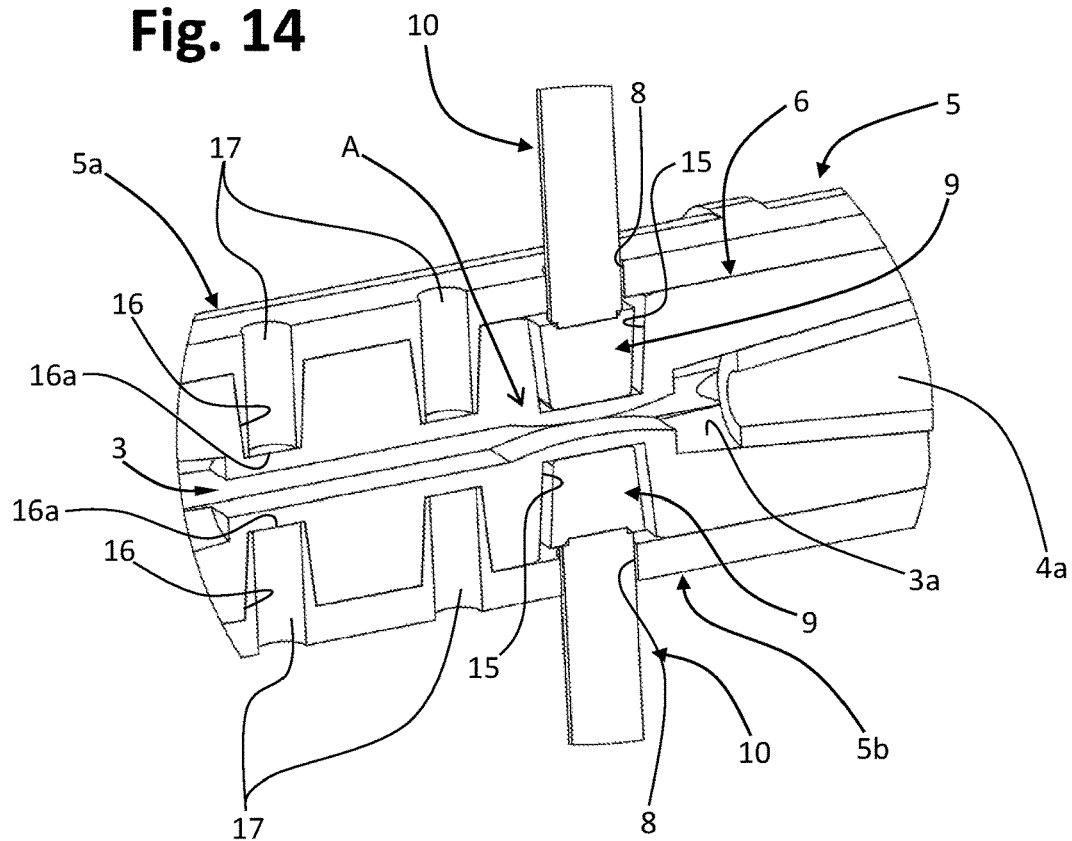

The operation of the apparatus of FIGS. 7-14 occurs substantially in the same way as described previously, with the difference that in this case the variation of the passage section of the duct 3 may be obtained by acting on at least one of two distinct adjusting members 9 and/or corresponding actuating elements 10, preferably arranged in opposite positions with respect to the duct. FIG. 13 shows the inoperative condition of the adjustment arrangement, in which the position of the adjusting elements 10 in the corresponding threaded hole 8 is such that the opposite top part of the adjusting members 9 does not cause any deformation of the duct body 6, and thus of the part of the duct 3 defined between the seats 15. FIG. 14 instead shows a position of the elements 10 such that the members 9 press the body 6 from opposite sides: in such condition, the adjustment arrangement causes a local deformation of the body 6, in the area indicated with A, i.e. a compression of a portion thereof comprised between the members 9, thus causing a reduction of the passage section of the duct 3.

In various embodiments, at least one portion of the duct defined in the duct body has a substantially polygonal internal profile, preferably substantially quadrangular. Such characteristic is advantageous for a better control of the reduction of the passage section for the adipose tissue in the device 2, particularly when the adjustment arrangement of the device includes two adjusting members operating in opposite positions, such as for example in the case of the embodiment of FIGS. 7-14, where the part of the duct 3 comprised between the two ends 3*a*, 3*b* thereof is substantially quadrangular-shaped.

FIGS. 15-28 schematically illustrate a further possible embodiment of an apparatus according to the invention.

Also in this case, the apparatus includes a disposable device 2, having a respective supporting body 5. In this case, the duct body 6 comprises at least two pieces of a flexible and deformable tube, indicated with $6_1$ and $6_2$, and has two ends 3*a* and 3*b* which protrude from the body 5, having or defining respective attachments for the syringes 4. The tube 6 has an internal diameter preferably comprised between 2 and 5 millimetres, very preferably comprised between 3 and 4 mm, or a shape with a cross-section preferably comprised between 3 and 20 square millimetres, very preferably comprised between 7 and 12 square millimetres.

In various embodiments, the disposable device comprises an auxiliary duct, for introducing the adipose tissue and/or the saline solution into a main duct of the disposable device which connects at least two handling and/or collecting devices, such as two syringes.

In an embodiment of this type, the aforementioned auxiliary duct has an inlet and an outlet which is connected to the main duct in an intermediate position to the two ends thereof which are connected to the syringe. In addition, preferably, between the inlet and the outlet of the auxiliary duct there is provided at least one from among a pre-treatment device, such as a mechanical filtering device, and a unidirectional valve.

An embodiment of this type is included in the device 2 of FIGS. 15-28, wherein the aforementioned auxiliary duct is indicated as a whole with 20, the pre-treatment device (simply referred to as filter, hereinafter) is indicated with 21 and the unidirectional valve is indicated with 22. Preferably, also the duct 20 includes a plurality of pieces of tube $20_1$, $20_2$, to enable an easy connection along the duct itself of the filter 21 and of the valve 22. The aforementioned pieces of tube may be however at least partly obtained as a single piece, for example obtained through moulding, particularly of a polymer or an elastomer. Preferably, the body of the valve 22 defines the inlet 20a of the auxiliary duct, while the outlet thereof is preferably defined by a fitting for connecting to the main duct 3.

Figure 15:
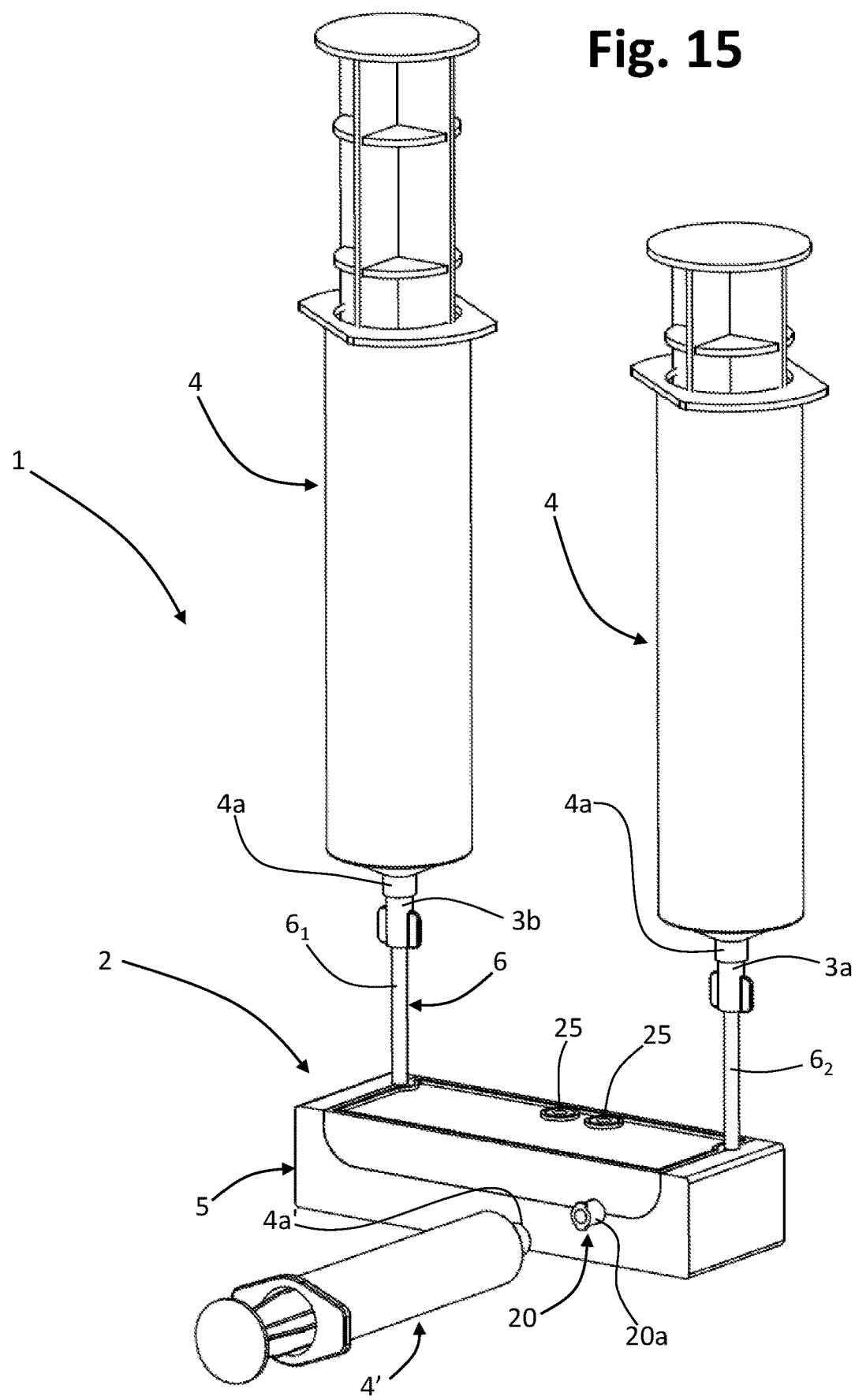
FIG. 15 is a schematic perspective view of a further possible embodiment of an apparatus for disgregating an adipose tissue according to the present invention.
Figure 16:
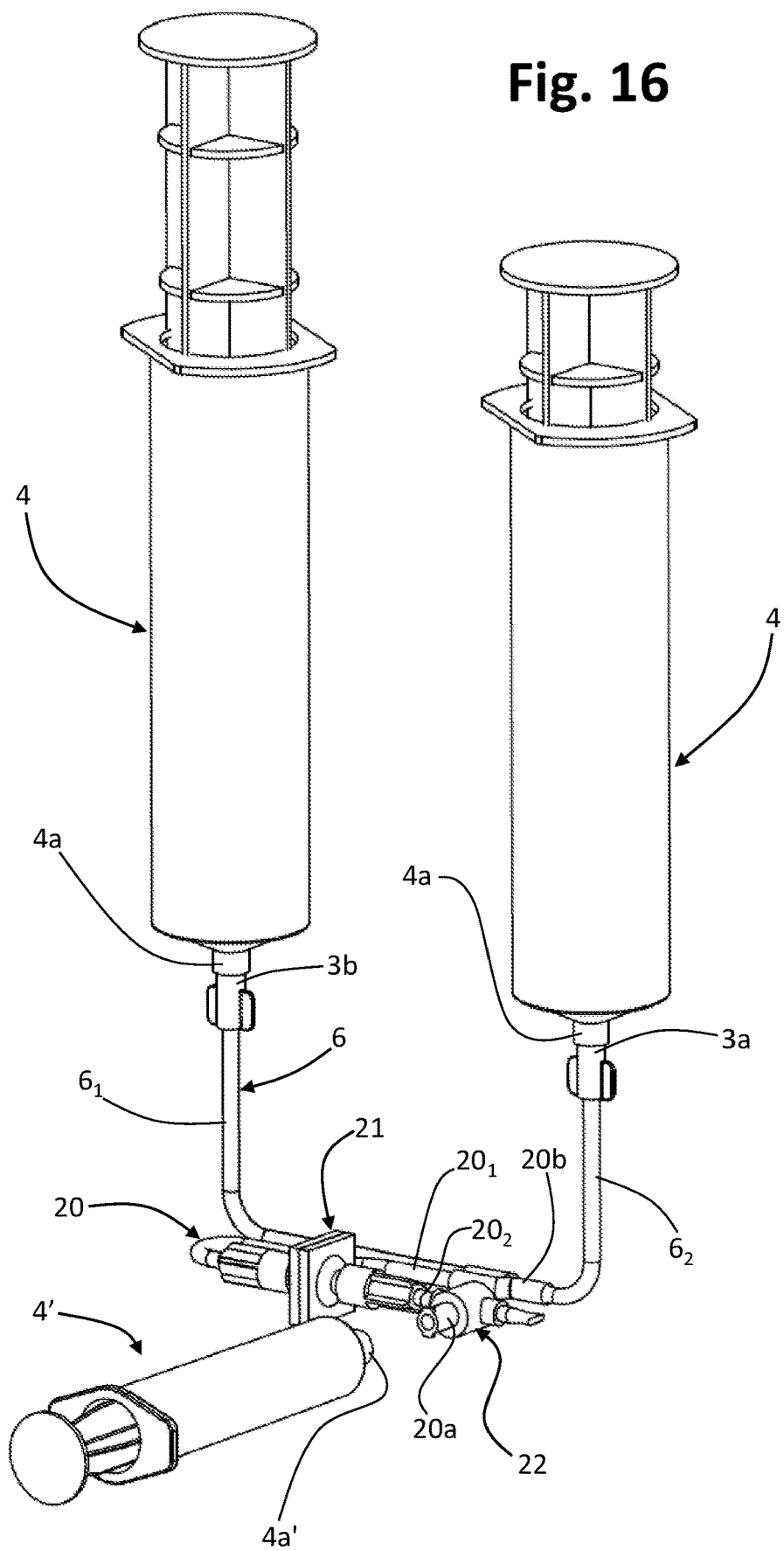
FIG. 16 is a schematic perspective view of the apparatus of FIG. 15, with a casing of a corresponding disposable device removed.
Figure 17:
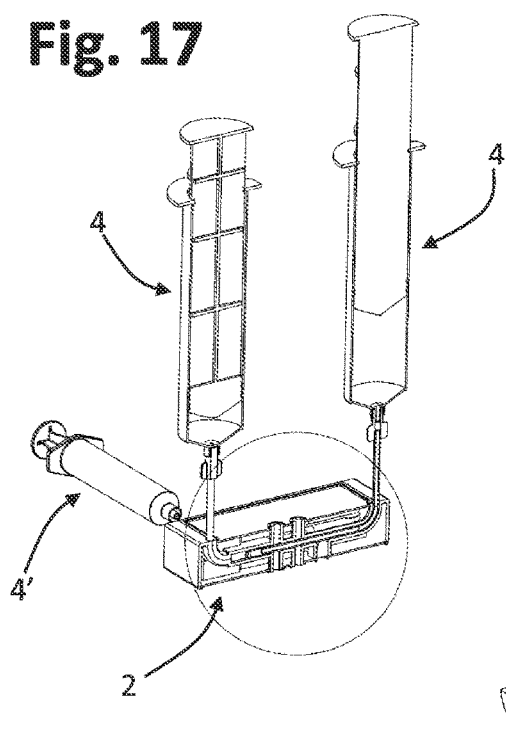
FIGS. 17, 18, 19 and 20 are sectional perspective views of the apparatus of FIG. 15.
Figure 18:
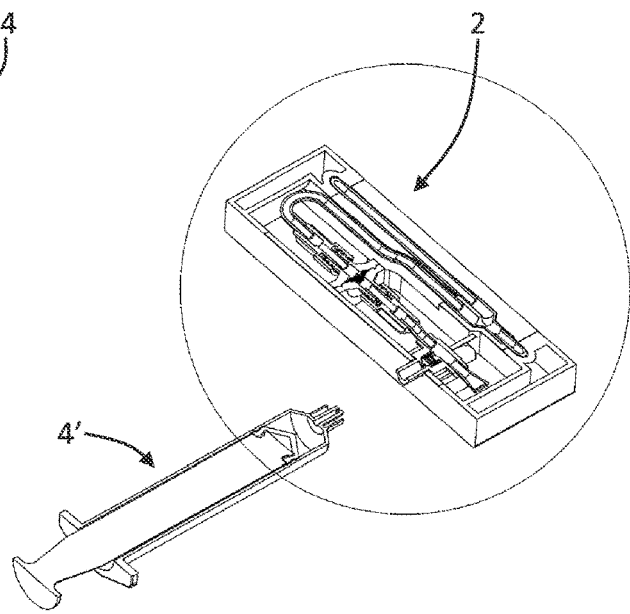
Figure 19:
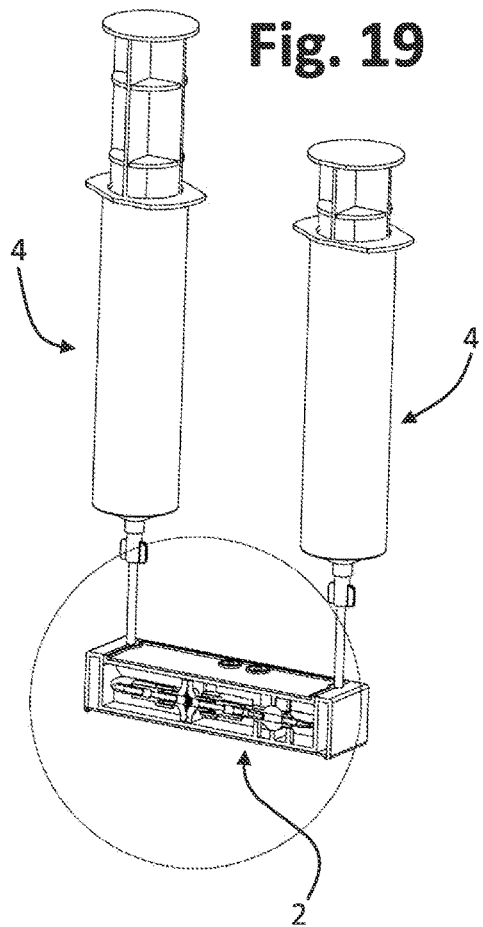
Figure 20:
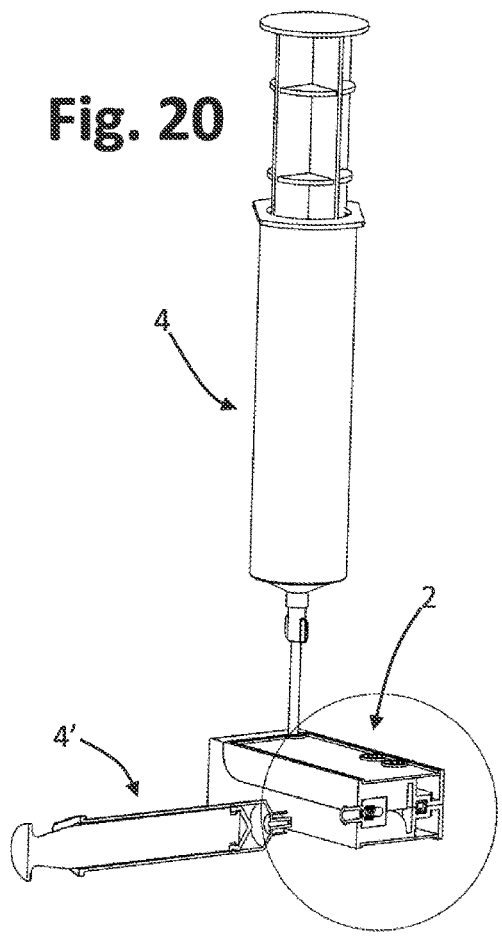

As observable particularly from FIG. 15, the inlet 20a of the auxiliary duct 20 protrudes towards the outside of the supporting body 5 and it is preferably shaped to enable the connection of an attachment or tip of a further device or syringe 4', used for the introduction of the adipose tissue and/or of saline solution into the device 2. The outlet of the auxiliary duct 20 is instead connected in an intermediate position of the main duct 3, through a fitting, preferably a substantially Y-shaped fitting or a fitting of any other suitable shape, indicated with 20b for example in FIGS. 16, 22 and 25.

In this embodiment, the supporting body 5 comprises two main parts 5a, 5b mutually coupled and defining suitable seats for positioning at least one from among the ducts 3 and 20, the filter 21 and the valve 22; some of these seats are indicated with 23 in FIGS. 21-24. The supporting body 5 also comprises an upper cover body 5d and a lower cover body 5e; alternatively, or additionally, there may be provided a further external casing, for example comprising an upper body and a lower body, adapted to at least partly enclose the bodies 5a and 5b.

Figure 21:
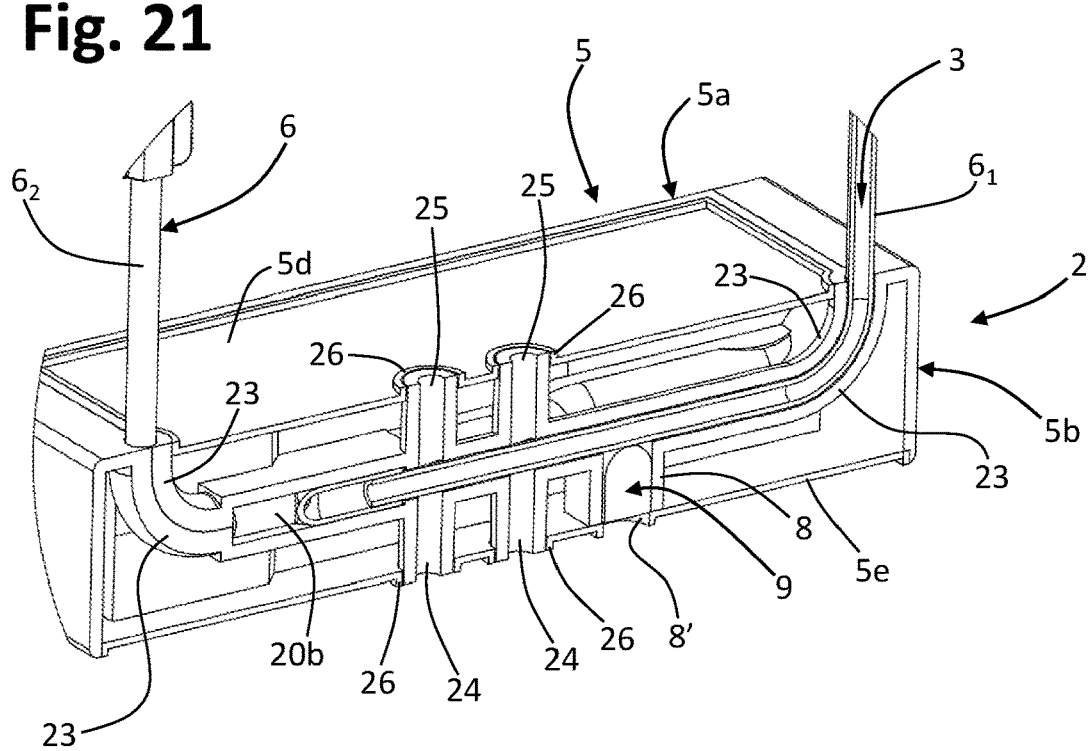
FIGS. 21, 22, 23 and 24 are enlarged details of FIGS. 17, 18, 19 and 20, respectively.
Figure 22:
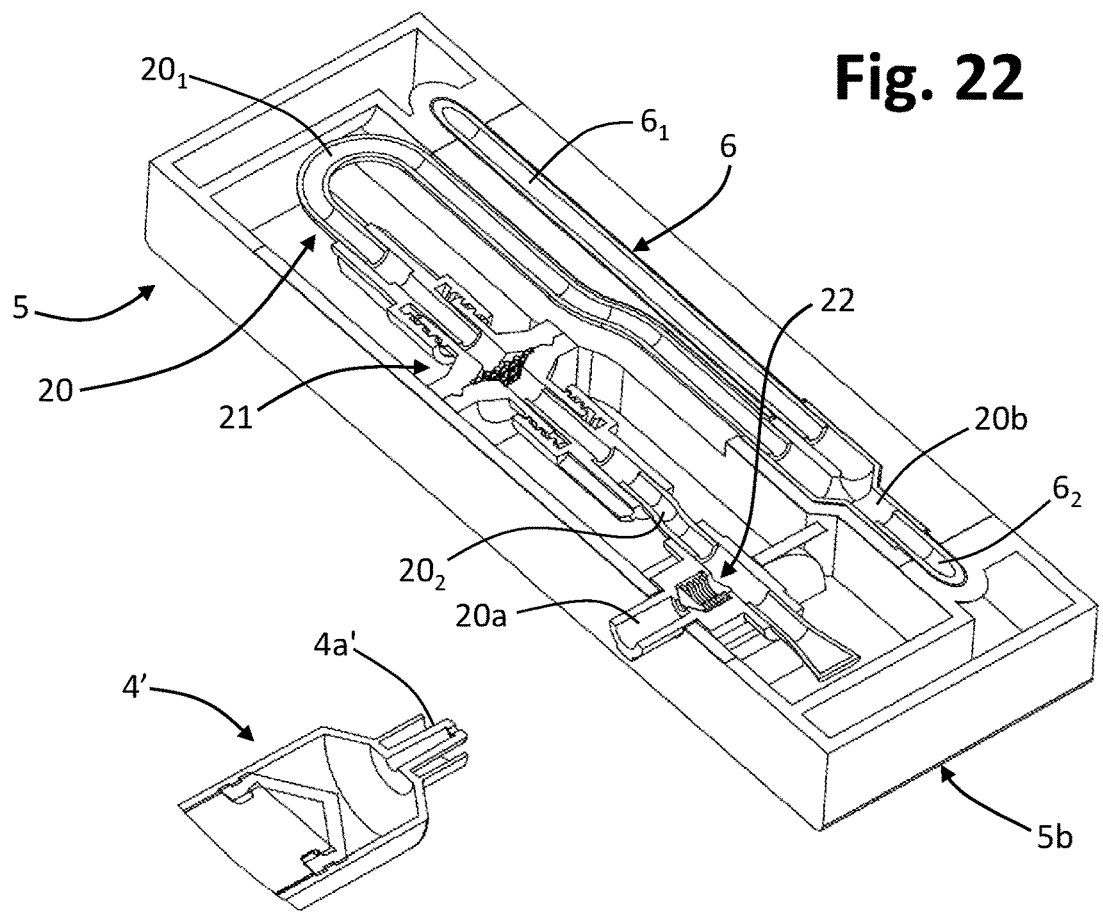
Figure 23:
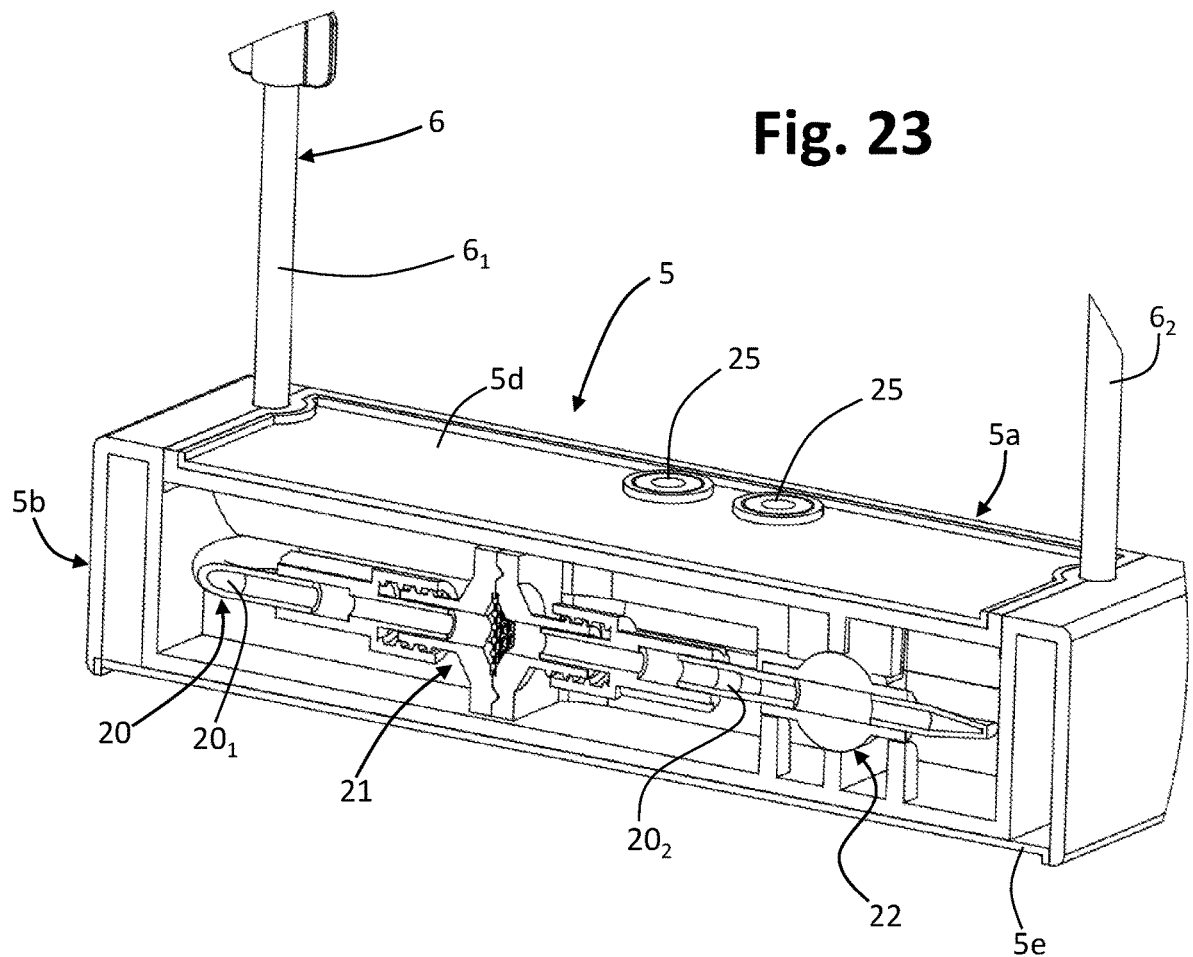
Figure 24:
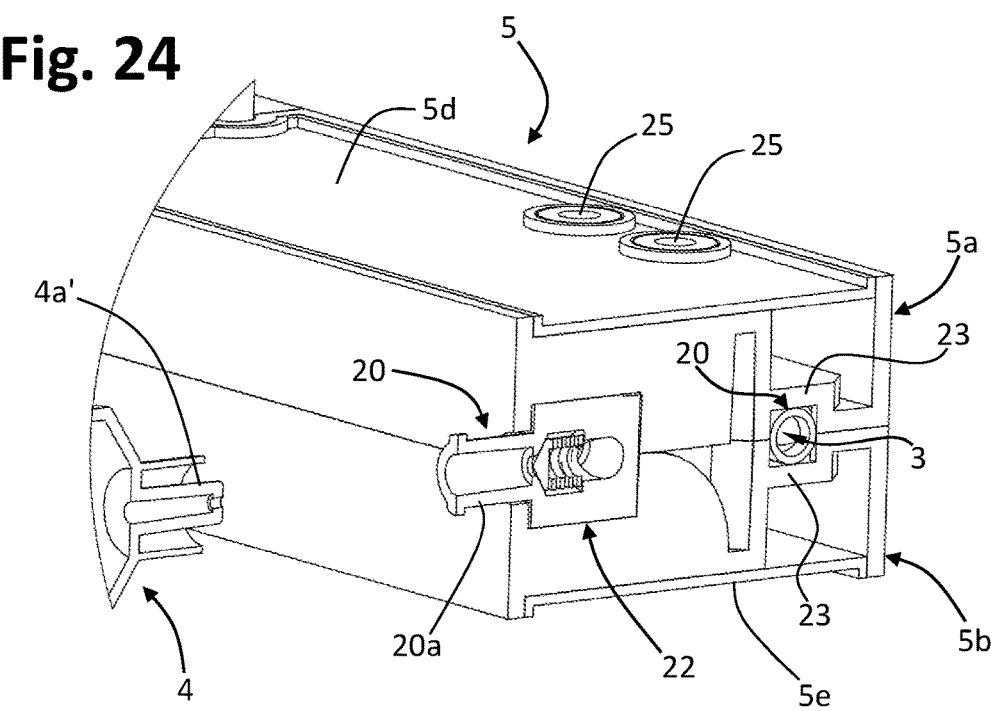

In various embodiments, at least part of the duct 3, herein represented by the section of tube $6_1$, is transparent and the supporting body 5 (or at least one from among the bodies 5a, 5b, 5d, 5e) defines or integrates optical detection passages. With particular reference to FIG. 21, it should be observed that the body parts 5a and 5b define, in substantially opposite positions, respective detection passages 24 and 25, in opposite positions with respect to the transparent section of tube $6_1$. The covers 5d and 5e are purposely provided with respective openings 26, which enable access to the passages 24 and 25. As previously indicated, the passages 24 and 25 are used to enable detection of at least one optical characteristic of the fluid flowing through the duct 3: to this end, the apparatus 1 may be used in combination with an equipment provided with an optical sensor system, preferably also designed to actuate in an automated way the syringes 4 and/or the adjustment arrangement of the device 2.

Also in this case, the adjustment arrangement includes an adjusting member 9, preferably belonging to the disposable device 2 (however, as explained hereinafter, in other embodiments one such member could be part of an equipment for the automated actuation of the apparatus 1).

To this end, one of the body parts—part 5a herein—defines a corresponding passage 8 for the guiding and the sliding of the member 9, and the corresponding cover—the cover 5e herein—has an opening 8' for enabling actuation of the member 9, as clearly observable for example in FIG. 21.

Figure 25:
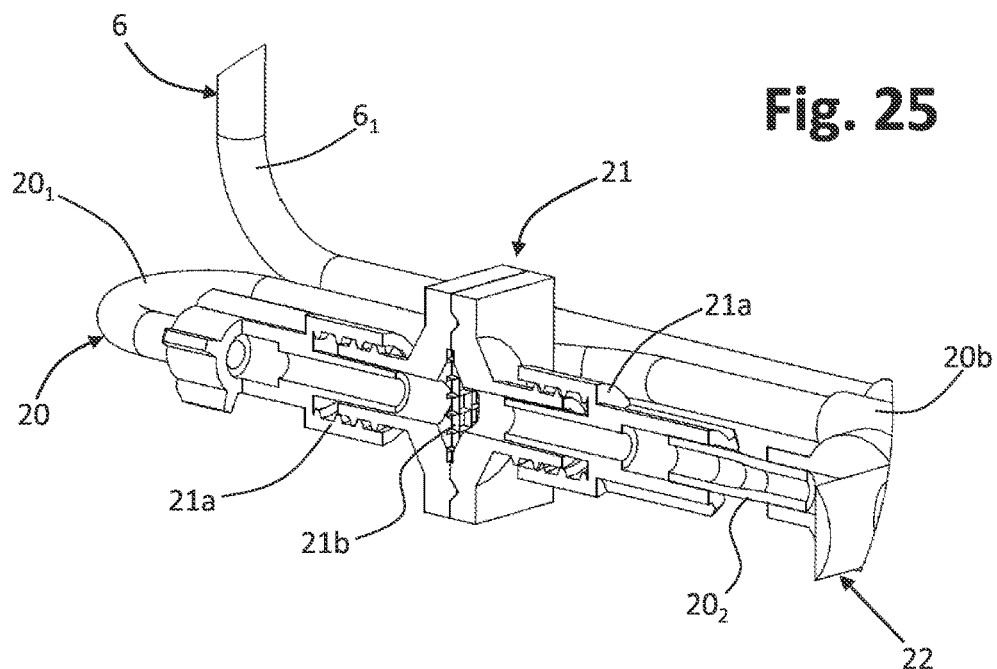
FIG. 25 is a sectional, partial and schematic view, of internal ducts of a disposable device of the apparatus of FIG. 15.

As observable in FIG. 25, the pre-treatment device or filter 21 is preferably provided with corresponding attachments 21a, for connection between the tube sections $20_1$ and $20_2$ and it may be advantageously obtained through a mesh or blades structure 21b, possibly sharp meshes or blades for retaining and/or facilitating a first disgregation of the larger adipose tissue, when it is introduced into the device 2.

The dimension of the passages defined by the meshes 21b is preferably comprised between about 0.5 and 2 mm. In particular, the dimension of the passages of the mesh is greater than at least one adjustment dimension or height of the duct 3 of the device 2 which can be obtained through the adjusting member 9, so as to be able to carry out a further finer treatment for disgregating the pre-treated adipose tissue.

The filter 21 and the unidirectional valve 22 may be obtained according to a known technique.

In this embodiment, the adipose tissue is introduced into the disposable device 2 through the syringe 4', for example also containing a saline solution. The tip 4a' of the syringe 4' is connected to the inlet 20a of the auxiliary duct 20, which can be conveniently configured as a Luer lock attachment. The tissue initially traverses the unidirectional valve 22 and then the filter 21, where then largest parts are retained and/or a first disgregation of the tissue occurs. Thus, the partly disgregated tissue proceeds into the auxiliary duct 20 until it reaches—through the fitting which provides the outlet 20b—in the duct 3, particularly in the piece of tube $6_2$. In this way the tissue reaches the inside of the corresponding syringe 4, causing the plunger thereof to recede.

Figure 26:
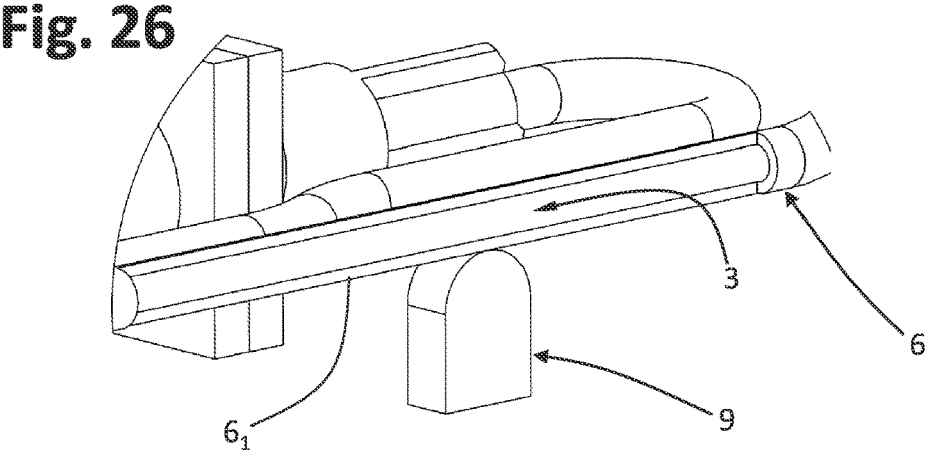
FIGS. 26 and 27 are partial sectional views of a duct of a disposable device of the apparatus of FIG. 15, in two different operative conditions.
Figure 27:
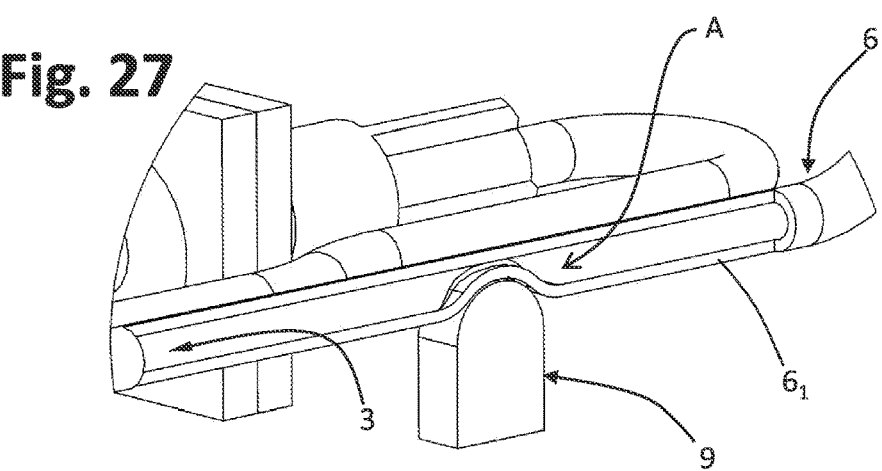

Subsequently, there follows the generation of repeated and alternated actuations of the two syringes 4: in such step, the presence of the unidirectional valve 22 prevents the tissue pushed from time to time between the two syringes 4 from exiting through the inlet 20a of the auxiliary duct 20. After one or more passages between the syringes 4 the narrowing of the passage section of the duct 3 is carried out, at the area in which the adjusting member 9 is located, and the process proceeds similarly to the previous description regarding the preceding embodiments. As can be imagined, also in this case, the variable extent of the axial displacement of the member 9 causes a corresponding local deformation of the piece of tube $6_1$, i.e. the variable reduction of the passage section thereof. FIG. 26 shows the inoperative condition of the adjustment arrangement, in which the position of the member 9 is such that the top part thereof does not cause any deformation of the piece of tube $6_1$. Conversely, FIG. 27 shows an adjustment position such that the member 9 causes a localised crushing of the piece $6_1$, in the area indicated with A, i.e. a reduction of the passage section of the duct 3.

As mentioned, the apparatus of FIGS. 15-27 is particularly designed for use in combination with an automated equipment. However, in possible variant embodiments, the same apparatus may—through simple modifications—be prearranged for manual actuation, for example by associating an actuation or adjustment element of the type previously indicated with 10, to the adjusting member 9.

Figure 28:
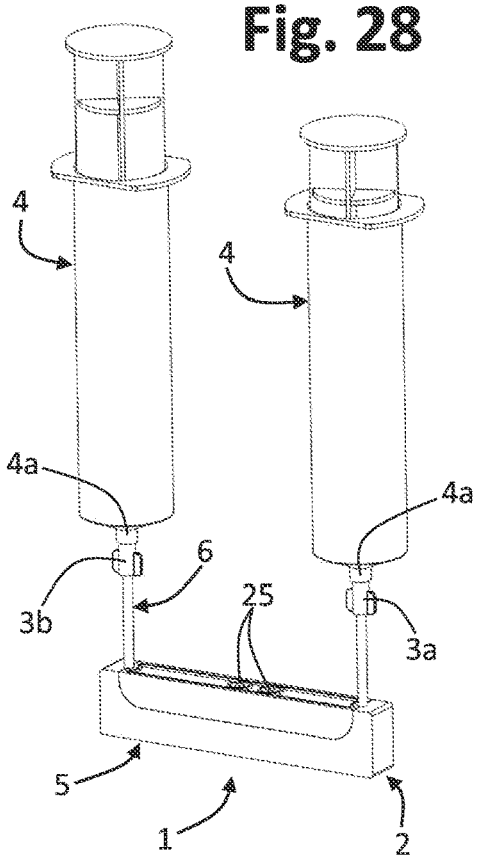
FIG. 28 is a schematic perspective view of a further possible embodiment of an apparatus for disgregating an adipose tissue according to the present invention.
Figure 29:
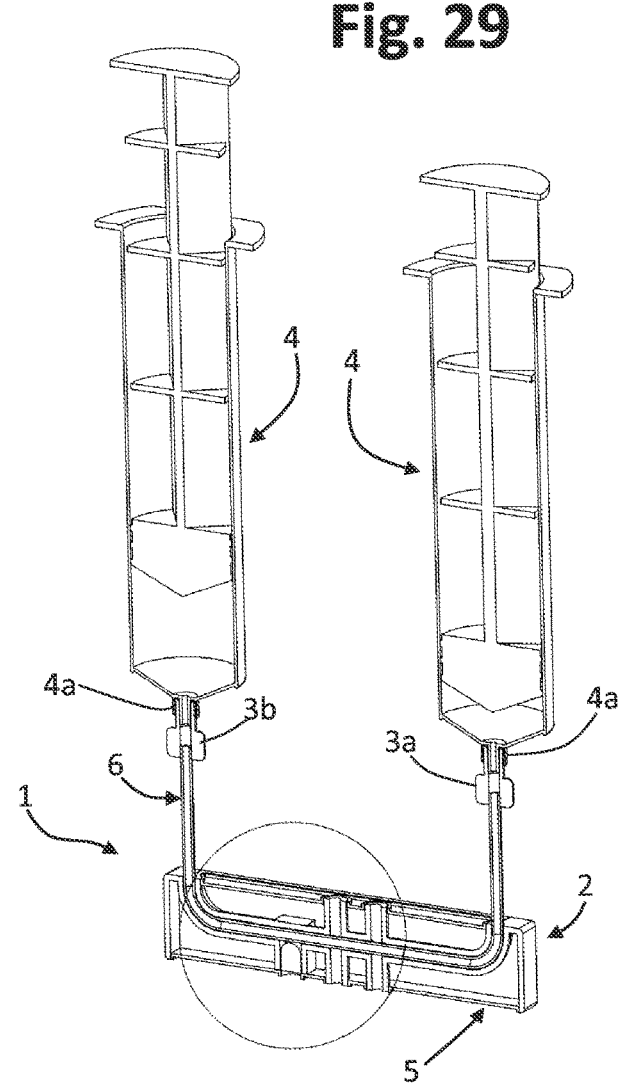
FIG. 29 is a schematic section of the apparatus of FIG. 28.
Figure 30:
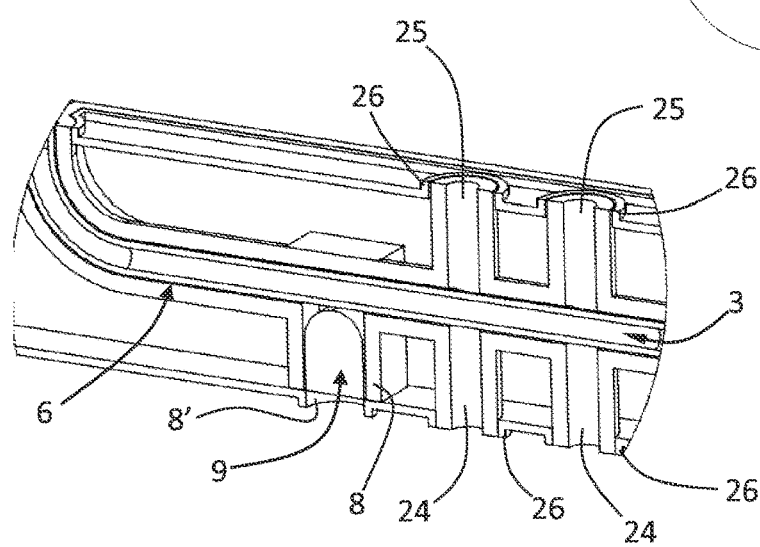
FIG. 30 is a detail of FIG. 29.

FIGS. 28-30 refer to an embodiment conceptually similar to that of FIGS. 15-27, but distinguished by the absence of the auxiliary duct with the associated filter 21 and unidirectional valve 22. Also the apparatus 1 of FIGS. 28-30 is particularly designed for use on an automated equipment, but the same may be easily prearranged for manual actuation, similarly to what has been said regarding the apparatus of FIGS. 15-27.

FIGS. 31-37 partly and schematically illustrate a possible embodiment of an equipment for the automatic management of an apparatus according to the invention.

Figure 31:
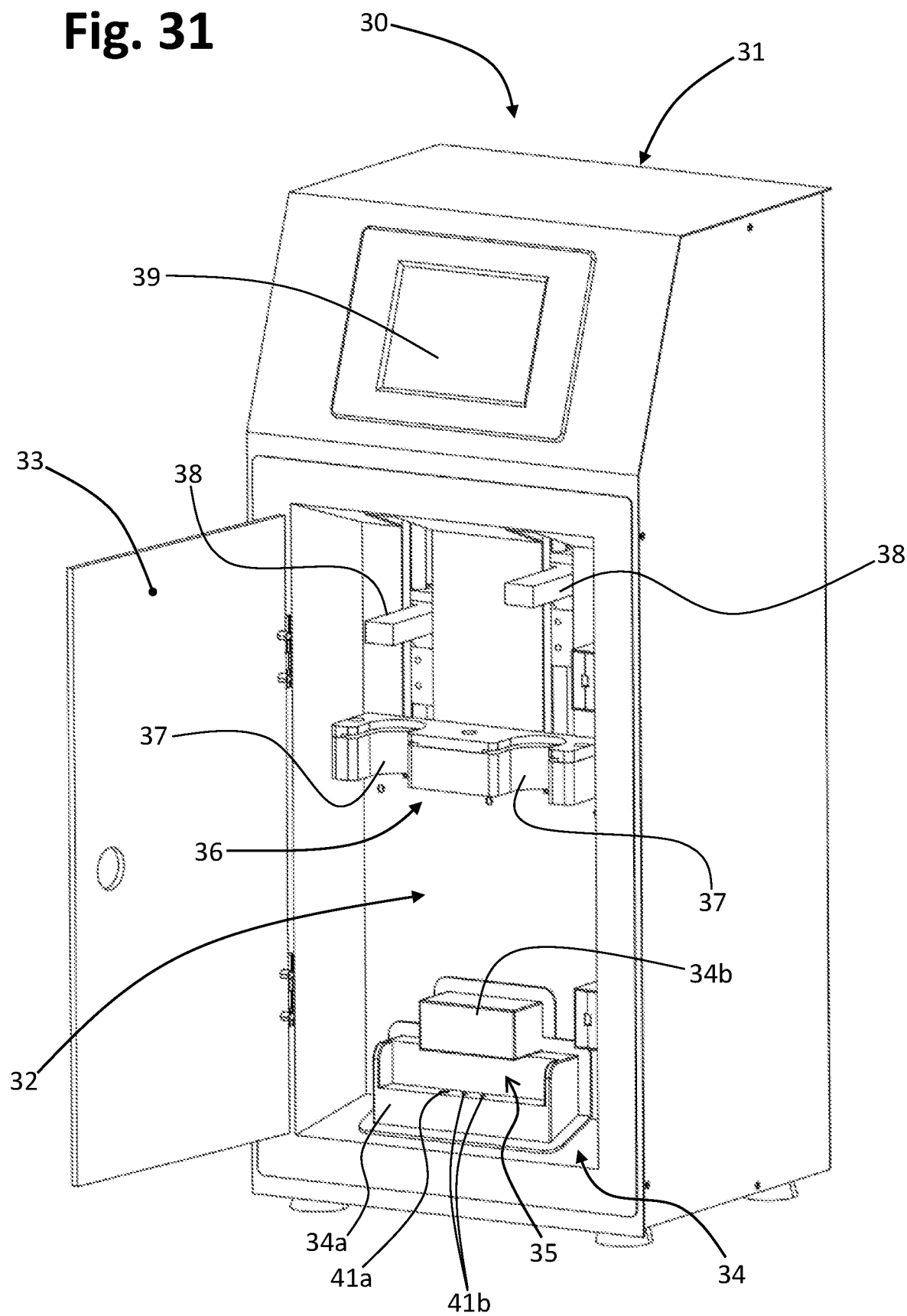
FIG. 31 is a schematic perspective view of an equipment for the automated actuation of an apparatus according to the invention.

Referring firstly to FIG. 31, the equipment—indicated as a whole with 30—has a load-bearing structure 31, in which there can be positioned an apparatus 1 (FIGS. 32-34 and 36 show an apparatus according to FIGS. 28-30, but in the illustrated case the equipment 30 is also capable of actuating an apparatus according to FIGS. 15-27). To this end, the structure 31 may define a housing compartment or space 32, which can be possibly closed using a corresponding door 33, associated to the load-bearing structure 31.

At a wall of the structure 31, herein in the compartment 32, there is a first support arrangement 34, defining a seat 35 for positioning the disposable device of the apparatus, as well as a second support arrangement 36, defining seats 37 for positioning the syringes 4, herein designed for operating in vertical position.

In general terms, the equipment comprises a first actuation system, which includes two moveable actuation members 38, configured to operate the handling members of the two collecting devices 4, herein represented by the plungers of the two syringes 4 (also see FIG. 32), so as to cause the flow of the adipose tissue through the duct of the disposable device, between the devices or syringes 4.

In addition, the equipment comprises a second actuation system, which includes at least one second moveable actuation member, described hereinafter, configured to operate the adjustment arrangement of the disposable device, so as to cause the aforementioned reduction of the passage section of the duct thereof.

The equipment also comprises a control system, configured to control at least the first and the second actuation arrangements in a coordinated fashion, for the purposes described previously (one or more passages of the adipose tissue in the duct, syringe actuation speed, reduction of the passage section of the duct, new passage/s, possible further reduction of the passage section, etcetera). Preferably, the control system includes a system for detecting characteristics of the fluid, preferably an optical detection system, as mentioned previously, for the detection of at least one characteristic of a fluid that flows in the duct of the disposable device. In the example, the control system comprises a user interface 39, for example including a touch screen display, adapted to receive controls and/or settings from a user.

Figure 33:
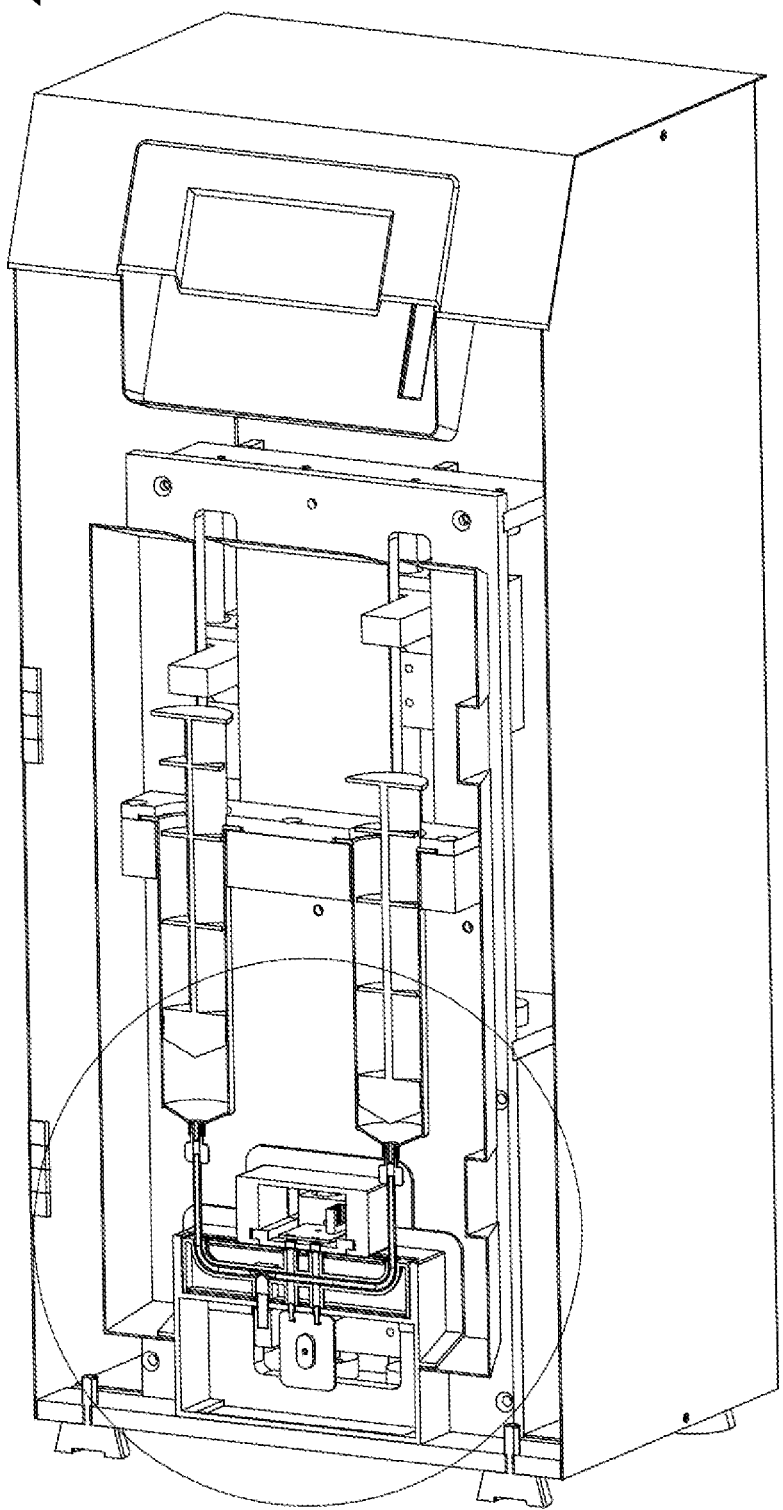
FIGS. 33, 34 and 35 are sectional views of the equipment of FIG. 32.
Figure 34:
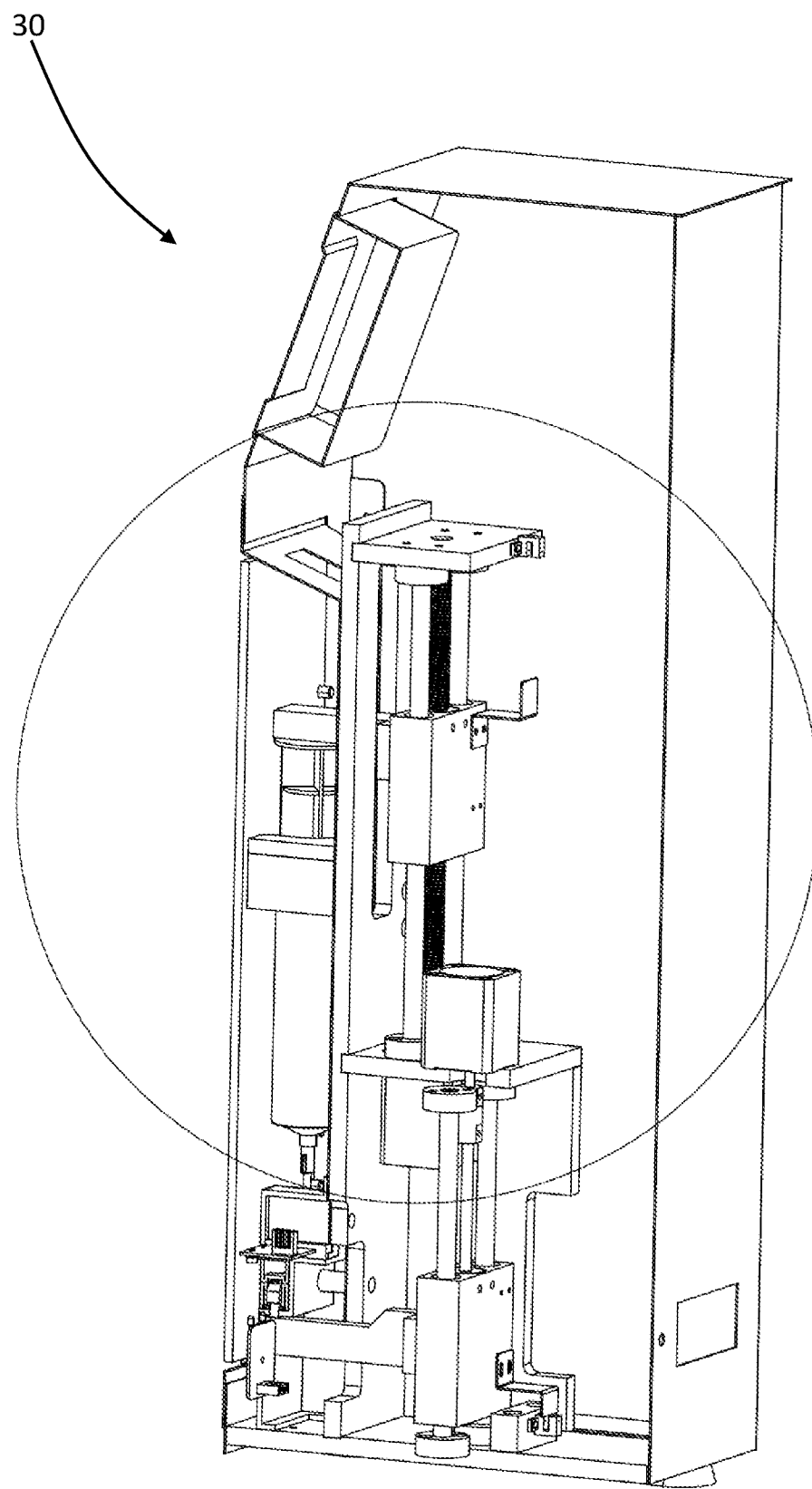
Figure 36:
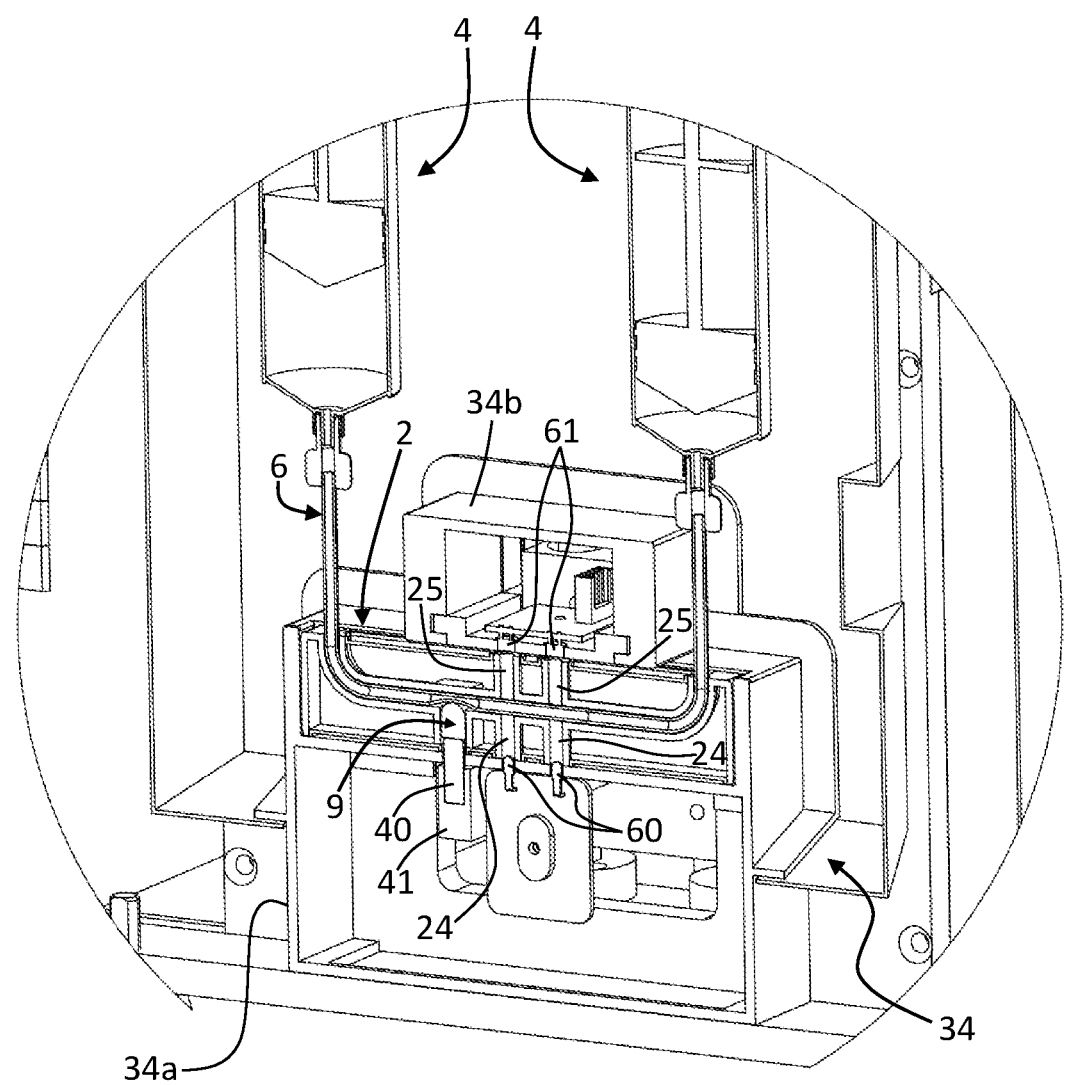
FIGS. 36, 37 and 38 are enlarged details of FIGS. 33, 34 and 35, respectively.

As observable particularly in FIG. 33 and in the corresponding detail of FIG. 36, at the support arrangement 34 there is moveably mounted an actuation element 40, designed to cause the variation of the position of the adjusting member 9 of the disposable device 2. In the example, the actuation element 40 is mounted in a lower portion 34a of the arrangement 34, which also includes an upper portion 34b, such two portions 34a and 34b defining seats 35 between them (FIG. 31).

An upper wall of the portion 34a, defining a bottom of the seat 35, has a hole 41a (FIG. 31), through which the element 40 is moveable.

In various embodiments, the element 40 is moved by means of a corresponding actuation system, for example using at least one electrical or hydraulic or pneumatic actuator.

Figure 35:
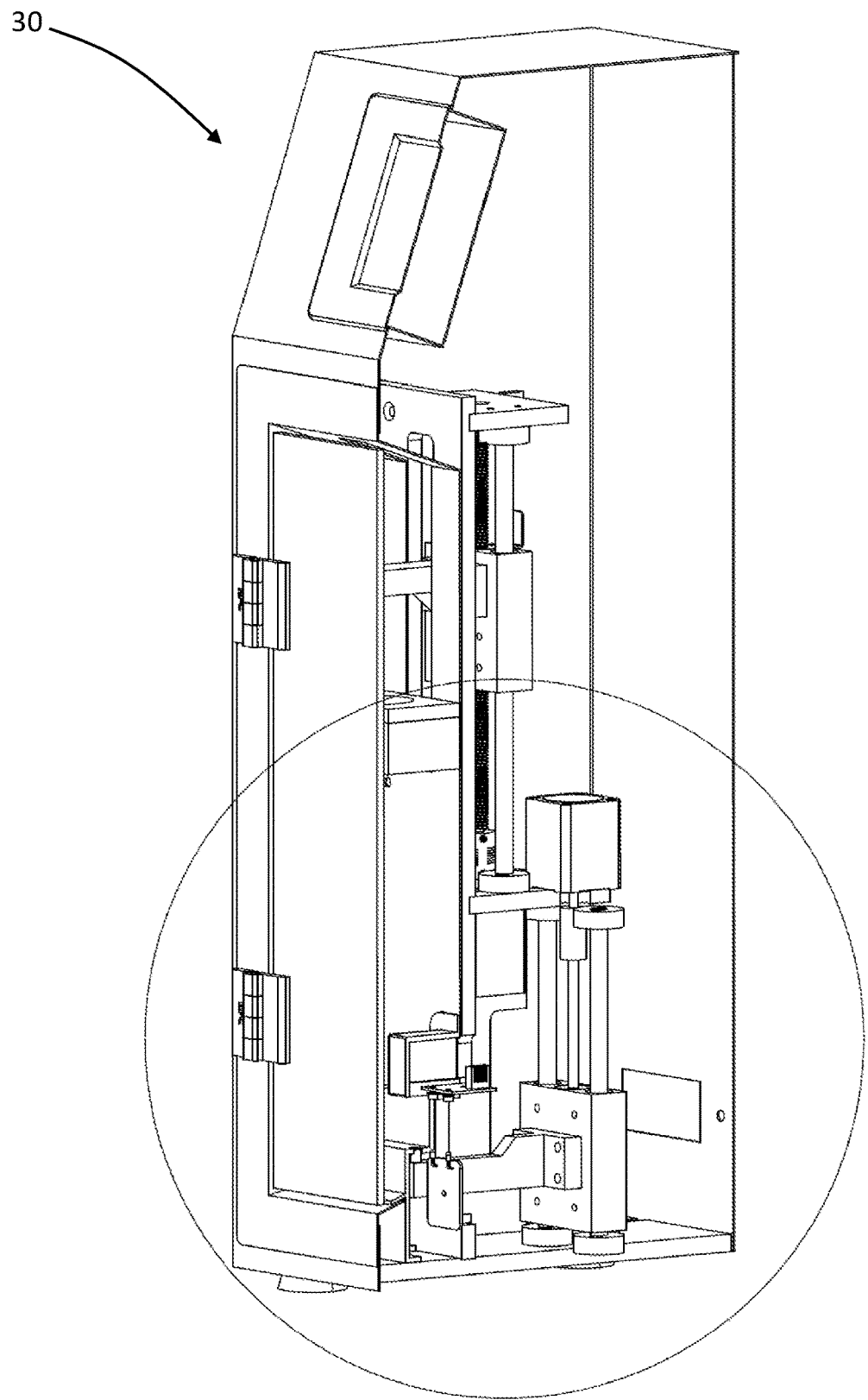
Figure 38:
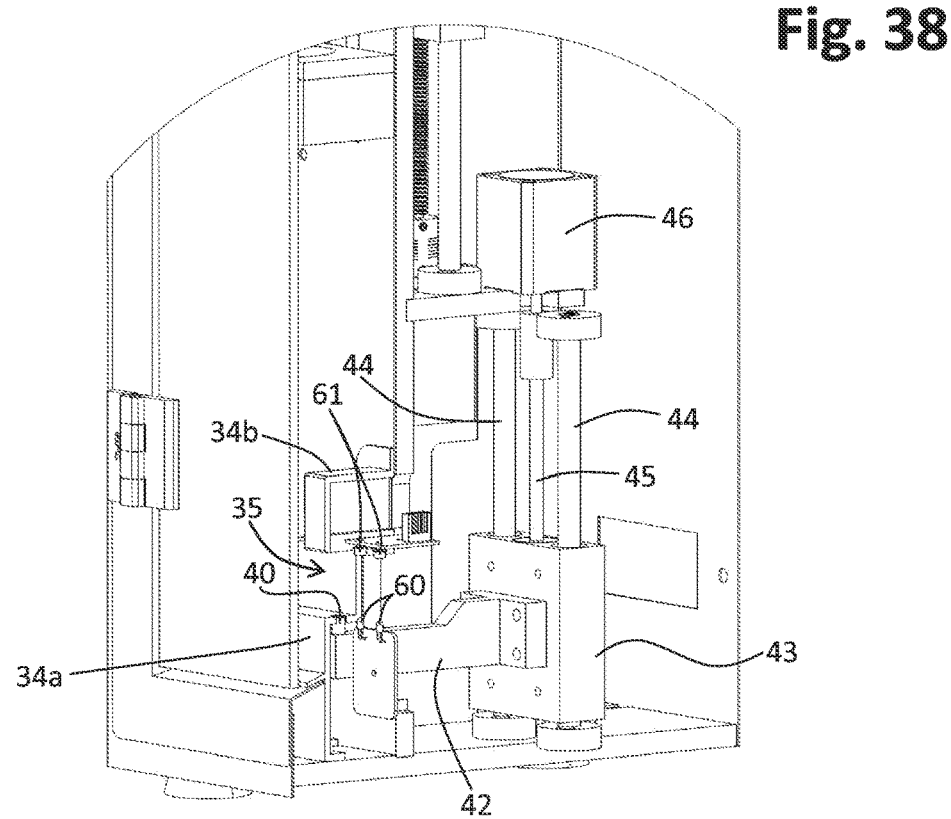
Figure 39:
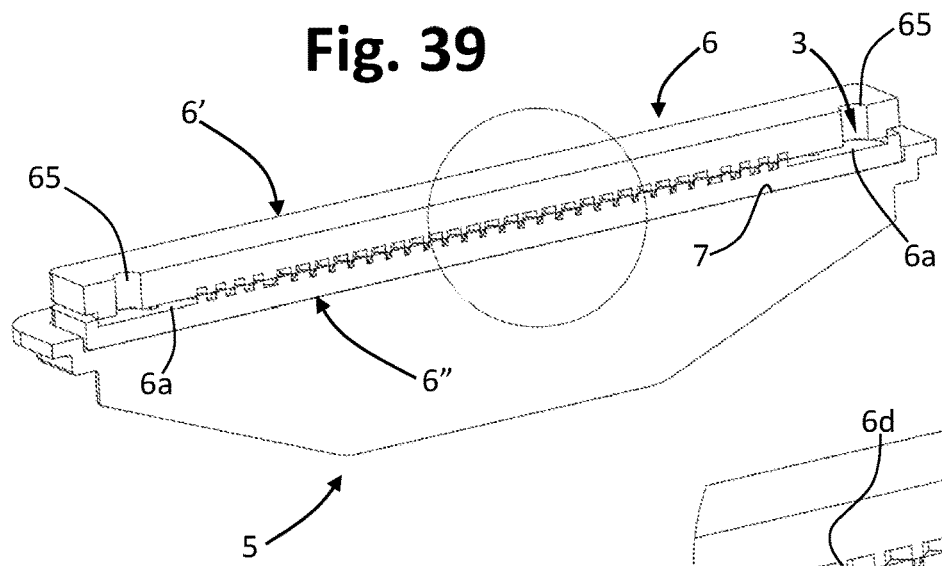
FIGS. 39 and 40 are views similar to those of FIG. 4, regarding a variant embodiment, in two different operative conditions.
Figure 41:
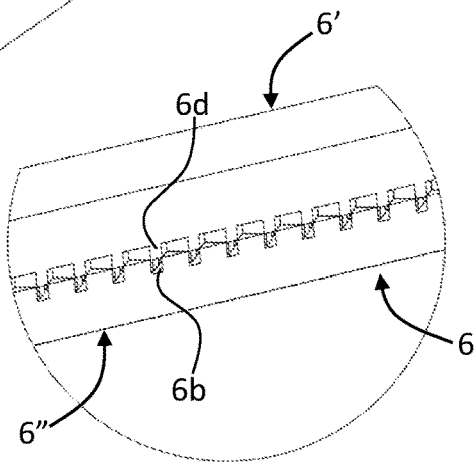
FIGS. 41 and 42 are two enlarged details of FIGS. 39 and 40, respectively.

In the example, such system includes a transmission member 42, shown in FIG. 35 and in the corresponding detail of FIG. 38, which is associated to a slide 43 constrained to the linear movement through vertical guides 44, for example in form of cylindrical bars, and it is actuated by means of a threaded shaft 45 driven by a corresponding bidirectional electric motor 46, possibly of the stepper type or a motor controlled in position.

In various embodiments, each of the actuation elements 38, designed to cause the pressure of the plungers of the syringes 4, is driven by means of a corresponding actuation system. A possible embodiment of one such system, regarding only one of the elements 38, is visible in FIG. 34 and in the corresponding detail of FIG. 37. In the example, each actuation element 38 is in a fixed position on a corresponding slide 50, constrained to the linear movement through corresponding guides 51, for example in form of cylindrical bars. Similarly, to slide 43, the slide 50 is axially traversed by a threaded hole—not indicated—in which there is engaged a threaded shaft 52 associated to a corresponding reversible electric motor 53, for example a stepper motor or a motor controlled in position.

Figure 37:
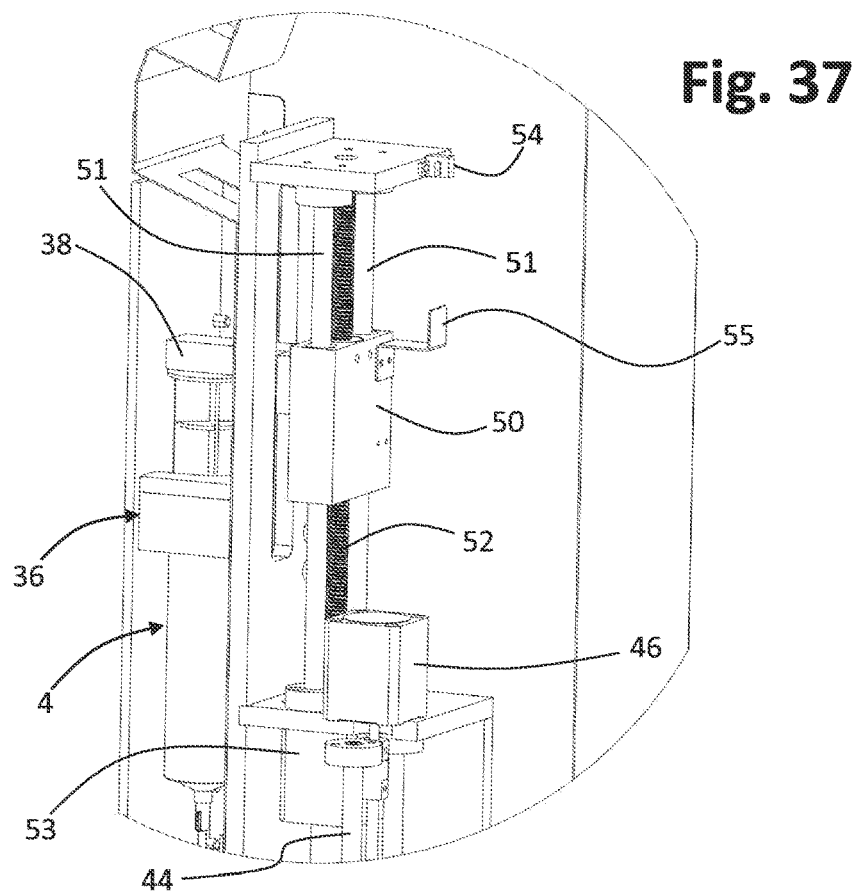

The motors 46 and 53 are preferably controlled through suitable position sensors, for example of the encoder type, belonging to the control system of the equipment. Preferably, there are also provided corresponding end-of-stroke sensor systems for the movement of the actuation elements 38 and 40; one such system, regarding one of the members 38, is shown in FIG. 37, which comprises a micro-switch or the like 54 in a fixed position and a corresponding moveable element 55 for switching the micro-switch 54, herein associated to the slide 50.

As mentioned, in various embodiments, the control system of the equipment 30 also includes an optical detection system, a possible embodiment of which is shown in the details of FIGS. 36 and 38. With particular reference to FIG. 38, in the lower portion 34a of the support arrangement 34 there is housed at least one photoemitter or optical transmitter 60, while in the upper portion 34b of such arrangement there is housed a photodetector or optical receiver 61, in a position axially aligned with the photoemitter 60. In various preferred embodiments there are provided for two pairs of photoemitters 60 and photodetectors 61 arranged in sequence, to enable use of the apparatuses 1 whose disposable devices comprise two pairs of optical detection passages 24-25, as in the case of the embodiments of FIGS. 15-27 and 28-30. The portions 34a and 34b are provided with holes, so as to enable the photoemitters to face the photodetectors (the holes for the photodetectors 60 are indicated with 41b in FIG. 31).

The operation of the equipment 30 provides for the positioning of the apparatus 1 on board, i.e. the housing of the disposable device 2 and of the syringes 4 in the corresponding positioning arrangements 34 and 36. Upon positioning the disposable device 2 at the corresponding seat 35 (FIG. 31), the detection passages 24 and 25 are axially aligned with the corresponding photoemitters 60 and photodetectors 61, respectively (FIG. 36), present in the portions 34a and 34a of the arrangement 34. Similarly, the adjusting member 9, or the corresponding sliding and guiding passage, is axially aligned with the actuation element 40 (FIG. 36).

Figure 32:
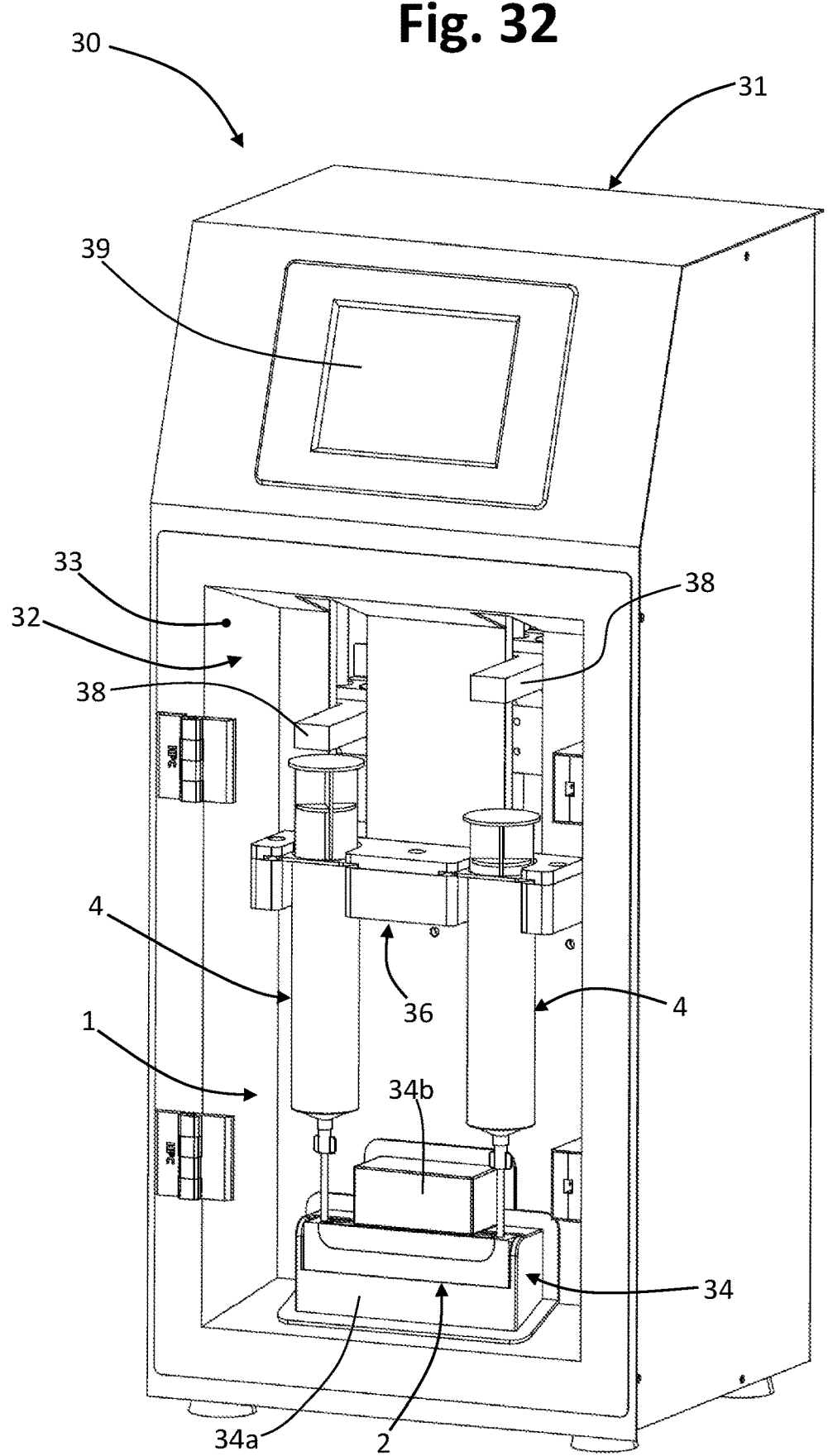
FIG. 32 is view of the equipment of FIG. 31 in an apparatus according to FIG. 28 mounted thereon.

In the starting condition of a cycle of operation, both the actuating elements 38 for the plungers of the syringes are preferably in a condition of maximum lift, to enable the insertion of at least one syringe 4 with the corresponding plunger extracted, and the control system may be prearranged to drive firstly a predefined element 38, corresponding to the seat 37 (FIG. 31) in which the syringe 4 initially containing the untreated adipose tissue is to be positioned: for example, with reference to FIG. 32, it should be assumed that the predefined element 38 is the one represented on the left in the figure. Obviously, the control system of the equipment 30 may be designed to require the user to indicate, through the user interface 39, the element 38 to be actuated first.

In case of use of a device 2 of the type illustrated in FIGS. 15-27, the operator shall introduce the adipose tissue together with a saline solution, using the syringe 4', as described previously; conversely, in case of an apparatus according to FIGS. 28-30, one of the two syringes 4 will already contain the adipose tissue to be treated, together with a saline solution. The treatment cycle, through which the control system drives the systems for actuating the elements 38 and element 40 in a coordinated fashion, may be started subsequently.

With the alternated actuation of the actuation elements 38, the adipose tissue is transferred from one syringe 4 to the other for a number of times, for example 4-5 times, with the adjustment arrangement of the disposable device 2 still in the inoperative condition thereof (or possibly only in a slightly throttled condition thereof).

The control system subsequently drives the system for actuating the element 40, causing a narrowing of the passage section of the duct of the device 2, for example bringing it to about half the nominal passage section of the duct. After performing such adjustment, the control system once again drives the elements 38 in alternated actuation, so as to cause a new transfer, possibly repeated, of the adipose tissue from one syringe 4 to the other. The system may subsequently controls a new actuation of the element 40, so as to further narrow the passage section of the duct of the device 2, with subsequent repetition of the passage of the tissue from one syringe to another. The number of transfers of the tissue between the syringes and/or reduction of the passage section of the duct may obviously be variable.

At the end of the process, in the syringe of final destination of the tissue, the content sediments by gravity, separating the oil, the disintegrated tissue containing the cells of interest and the saline solution dirty with blood. Thus, a new actuation of the element 38 corresponding to the syringe 4 of destination is controlled by the control system: the saline solution may be conveyed into the other syringe, which is subsequently removed and disposed.

The syringe 4 containing the "dirty" saline solution is removed by the operator and replaced with a new syringe 4 to receive the treated adipose tissue (possibly, before inserting such a new syringe 4 there is provided for an intermediate step with the insertion of another syringe containing a fresh saline solution for a further washing operation: such case provides for the repetition of at least some of the previous steps, such as an alternated actuation of the elements 38 for transferring the adipose tissue from one syringe 4 to another, a sedimentation and/or separation by gravity, an actuation of the element 38 corresponding to the syringe 4 of destination to convey the saline solution into the other syringe to be disposed).

After having positioned the aforementioned new syringe 4 for collecting the disgregated tissue, the equipment 30 is actuated once again, so as to transfer the treated tissue into such syringe.

The sensor system 60-61, when provided for, is preferably used after the cycle of tissue disgregation (or after the further washing), in particular after having left the layers in the syringe of destination to sediment, for automatically transferring the material of interest and blocking the flow when the waste material starts flowing into the other syringe.

To this end, the operation of the equipment—which is in standby condition in the meanwhile—is once again controlled by the operator, so that the element 38, corresponding to the syringe containing the tissue at the time, actuates the corresponding plunger once again, to transfer the entire treated tissue into the other syringe. The sensor system 60-61 controls the stop of the movement of the aforementioned element 38 when the optical characteristic of interests detected in the duct 3 takes a value representing the fact that the tissue has already been transferred into the final syringe.

In various embodiments, the detected optical characteristic is the transmittance of the fluid which flows through the duct 3. Generally, the transmittance level of the dirty saline solution, the treated tissue and the oil separated from the tissue is different, the value concerning the treated tissue being considerably different (much lower) with respect to the waste materials (dirty saline solution and oil). Thus, this enables to define a transmittance threshold, below which it is assumed that the treated tissue is flowing in the duct 3, while above it is assumed that the waste material is flowing in the duct 3.

FIGS. 39-42 illustrate a possible variant embodiment of a disposable device of the type described previously with reference to the FIGS. 1-6. In such embodiment, the duct body 6 comprises two parts 6' and 6" facing and/or sealed with respect to each other, with at least part of the duct 3 being defined between mutually facing surfaces of the two parts 6' and 6". In the represented case, the two parts 6' and 6" have a generally flat and oblong configuration, and one of the two parts—the upper part 6' herein—is traversed in the thickness direction thereof by holes 65, which enable the fluid to reach the connection attachments of the syringe 4 (for example see FIGS. 1 and 2, references 3a and 3b). In an embodiment of this type, the two parts 6' and 6" may be obtained using elastically deformable material or using a relatively rigid material. Preferably, the two parts 6' and 6" are sealingly coupled to each other, for example exploiting the elastic characteristic of the material they are at least partly made of (such as an elastic polymer or an elastomer); alternatively, such sealing may be obtained by interposing an additional specific element, such as an elastic gasket, or by sealing or gluing.

Figure 40:
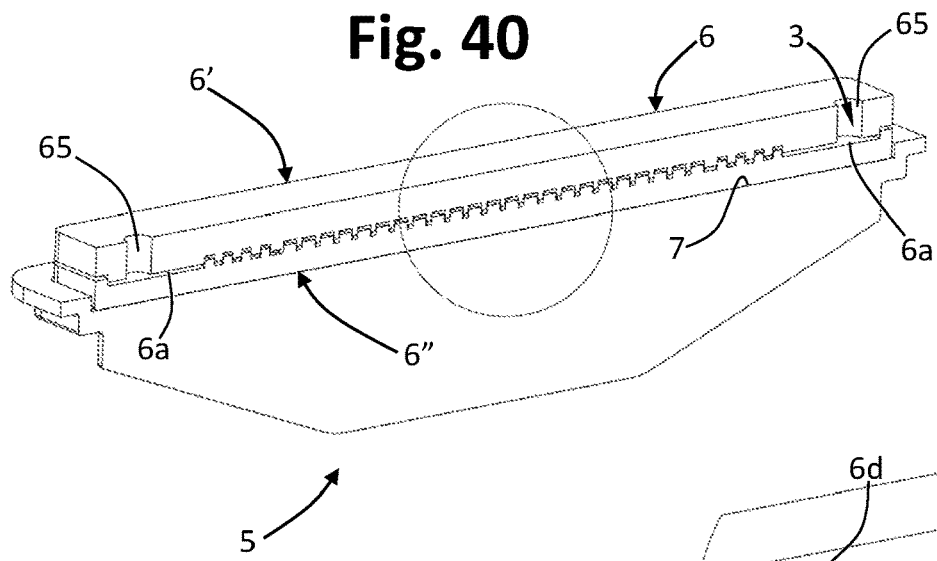
Figure 42:
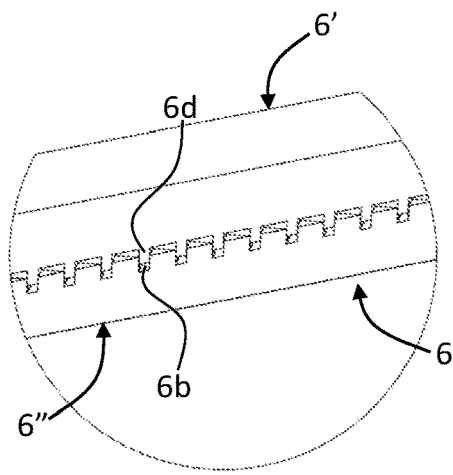

In various embodiments, at least one of the two parts 6' and 6" has a plurality of protrusions and/or recesses; preferably, one of the aforementioned mutually facing surfaces has a plurality of protrusions, while the other surface has a plurality of recesses, susceptible to receive the aforementioned protrusions. For example, with reference to the case illustrated in FIGS. 39-42, part 6" may define a plurality of crossed canalisations 6b, for example similarly to the illustration of FIG. 3, while part 6' may define a series of reliefs 6d having a shape substantially complementary to that of the aforementioned canalizations, or a shape such that the recesses can be at least partly received in the canalizations. In the inoperative condition of the adjustment arrangement—shown in FIGS. 39 and 41—the two facing surfaces of the parts 6' and 6" are at a first distance, which defines a given nominal passage section of the duct 3. By actuating the adjustment arrangement, for example as shown in FIGS. 40 and 42, the two surfaces are approached to each other at least in an area thereof, so that the reliefs 6d are partly wedged into the canalizations 6b, so as to reduce the passage section of the duct 3; the approaching between the surfaces is enabled by the elastic yielding of the perimeter contact area between the parts 6' and 6", it being alternatively enabled by the predefined yielding of an interposed elastic element, or it being enabled by a bending of at least one of the two parts 6' and 6".

The adjustment arrangement may employ elements similar to those indicated with 9, 10 and 11 in FIG. 2, in particular for causing a localised thrust and/or deformation only in one area A, or it may be designed to cause a more extended thrust and/or deformation (in terms of area) of part 6″ towards part 6′, preferably displacing a considerable part of the aforementioned protrusions and/or recesses.

Figure 43:
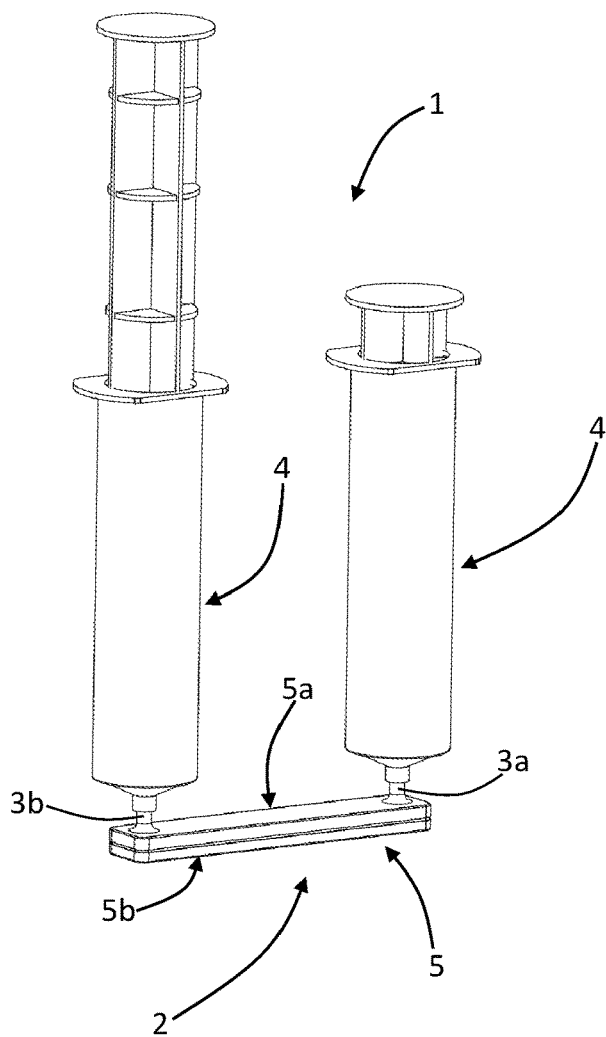
FIGS. 43 and 44 are schematic perspective views of a further possible embodiment of an apparatus for disgregating an adipose tissue according to the present invention.
Figure 44:
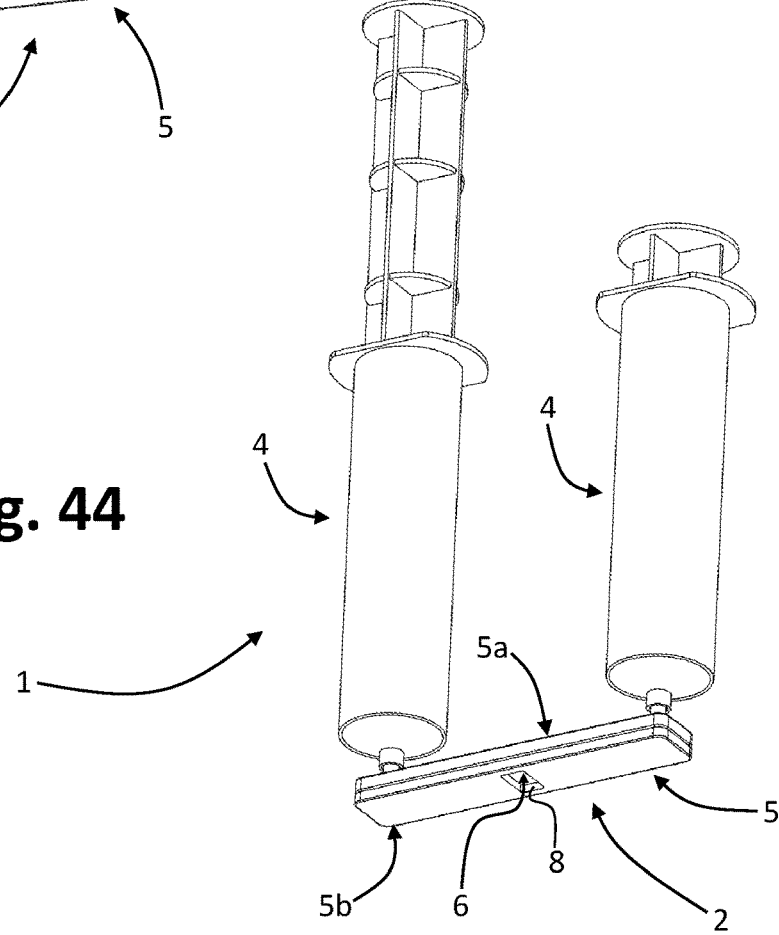

FIGS. 43 and 44 illustrate a further possible version of an apparatus according to the invention, inside which there may be provided a duct body consisting of a simple flexible tube, possibly having quadrangular cross-section, which connects the two attachments 3a and 3b, or of a duct body of the type indicated with 6 in FIGS. 2-6, or even a of a duct body made of two parts 6′ and 6″, like in FIGS. 39-42.

In such embodiment, one of the parts of the supporting body 5—part 5b herein—has a passage 8 which enables operating the deformation required to cause the narrowing of section of the duct for the flow of the adipose tissue. An apparatus 1 of this type is susceptible for use in combination with a corresponding automated equipment, slightly different from that of FIGS. 31-38 as regards the attainment of the housing arrangement for the disposable device 2 (which will not be provided with an optical sensor system in this case). It will be observed that, in the case of the embodiments of FIGS. 43 and 44, the adjustment arrangement basically includes only the at least partly deformable duct and the corresponding passage 8 obtained in the supporting body 5: in this case, the adjusting member belongs to the external equipment and it may be constituted by an actuation element of the type indicated with 40 in FIGS. 31-38.

The adjustment arrangement of the disposable devices according to the invention described up to now provides for a variation of section of at least one portion of at least one treatment duct, preferably obtained by means of a deformation, in particular a deformation of at least one duct which is at least partly flexible and/or elastic. On the other hand, other embodiments do not necessarily provide for a deformation of the duct for the flow of the adipose tissue, given that there can be provided parts, even of the rigid type, adapted to be displaced in the duct to cause a variation of a passage section thereof.

For example, according to possible embodiments of the invention, the aforementioned duct may have at least one through transverse opening, through which there can be displaced a corresponding adjusting member having a head end that faces the inside of the duct or protrudes thereinto, with said adjusting member which is displaceable to vary in a controlled way a passage section of the duct. An embodiment of this type is for example schematically represented in FIGS. 45-48.

Figure 45:
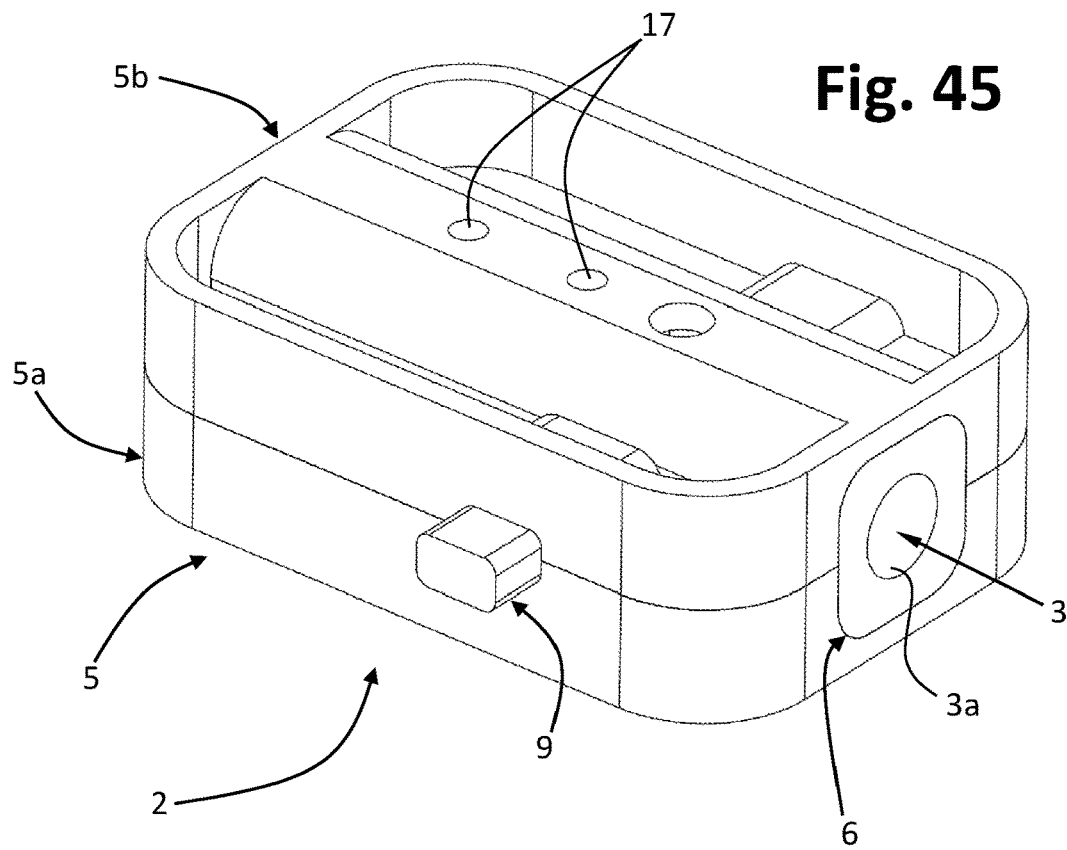
FIG. 45 is a schematic perspective view of a further possible embodiment of an apparatus for disgregating an adipose tissue according to the present invention.
Figure 46:
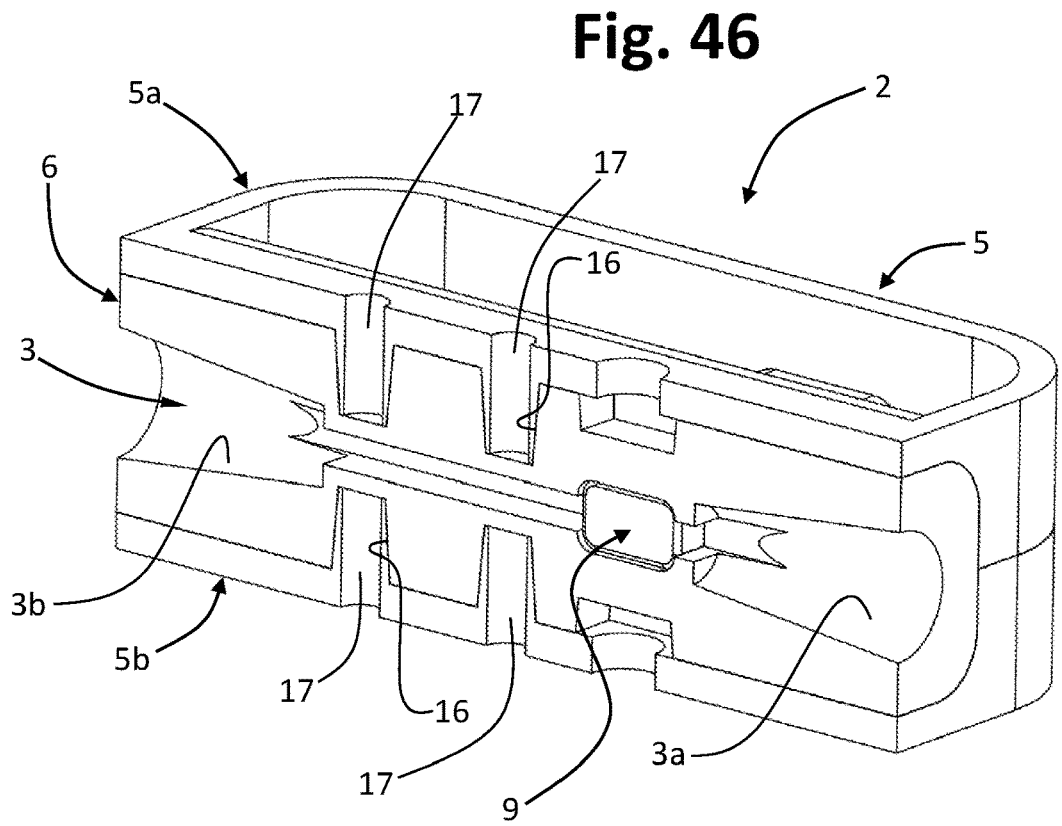
FIGS. 46, 47 and 48 are schematic sections of the apparatus of FIG. 45.

Initially referring to FIGS. 45-46, also in this embodiment the disposable device of the apparatus according to the invention has a supporting body 5 which comprises at least two parts 5a, 5b coupled to each other, so as to house at least partially a duct body 6, which can be made of a rigid material or else of a deformable material. Similarly, to the embodiment shown in FIGS. 9-15, the body 5 and the body 6 are configured in such a way that the two ends of the latter are accessible outside the former. Also in this case the axial ends 3a and 3b of the duct 3 may be configured to serve as attachments for the syringes and between the bodies 5 and 6 there may be provided for corresponding coupling means of the type previously indicated with 16 and 17 (which can also be possibly exploited as optical detection passages, when the body 6 is made of transparent material).

According to a preferred version, both the body 5 and the body 6 are obtained by forming or moulding, in particular moulding a polymer or a thermoplastic material or a resin or a metal or an alloy, possibly by co-moulding or over-moulding between the bodies 5 and 6. Preferably, at least one body, such as the body 6 of the duct 3, may be made of relatively rigid and/or transparent material, for example glass, polyethylene or PE or PEHD, cyclic-olefin copolymers or COC, polyethylene or PE or PEHD, acrylic or methacrylate or polymethylmethacrylate or PMMA, polycarbonate or PC, styrene or acrylonitrile butadiene styrene or ABS, polysulfone or PSU.

Figure 47:
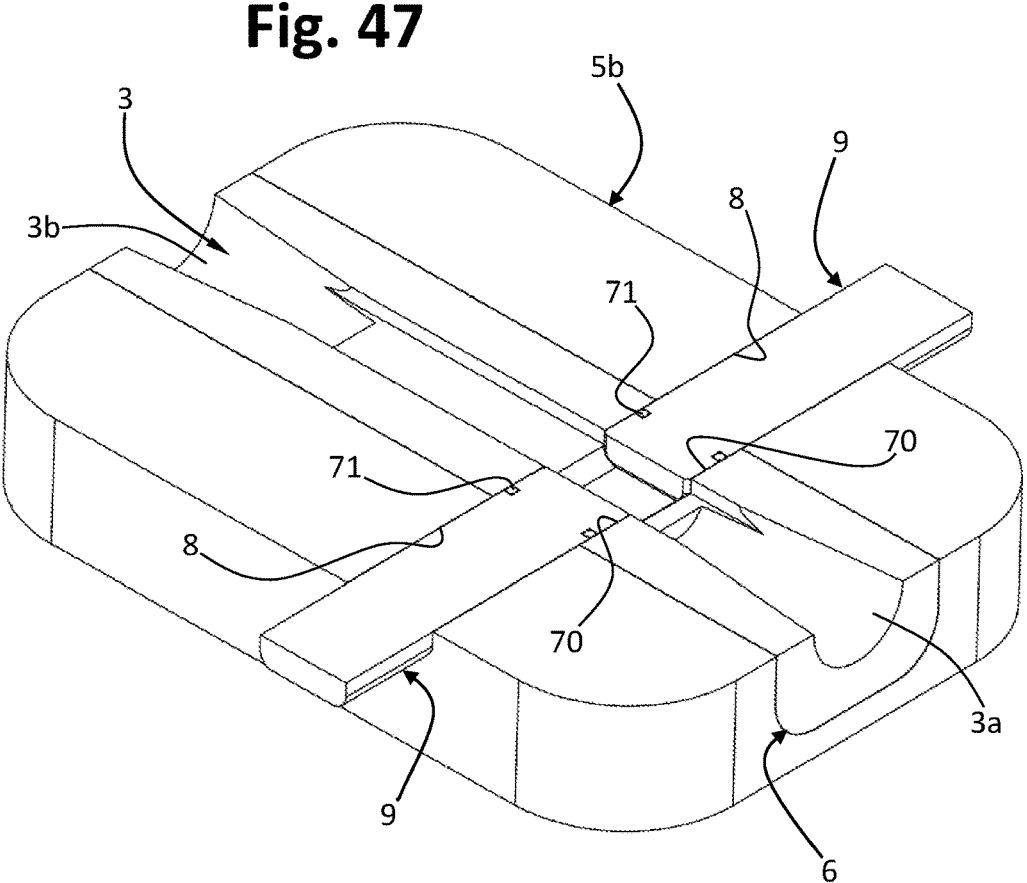
Figure 48:
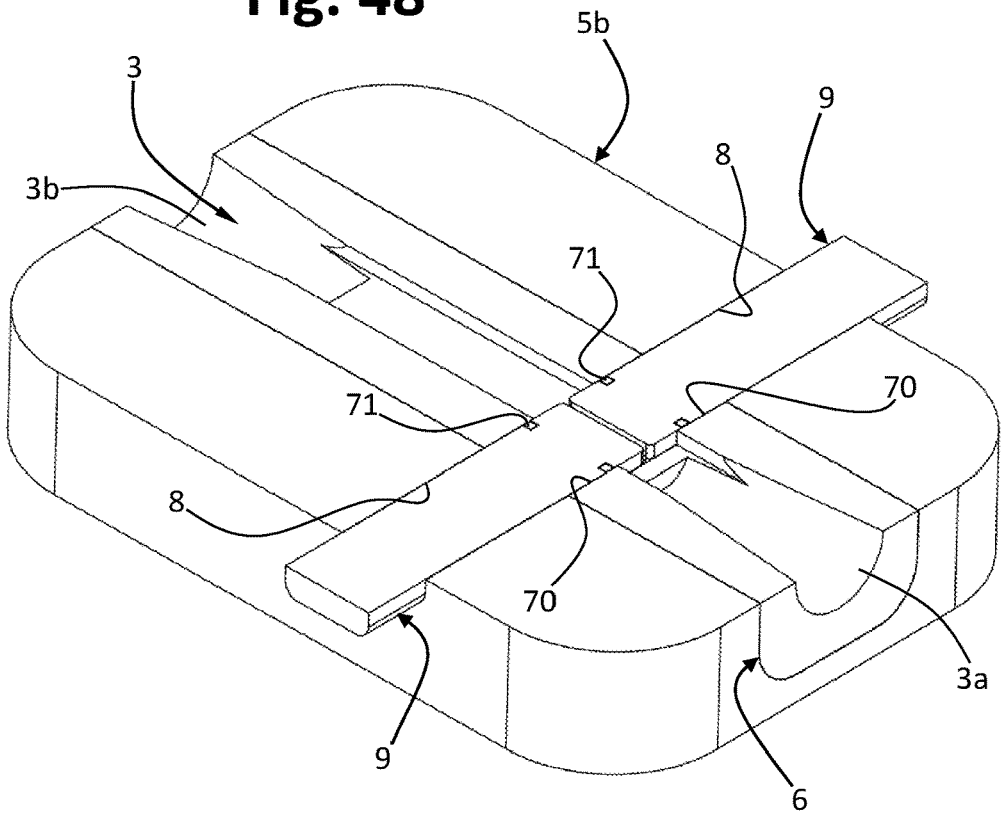

As observable particularly in FIGS. 47 and 48, the body 6 has two through transverse openings, indicated with 70, through which corresponding adjusting members 9 can be displaced; preferably, between the surfaces that define the openings 70 and the surface of the corresponding member 9 there are provided sealing means, herein represented by gaskets 71 mounted on the adjusting members 9.

The transverse openings 70 at the duct 3 are axially aligned with respective lateral passages 8 of the body 5, in which the members 9 are slidably inserted, possibly sealingly, so that the external end thereof protrudes outside the body 5, to be operable manually or by means of an automated equipment.

The openings 70 and the passages 8, on the one hand, and the members 9, on the other hand, preferably have dimensions of section such to allow a precise sliding of the members.

FIG. 47 illustrates an inoperative condition of the adjustment arrangement, in which the members 9 do not cause any reduction of the passage section of the duct 3. Conversely, FIG. 48 illustrates the case of a minimum passage section for the duct 3, in which the internal ends of the members 9 are extremely close to each other, to define the aforementioned minimum passage section. Obviously, various intermediate positions with respect to those represented are possible. According to other embodiments, the internal end of at least one of the adjusting members 9 may be shaped differently, for example with profiles inclined or shaped to facilitate the flow in the duct 3 and/or provided with one or more reliefs or spacer elements, having the function of guaranteeing the presence of a minimum distance between the head ends of the two members 9 when in maximum closure position, so as to enable the presence of a minimum passage section.

A device of the type described with reference to FIGS. 45-48 may also be provided with only one member 9, with the corresponding through opening 70 and passage 8. Possibly, the duct 3 may be directly defined by the body 5 (in which case the body 6 is not necessary) or, conversely, the body 5 could be omitted.

FIGS. 49-52 illustrate a further possible embodiment a device 2 for use in an apparatus according to the invention, according to which the duct body consists of a flexible tube 6, at whose two ends there are associated respective attachments 3a and 3b, for example Luer attachments, to allow the connection of the syringes for transferring the adipose tissue. The tube 6 which connects then two syringes—not represented herein—may have an internal diameter comprised between 2 and 5 millimetres, preferably comprised between 3 and 4 mm.

Figure 49:
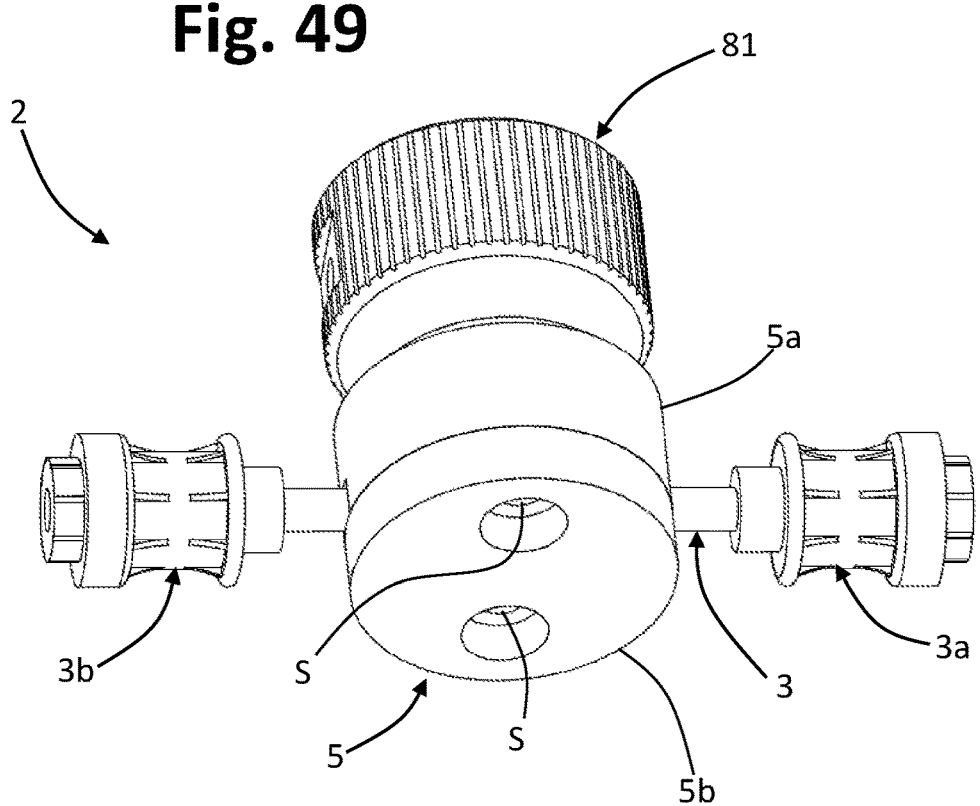
FIG. 49 is a schematic perspective view of a further possible embodiment of an apparatus for disgregating an adipose tissue according to the present invention.

The supporting body 5 is also in this case made of at least two parts 5a and 5b fixed to each other using suitable fixing elements, for example screws or the like, indicated with S in FIG. 49, or coupling reliefs and/or seats obtained in the parts 5a and 5b. The two parts 5a and 5b mutually define a transverse passage—indicated with 80—in which the tube 6 is partly inserted.

One of the two parts of the body 5—part 5*a* herein—has a seat 8 for an adjusting member 9, so that the head 9*a* of the latter faces an intermediate portion of the tube 6; the stem 9*b* of the member 9 may be advantageously threaded and engaged in a suitable threading 82 provided in a cylindrical portion of the seat 8. At the end of the member 9 opposite to the head 9*a* there is associated a knob 81 or a similar gripping element, configured to allow rotation of the member 9, and thus adjust the position of the head 9*a* thereof with respect to the tube 6. In alternative embodiments, the knob 81 is advantageously replaced by an automatic actuator system, comprising for example at least one from among a motor or a transmission element actuatable by a motor, such as a gear.

Figure 50:
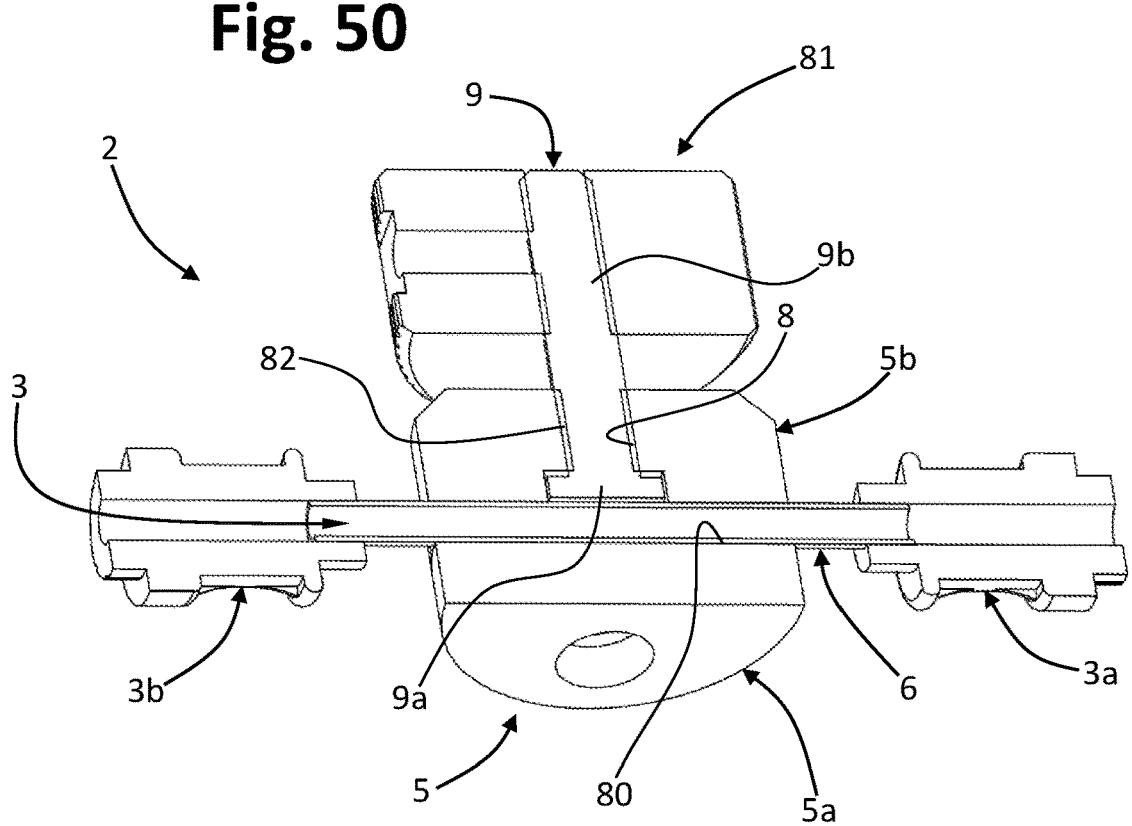
FIGS. 50 and 51 are schematic sections of the apparatus of FIG. 49, in two different operative conditions.
Figure 51:
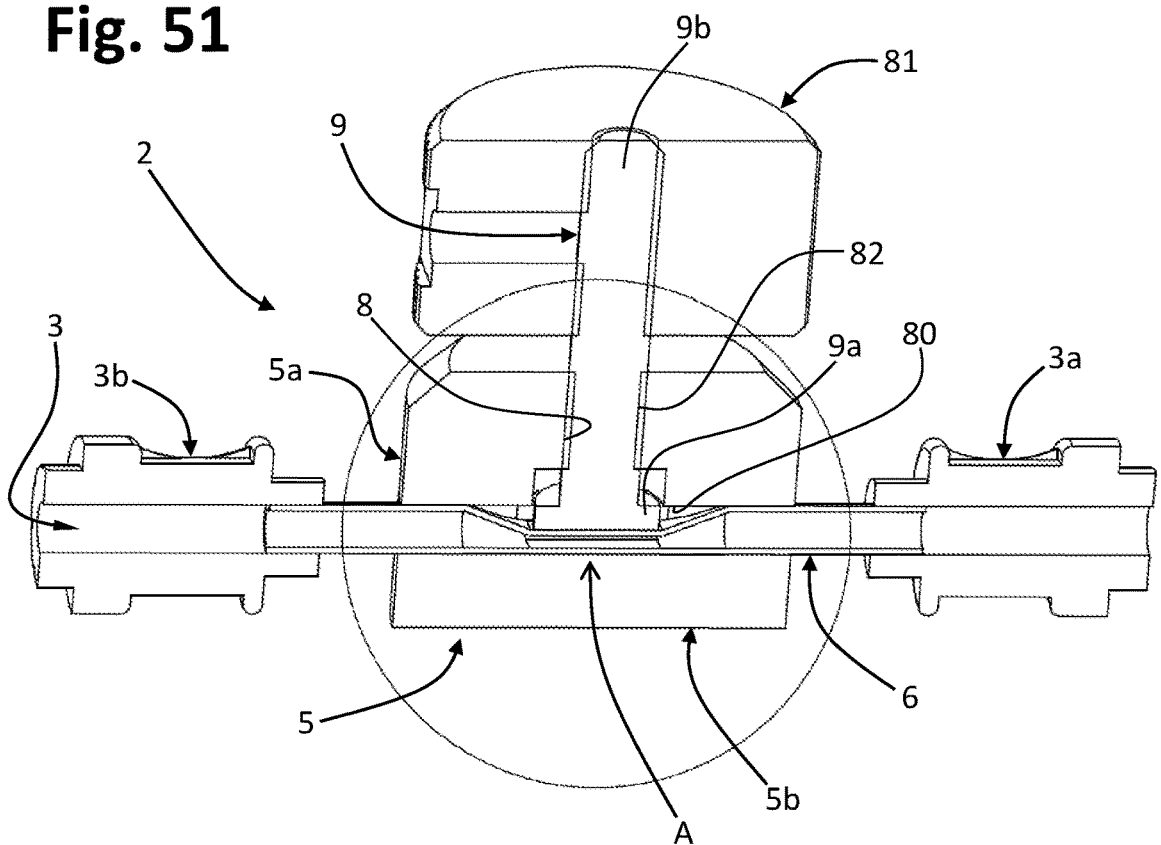
Figure 52:
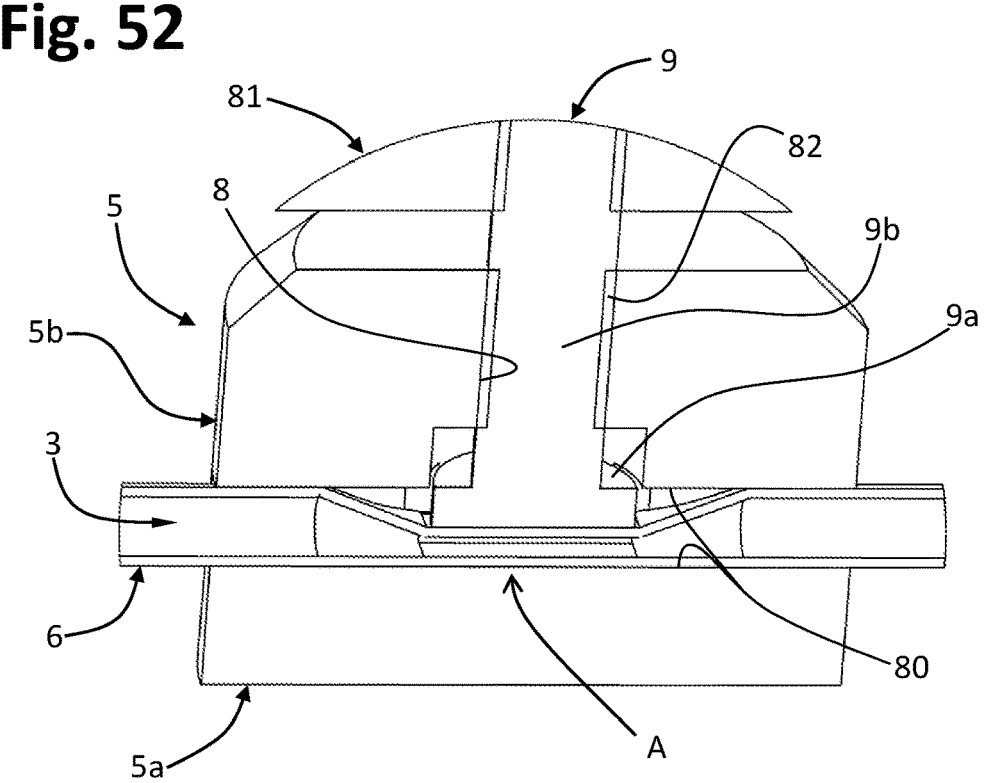
FIG. 52 is a detail of FIG. 52.

FIG. 50 illustrates an inoperative condition of the adjustment arrangement, in which the tube 6 is not deformed. Conversely, FIGS. 51 and 52 show an adjustment position such that the head 9*a* of the member 9 locally crushes the tube 6, with respect to the rigid abutment defined by the transverse passage 81 in the body 5, determining a local reduction of the passage section thereof in the area indicated with A, similarly to the description outlined previously regarding various embodiments.

The solution of FIGS. 49-52 is extremely simplified from a construction point of view and it has the advantage lying in that the illustrated device 2 can be partly re-utilised, if need be. As a matter of fact, it should be observed that, preferably by separating or mutually loosening the two parts 5*a* and 5*b* of the supporting body 5, a contaminated tube 6 can be removed and disposed, so as to replace it with a new sterile tube, before the parts 5*a* and 5*b* are fastened to each other again; to this end, there are preferably provided for fixing element S of the quick coupling and/or release type.

Lastly, it should be observed that though preferable, the body defining the duct for the flow of the adipose tissue between the two collecting containers, exemplified by the syringes 4 up to now, should not necessarily be a flexible or elastically deformable body, but it can also be a body deformable in an plastically or permanent manner. For example, with reference to the case of FIGS. 49-51 it will be observed that the tube 6 could for example be made of a metal material and have a thickness such to enable a progressive deformation thereof, in the sense of reducing the passage section of the duct 3. Obviously, similar observations shall also apply to other embodiments described previously, even though the use of materials which can be deformed at least partly elastically to provide the duct body shall be deemed preferable towards the implementation of the invention.

In various embodiments, the apparatus according to the invention may include further pre-assembled devices, with respect to those described previously, separable at the end of given steps and/or possibly hydraulically switchable using corresponding taps or valves.

Figure 53:
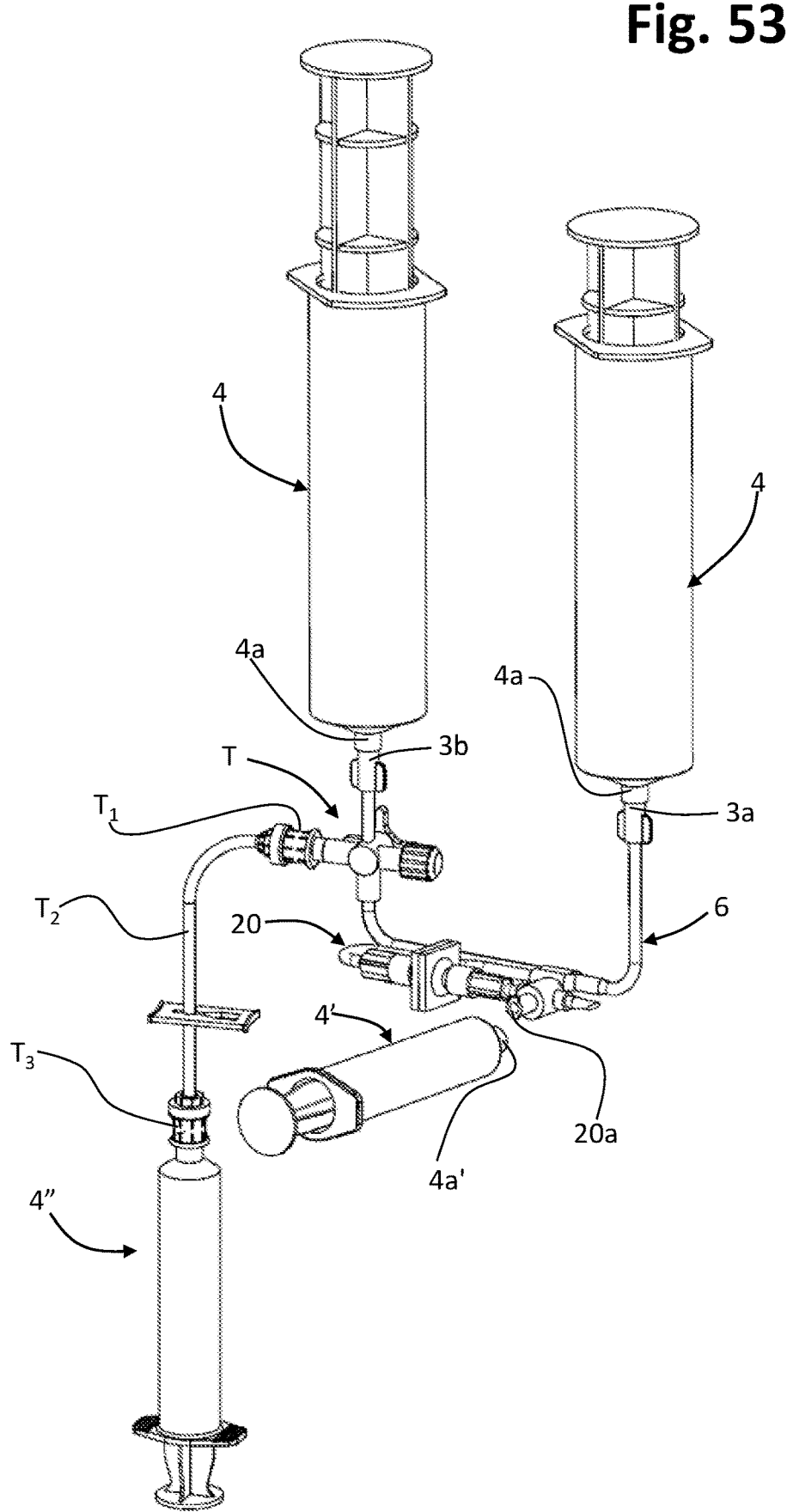
FIGS. 53 and 54 are views similar to that of FIG. 13, regarding possible variant embodiments of the invention.

For example, FIG. 53 partly illustrates an apparatus having a basic structure similar to that of the apparatus of FIGS. 15-27, but including a further collecting container 4", which can for example be used for introducing a fresh washing saline solution into the disposable device 2 and/or for receiving the treated adipose tissue.

In such an embodiment, to the disposable device, and in particular to the duct 3 thereof, there is associated a diverter valve or tap T that can be controlled manually or in an automated way, to which the container 4" is connected for introducing the washing saline solution, and/or for receiving the waste fluid, and/or for receiving the treated tissue and then enabling to separate such container 4". In the example, the valve T is a three-way valve. Advantageously, in such an embodiment, the fitting T1 of the valve T which is designed for connection with the further container 4" may be provided with separable fitting means and/or a unidirectional valve $T_1$, so as to avoid loss of fluids when separating or prevent possible contaminations from the outside. When the container 4" is connected to the valve T through a tube $T_2$, separable fitting means and/or a unidirectional valve may also be integrated in the attachment $T_3$ of the tube designed for connection with the container 4".

Figure 54:
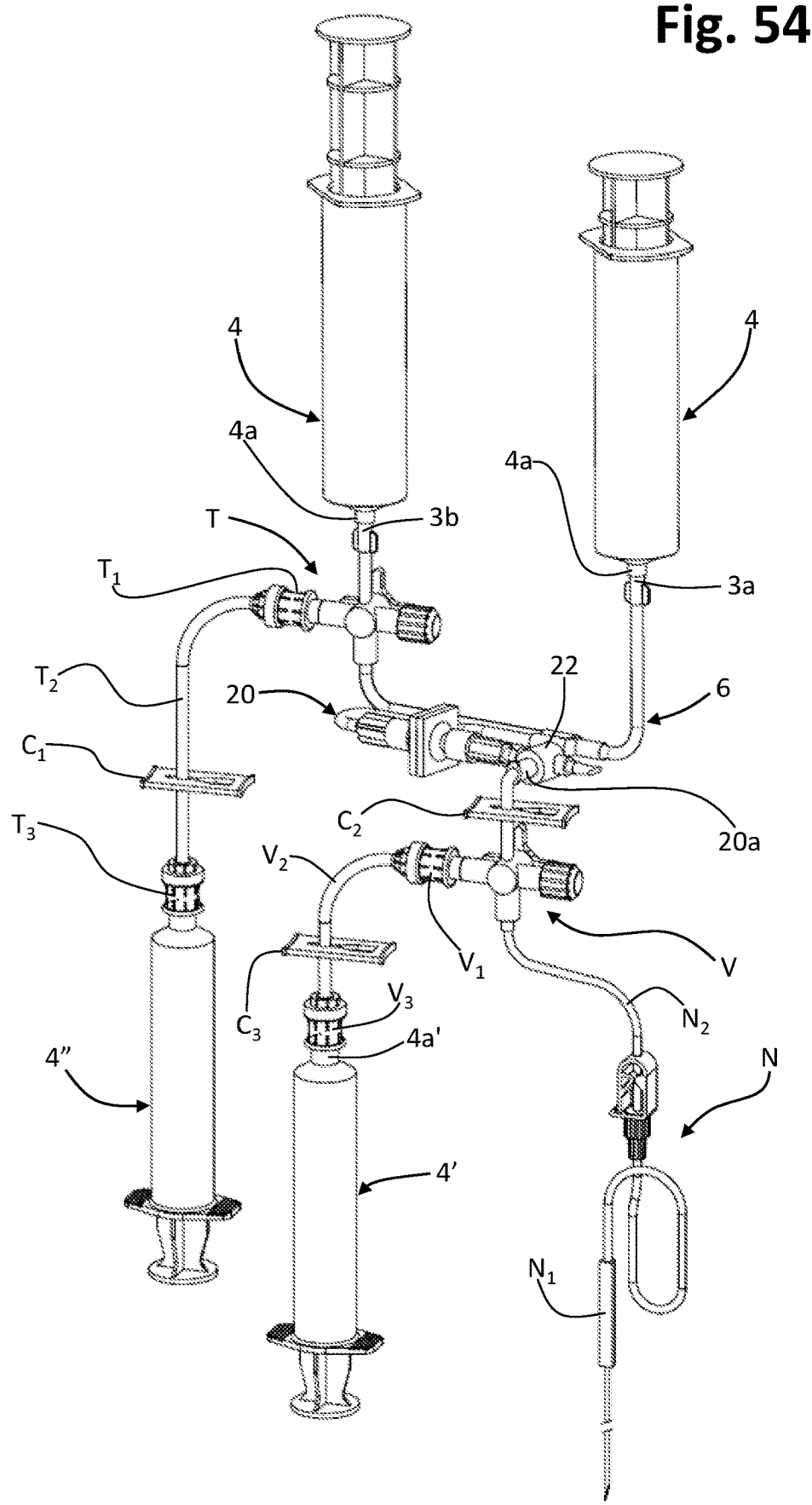

FIG. 54 regards a similar embodiment, in which reference N designates as a whole a device for taking the tissue to be treated, for example comprising a needle or cannula $N_1$. Indicated with V is a further diverter valve or tap V, of the three-way type herein: a first way of the valve V is connected to a tube $N_2$ of the taking device N, a second way is connected to the inlet 20*a* of the duct 20 and the third way—preferably provided with a separable fitting $V_1$, very preferably integrating a unidirectional valve—is designed for connecting with a syringe 4'. The syringe 4' may be directly fitted into the corresponding way of the valve V or, like in the exemplified case, through a tube V2 provided with a releasable fitting $V_3$ and/or a unidirectional valve.

According to a possible method of use, the needle $N_1$ is inserted into the patient and the biological tissue, adipose tissue for example, is suctioned through the syringe 4', after first placing the tube $N_2$ and the syringe 4' in fluid communication and simultaneously closing the way regarding the inlet 20*a*, through suitable switching of the diverter valve V. Subsequently, the valve V is switched, so as to place the syringe 4' in communication with the inlet 20*a* of the duct 20, simultaneously closing the way to which the tube $N_2$ is associated. By acting on the syringe 4', the tissue may thus be introduced into the disposable device, as explained previously, through the unidirectional valve 22, the filter 21 and the duct 20. Both the device N and the syringe 4' may be removed, if need be, by exploiting the presence of separable fittings.

It should be observed that, if need be, the functionality of the taps or valves T and/or V may be obtained through clamp valves, for example of the type indicated with C1, C2 and C3, arranged on the tubes of interest, according to methods known to a man skilled in the art.

Obviously, solutions of this type can also at least be partly implemented in the other apparatus described previously.

Figure 55:
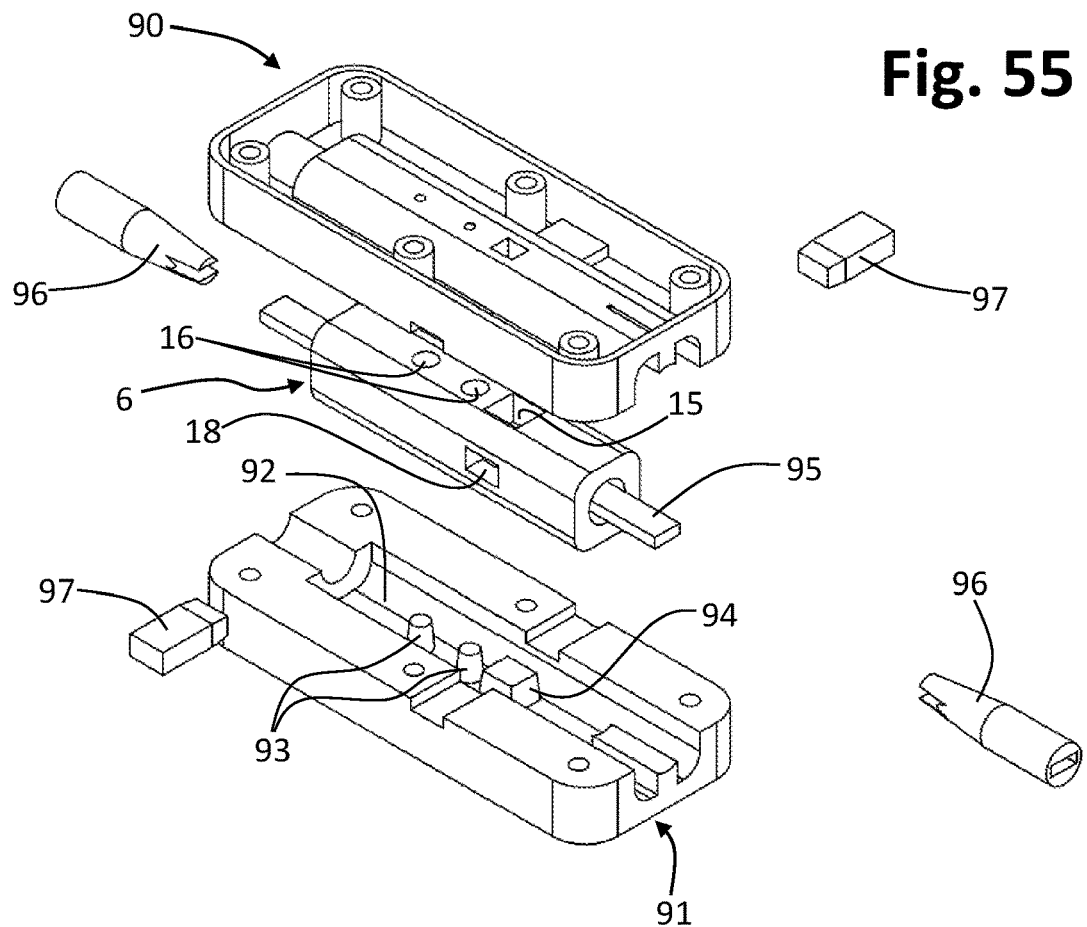
FIG. 55 is a schematic perspective view of an example of a moulding equipment that can be used to obtain a duct body of a disposable device according to the invention.
Figure 56:
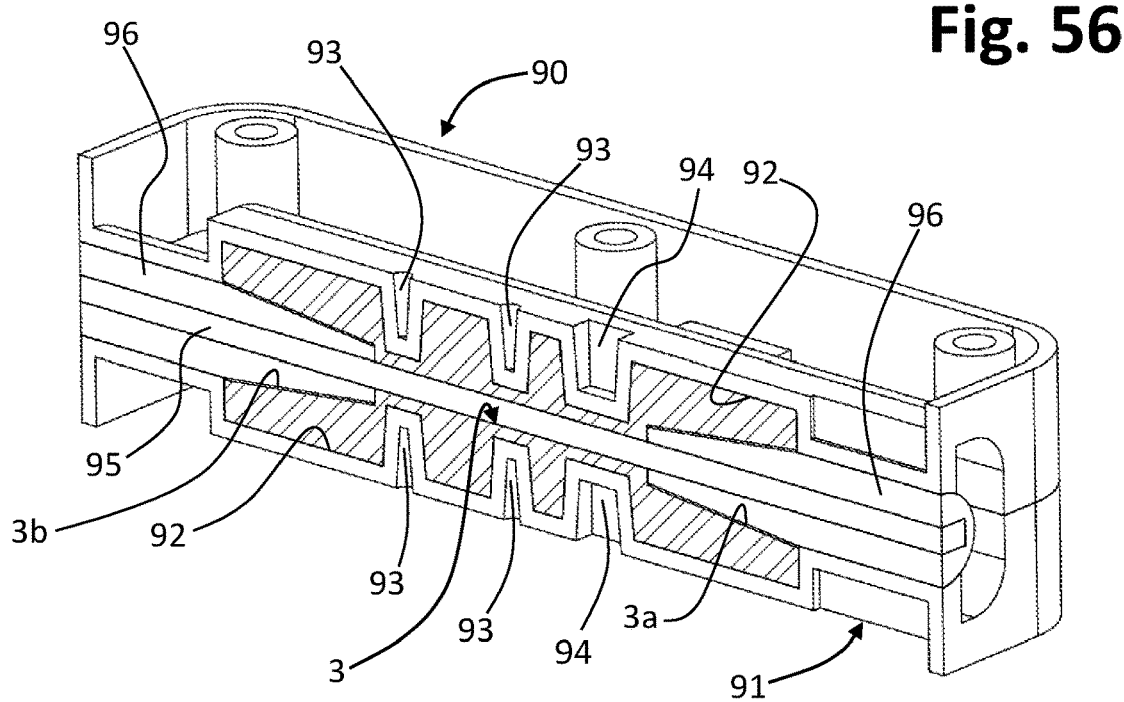
FIG. 56 is a schematic section of the equipment of FIG. 54, in an operative step.

In various embodiments, the duct body 6 of the described disposable devices is obtained by moulding, for example using a polymer or an elastomer. FIGS. 54 and 55 exemplify an equipment that can be used for the purpose, for example suitable to obtain the bodies 6 of FIGS. 11-14 and—with slight modifications—also the body 6 of FIGS. 45-48, respectively.

The equipment or mould includes—in the example—two mould parts 90 and 91, each defining a respective impression 92 configured to define the external profile of the body 6. To this end, in various embodiments, such impression 92 includes reliefs 93 for defining the cavities 16 of the previously mentioned optical detection passages (and/or of the aforementioned coupling and/or positioning means) and/or reliefs 94 for defining the cavities 15 for the corresponding adjusting members 9.

The internal profile of the body 6, i.e. of the internal duct thereof, can be obtained using pins and/or plugs. In the illustrated example, for this purpose there are provided for a moveable insert or pin 95, for defining the profile of the intermediate portion of the duct 3—quadrangular-shaped herein—and two moveable mould parts or carriages 96, for defining the two ends or attachments 3a, 3b of such duct, frusto-conical-shaped herein (see FIGS. 12-13 and 46 for reference). Preferably, at least one of the moveable mould part 96 is provided with an axial passage, for coupling and/or guiding and/or displacing the pin 95.

The moulding equipment may also be provided with moveable mould parts or carriages—indicated with 97—for defining further cavities 18 and/or seats 70, when such cavities or seats are provided for, preferably by adjusting different positions of the moveable parts 97 with the aim of obtaining blind seats and/or through seats or openings.

The descriptions outlined above clearly show the characteristics and advantages of the present invention. Practical tests carried out by the Applicant proved that the apparatuses and the methods proposed allow obtaining an effective disgregation of the initial adipose tissue, offering a preparation rich with cells of interest that can be easily injected using small diameter needles. All this is obtained through manipulations that can be deemed "non-relevant" according to the standards of the sector.

The obtained preparations are rich with "young" stem cells, given that the performed disgregation allows breaking the largest adipocytes; even the risks of damaging the cells are considerably mitigated, for example with respect to process that provide for the centrifugation of the tissue or the treatment thereof using sieves and metal grinding balls. The application procedures provided for, even when carried out manually, are per se simple and easily repeatable, guaranteeing good uniformity of the product. The treatment cycle of the adipose tissue is substantially closed during the disgregation procedure, thus mitigating the risks of degradation and contamination of the same tissue. This also in consideration of the fact that, as is apparent from what has been described and shown, the adjustment arrangement provided in accordance with the invention is accessible and/or operable from the outside of the disposable device, without requiring any disassembling of the device itself of any replacement of internal parts thereof. Lastly, the proposed apparatuses, and in particular the corresponding disposable devices, are easy and economical to obtain.

It is clear that the numerous variants are possible for a man skilled in the art, without departing from the scope of the invention as defined by the claims that follow.

In the apparatuses according to the invention, and in particular in the corresponding disposable devices, there may be provided for several area of adjustment of the type previously indicated with A, for example providing for several adjusting members 9 of the described type, but arranged side by side or in series along the duct 3 for the flow of the treated tissue, possibly actuated simultaneously by the same actuation element 10 or actuated distinctly by respective actuation elements 10. In case of several adjusting members 9, they could also be susceptible to assume adjustment positions different from each other. For example, the adjusting members 9 of three different adjustment areas could be initially provided for a "pre-treatment" of the virgin adipose tissue, by stepped adjustment heights, so as to define an initial with facilitated inlet, i.e. scarcely throttled, an intermediate area averagely throttled and a final area even more throttled; this enables facilitating the flow of the virgin tissue of larger dimensions in a first direction, then inverting the adjustment heights of the initial and final areas, when the tissue is made to flow in the opposite direction. All the adjusting members 9 could be subsequently arranged at the same adjustment height in the three aforementioned areas, for the fine treatment of the pre-treated tissue. As an alternative, there could be provided for other adjustment heights, for example arranged alternatingly, for example with the initial area averagely throttled, the intermediate area very throttled and the final area averagely throttled, with the aim of providing a facilitated inlet in both directions of flow of the tissue, without having to vary them every time the direction of flow is changed. Even such variable arrangement of the adjusting members 9 could be defined in an automated way by an equipment provided with an appropriate number of controlled actuators.

In various embodiments, the disposable device comprises two or more ducts 3, for example connected in series and/or parallel and/or branched with respect to each other, even so as to define more than two ends 3a, 3b to which the respective handling and/or collecting devices 4 can be connected. In combination and/or alternatively, in various embodiments the disposable device includes two or more areas A for deforming or modifying the configuration of the duct 3, so as to vary one or more corresponding passage sections thereof: in such case, for example, one and a same adjustment arrangement may be prearranged to enable the variation of several passage sections along the extension of the duct 3, or there may be provided for several adjustment arrangements each configured to vary a respective passage section.

Also, in various embodiments, to one and the same supporting body or casing there may be associated a plurality of duct bodies, each defining at least one duct for the flow of the biological tissue to be treated.

According to a variant, not illustrated, of an apparatus 1, the displacement of at least one plunger of at least one of the handling and/or collecting devices 4 is carried out pneumatically, by applying a pressure and/or a suctioning of air or gas, in particular via a variation of pressure from the side of the plungers that is not at contact with the fluids (the upper side in the exemplified figures). Such pressure and/or suctioning is induced using suitable pneumatic devices, such as a compressor and/or a vacuum pump, connected to a suitable chamber of the handling and/or collecting device 4. Preferably, said pneumatic devices are provided for in the equipment 30, by way of alternative to the described motorized mechanical actuators.

According to a further variant, not illustrated, of an apparatus 1, a first handling and/or collecting device 4 connected to an end 3a or 3b of the first duct 3 comprises an elastic element, such as a spring or an hermetically sealed chamber, so that the flow of the biological tissue in one direction, for example caused by the thrust exerted by a second handling and/or collecting device connected to the other end 3a or 3b, determines a thrust and the ensuing displacement of a plunger or a membrane of the first device 4, which compresses the spring or the air or gas contained in said hermetic chamber, so as to increase the pressure thereof. Once the thrust through the second handling and/or collecting device 4 ceases, the compressed spring or the pressure of the air or gas compressed in the hermetically sealed chamber determines a thrust on said plunger or membrane of the first device 4, thus determining the displacement of the biological tissue in a second direction in the duct 3. Possibly, the plunger or membrane could be omitted: in such case, the gas could be directly compressed by the flow of the biological tissue and/or the biological tissue could be directly pushed by the compressed gas. Such variant enables reducing the number of actuation devices, such as the actuators driven by the equipment, in that at least one handling and/or collecting container is actuated by the elastic element, for example by the spring or by the compressed gas in the hermetic chamber.

According to another variant, not illustrated, of an apparatus 1, at least one part of a handling and/or collecting device 4 and/or a corresponding opening 4a are integral or fixed or glued or sealed or obtained in a single piece with the disposable device 2 and/or with at least one first duct 3 or duct body 6 and/or a supporting body or casing 5; preferably, at least one part of a handling and/or collecting device 4 is moulded or sealed with at least one part of the disposable device 2, such as the supporting body or casing 5 and/or the duct body 6, particularly using a polymer or moulded or co-moulded or over-moulded or heat sealed or vibration sealed thermoplastic materials.

According to a further variant, not illustrated, of an apparatus 1, there are provided for two ducts 3, with respective deformation areas A, connected to a shared end, i.e. two ducts 3 provided with three inlet/outlet openings to which three handling and/or collecting devices 4 are connected. Preferably, in such a configuration, the actuation of the handling devices is alternated, so as to alternate the flow of the biological tissue in the two ducts 3, for example to enable a different treatment or disgregation of the tissue through two differently adjusted areas A, lastly making the treated tissue to flow into two different handling and/or collecting devices 4 of destination.

According to a further variant, not illustrated, of an apparatus 1, there is provided for an actuation system of the pneumatic type suitable to vary or deform at least one part A of at least one duct 3, preferably comprising at least one pneumatically driven actuation member, such as a pneumatic cylinder moveable linearly and angularly to vary the position of an adjusting member 9 of the type described previously, or else a pneumatic valve and/or an inflatable chamber and/or an inflated or pressurised throttling member, where for example a greater inflation or an increase of pressure in such throttling member causes a narrowing of the section of the duct 3. Preferably, such throttling member in form of an inflatable chamber may be integrated or obtained in a single piece in the duct body 6, such as an inflatable chamber located at a throttling area A, provided with a corresponding inlet/outlet for a pressurised fluid and/or adapted to inflate the throttling chamber and vary the section of the duct 3.

The invention claimed is:

1. An apparatus for disgregating a biological tissue, in particular an adipose tissue including stem and/or multipotent cells for use in regenerative medicine, the apparatus comprising a disposable device having at least one first duct defining a passage section for passage of the biological tissue, the first duct having a first end and a second end,
   wherein each end of the first duct is designed for connection to an inlet/outlet opening of a respective device for handling and/or collecting the biological tissue, in particular a pump device,
   wherein the disposable device comprises a duct body which is at least in part deformable via a compression exerted thereon, to define at least one deformable portion of the first duct,
   wherein the disposable device further comprises an adjustment arrangement operable for causing a deformation of the duct body at the deformable portion, and thereby obtaining a change of the passage section of the first duct at the deformable portion while enabling the biological tissue to flow between the first end and the second end of the first duct.

2. The apparatus according to claim 1, wherein the adjustment arrangement is operable for causing a local compression of the duct body at the deformable portion, and thereby obtain a reduction of the passage section of the first duct at the deformable portion while enabling the biological tissue to flow between the first end and the second end of the first duct.

3. The apparatus according to claim 2,
   wherein the disposable device comprises a supporting body, and the duct body defines at least a longitudinally extended part of the first duct which comprises the deformable portion,
   wherein the adjustment arrangement comprises at least one passage of the supporting body which is susceptible of receiving at least partially a corresponding movable adjusting member, the movable adjusting member having a leading end facing a region of the deformable portion,
   wherein the at least one passage extends in a transverse direction relative to said longitudinally extended part of the first duct, and has a leading end facing a region of the deformable portion,
   and wherein the adjustment arrangement is operable for causing a displacement of the movable adjusting member within the at least one passage towards said region of the deformable portion, such that the leading end of the movable adjusting member causes said local compression.

4. The apparatus according to claim 2,
   wherein the duct body has at least one area with reduced thickness at the deformable portion, said area with reduced thickness defining a recessed seat in the duct body, the recessed seat having a bottom and being susceptible of receiving at least partially a corresponding movable adjusting member having a leading end,
   wherein the recessed seat extends axially in a transverse direction relative to a length direction of the first duct,
   and wherein the adjustment arrangement is operable for causing a displacement of the movable adjusting member within the recessed seat towards the bottom thereof, such that the leading end of the movable adjusting member causes said local compression.

5. The apparatus according to claim 3, wherein the adjusting member is susceptible of assuming a plurality of operative positions, to which different passage sections of the first duct correspond, which enable the biological tissue to flow between the first end and the second end of the first duct.

6. The apparatus according to claim 1, wherein:
   the disposable device comprises a supporting body, and the duct body defines at least a longitudinally extended part of the first duct which comprises the deformable portion,
   the supporting body is formed with a substantially rigid material and at least said longitudinally extended part of the duct body is formed with an elastically deformable or flexible material, and
   said longitudinally extended part of the duct body is positioned in contact with or within the supporting body.

7. The apparatus according to claim 6, wherein the duct body has a flat and oblong shape, the duct body having a first surface facing a second surface of the supporting body to define therebetween at least one part of the first duct which includes the deformable portion.

8. The apparatus according to claim 6, wherein the supporting body comprises at least one first body part and one second body part which are fixed to each, the first body part and the second body part of the supporting body having facing surfaces shaped to define a transverse passage into which the duct body is at least partially inserted.

9. The apparatus according to claim 6, wherein the first end and the second end of the first duct are defined in the supporting body, and wherein the duct body is arranged in an intermediate position with respect to the first end and the second end, to defines said longitudinally extended part of the first duct.

10. The apparatus according to claim 1,
wherein the disposable device comprises a supporting body of the duct body,
wherein the duct body has at least one transparent portion defining a corresponding portion of the first duct, and
wherein the supporting body comprises one or more passages for optical detection in a region thereof corresponding to said transparent portion, the passage for optical detection or each passage for optical detection extending in the supporting body in a transverse direction relative to the transparent portion.

11. The apparatus according to claim 10,
wherein two passages for optical detection are defined in the supporting body at diametrically opposite positions, corresponding to diametrically opposite sides of the first duct, the two passages for optical detection being substantially coaxial to one another,
wherein a transparent part of the first duct extends in a length direction between said two passages for optical detection.

12. The apparatus according to claim 1, wherein the disposable device comprises a second duct for introduction of the biological tissue in the first duct, the second duct having an inlet and an outlet, the outlet of the second duct being connected to the first duct in an intermediate position with respect to the first and the second ends, said intermediate position being upstream or downstream of the deformable portion.

13. The apparatus according to claim 12, wherein between the inlet and the outlet of the second duct there is provided at least one from among a pre-treatment device, a device for mechanical filtration, a unidirectional valve.

14. The apparatus according to claim 1,
wherein the duct body comprises a first body part and a second body part which are configured as separate elements facing to one another,
wherein at least one part of the first duct including the deformable portion is defined between facing surfaces of the first and second body parts,
wherein at least the first body part is flexible,
and wherein the adjustment arrangement is operable for causing the first body part to move towards the second body part at least at the deformable portion, and thereby obtain a corresponding reduction of the passage section of the first duct.

15. The apparatus according to claim 14, wherein one of said facing surfaces has a plurality of protrusions, and the other one of said facing surfaces has a plurality of recesses susceptible of receiving at least partially said protrusions.

16. The apparatus according to claim 1, having one or more of the following characteristics:
the disposable device has a supporting body and at least one part of the first duct is defined between facing surfaces of the supporting body and the duct body;
the disposable device has a supporting body, the supporting body and the duct body having respective elements for reciprocal positioning;
the disposable device has a supporting body, at least one of the supporting body or the duct body having respective elements for defining seats or passages for enabling an optical detection;
the disposable device comprises a supporting body and at least one of the supporting body or the duct body is at least partly transparent to enable an optical detection;
the disposable device is prearranged for association to at least one optical transmitter and one optical receiver;
at least one part of the first duct is defined by a supporting body of the disposable device;
the first end and the second end of the first duct comprise respective attachments for releasable connection to said inlet/outlet opening of a respective device for handling and/or collecting the biological tissue;
the first duct comprises a plurality of canalizations and/or of recessed parts and/or protruding parts;
the apparatus comprises a supporting structure having at least one seat for supporting and/or positioning at least one of the disposable device and a device for handling and/or collecting the biological tissue;
the adjustment arrangement is configured to be operable manually;
the adjustment arrangement is configured to be operated via control equipment;
the first duct is defined at least in part by a tube;
the first duct has a substantially polygonal inner profile.

17. The apparatus according to claim 1, wherein the duct body comprises a flexible and deformable tube.

18. The apparatus according to claim 1, wherein the adjustment arrangement is accessible and/or operable from outside the disposable device, without requiring disassembling of the disposable device or replacement of internal parts thereof.

19. An apparatus for disgregating a biological tissue, in particular an adipose tissue including stem and/or multipotent cells for use in regenerative medicine, the apparatus comprising a disposable device having at least one first duct defining a passage section for passage of the biological tissue, the first duct having a first end and a second end,
wherein each end of the first duct is designed for connection to an inlet/outlet opening of a respective device for handling and/or collecting the biological tissue, in particular a pump device,
wherein the disposable device comprises a duct body which extends in a length direction and defines at least a part of the first duct,
wherein the disposable device further comprises an adjustment arrangement operable for causing a change of the passage section of the first duct,
wherein the duct body has at least one through-opening in an intermediate position of the first duct, which extends in a transverse direction relative to the length direction and through which a corresponding adjusting member is displaceable,
wherein the adjusting member has a leading end which faces the inside of the first duct or protrudes thereinto via the at least one through-opening,
wherein the adjustment arrangement is operable for causing displacements of the adjusting member towards the inside of the first duct, and thereby varying the passage section of the first duct while enabling the biological tissue to flow between the first end and the second end of the first duct.

* * * * *